United States Patent
Cosman, Jr. et al.

(10) Patent No.: US 10,136,943 B1
(45) Date of Patent: Nov. 27, 2018

(54) ELECTROSURGICAL SYSTEM

(71) Applicant: COSMAN INSTRUMENTS, LLC, Burlington, MA (US)

(72) Inventors: Eric R. Cosman, Jr., Belmont, MA (US); Eric R. Cosman, Sr., Belmont, MA (US)

(73) Assignee: COSMAN INSTRUMENTS, LLC, Burlington, MA (US)

(*) Notice: Subject to any disclaimer, the term of this patent is extended or adjusted under 35 U.S.C. 154(b) by 829 days.

(21) Appl. No.: 14/530,699

(22) Filed: Nov. 1, 2014

Related U.S. Application Data

(63) Continuation-in-part of application No. 14/520,305, filed on Oct. 21, 2014.

(51) Int. Cl.
*A61B 18/14* (2006.01)
*A61B 18/00* (2006.01)

(52) U.S. Cl.
CPC ............. *A61B 18/1492* (2013.01); *A61B 2018/00029* (2013.01); *A61B 2018/00577* (2013.01); *A61B 2018/00589* (2013.01); *A61B 2018/00791* (2013.01)

(58) Field of Classification Search
CPC ............ A61B 18/1492; A61B 18/1477; A61B 2018/00577; A61N 2018/1475; A61N 2018/00791
See application file for complete search history.

(56) References Cited

U.S. PATENT DOCUMENTS

| | | |
|---|---|---|
| 4,411,266 A | 10/1983 | Cosman |
| 4,565,200 A | 1/1986 | Cosman |
| 4,566,454 A | 1/1986 | Mehl et al. |
| 4,597,379 A | 7/1986 | Kihn et al. |
| 4,727,874 A | 3/1988 | Bowers et al. |
| 4,807,620 A | 2/1989 | Strul et al. |
| 5,433,739 A | 7/1995 | Sluijter et al. |
| 5,571,147 A | 11/1996 | Sluijter et al. |
| 5,769,847 A | 6/1998 | Panescu et al. |
| 5,951,546 A | 9/1999 | Lorentzen |
| 5,983,141 A | 11/1999 | Sluijter et al. |
| 6,053,912 A * | 4/2000 | Panescu ............ A61B 18/1492 606/31 |
| 6,104,959 A | 8/2000 | Spertell |
| 6,161,048 A | 12/2000 | Sluijter et al. |
| 6,246,912 B1 | 6/2001 | Sluijter et al. |

(Continued)

FOREIGN PATENT DOCUMENTS

| | | |
|---|---|---|
| WO | WO 99/40859 | 8/1999 |
| WO | WO 99/40860 | 8/1999 |
| WO | WO 00/59394 | 10/2000 |

OTHER PUBLICATIONS

Cosman et al. "Theoretical Aspects of Radiofrequency Lesions in the Dorsal Root Entry Zone," *Neurosurgery*, vol. 15, No. 6, p. 945-950 (1984).

*Primary Examiner* — Michael Kahelin

(74) *Attorney, Agent, or Firm* — Steptoe & Johnson LLP

(57) ABSTRACT

An RF electrode can have a straight shaft to generate an RF heat lesion that is asymmetric about the central axis of the cannula through which the RF electrode is introduced into bodily tissue. An electrode can be inserted into a cannula, and an electrosurgical generator can apply current between the active tip of the electrode and the active tip of the cannula to heat tissue.

16 Claims, 22 Drawing Sheets

(56) References Cited

U.S. PATENT DOCUMENTS

| | | | |
|---|---|---|---|
| 6,259,952 B1 | 7/2001 | Sluijter et al. | |
| 6,301,506 B1 | 10/2001 | Den Boer et al. | |
| 6,321,120 B1 | 11/2001 | Surbeck et al. | |
| 6,397,106 B1 | 5/2002 | DeBrouse | |
| 6,402,739 B1 | 6/2002 | Neev | |
| 6,428,537 B1 | 8/2002 | Swanson et al. | |
| 6,440,127 B2 | 8/2002 | McGovern et al. | |
| 6,447,505 B2 | 9/2002 | McGovern et al. | |
| 6,482,204 B1 | 11/2002 | Lax et al. | |
| 6,517,534 B1 | 2/2003 | McGovern et al. | |
| 6,530,922 B2 | 3/2003 | Cosman et al. | |
| 6,692,493 B2 | 2/2004 | McGovern et al. | |
| 6,743,226 B2 | 6/2004 | Cosman et al. | |
| 6,843,789 B2 | 1/2005 | Goble | |
| 6,853,864 B2 | 2/2005 | Litovitz | |
| 6,869,430 B2 | 3/2005 | Balbierz et al. | |
| 7,522,953 B2 | 4/2009 | Kaula et al. | |
| 7,553,309 B2 | 6/2009 | Buysse et al. | |
| 7,574,257 B2 | 8/2009 | Rittman, III | |
| 7,862,563 B1 * | 1/2011 | Cosman | A61B 18/1477 606/41 |
| 2002/0156472 A1 | 10/2002 | Lee et al. | |
| 2002/0165531 A1 | 11/2002 | Goble | |
| 2003/0032951 A1 | 2/2003 | Rittman et al. | |
| 2003/0212390 A1 | 11/2003 | Chen et al. | |
| 2005/0010203 A1 * | 1/2005 | Edwards | A61B 18/00 606/32 |
| 2005/0234443 A1 * | 10/2005 | Rioux | A61B 18/1477 606/41 |
| 2007/0032835 A1 | 2/2007 | Rittman | |
| 2008/0262490 A1 | 10/2008 | Williams | |

* cited by examiner

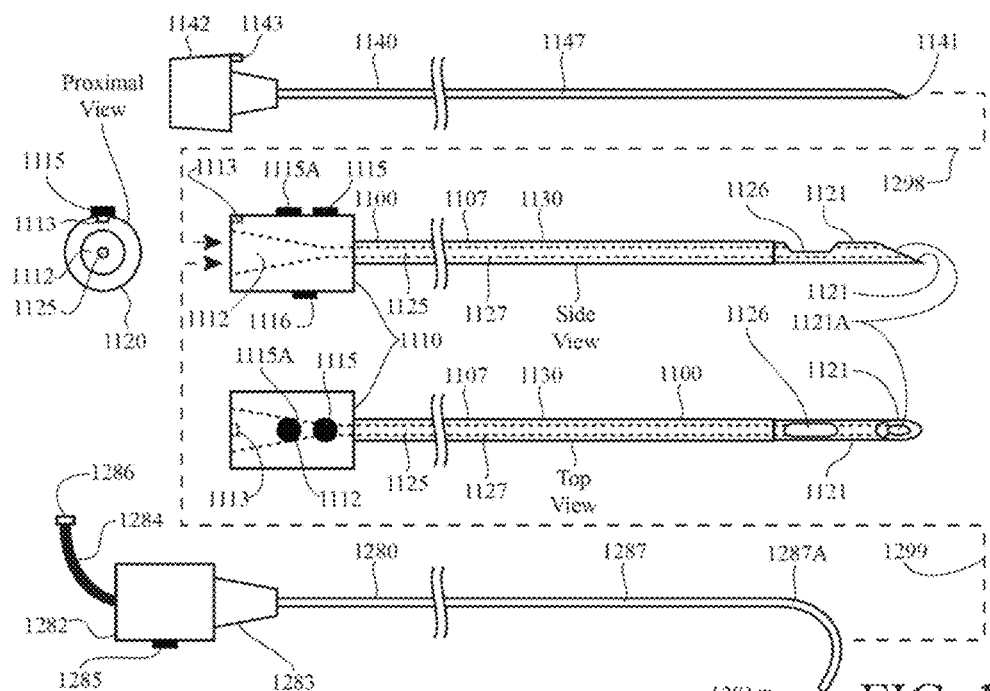
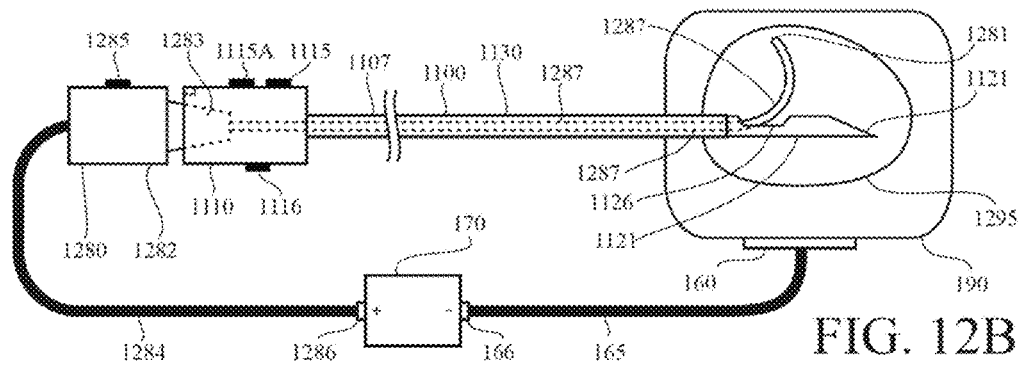
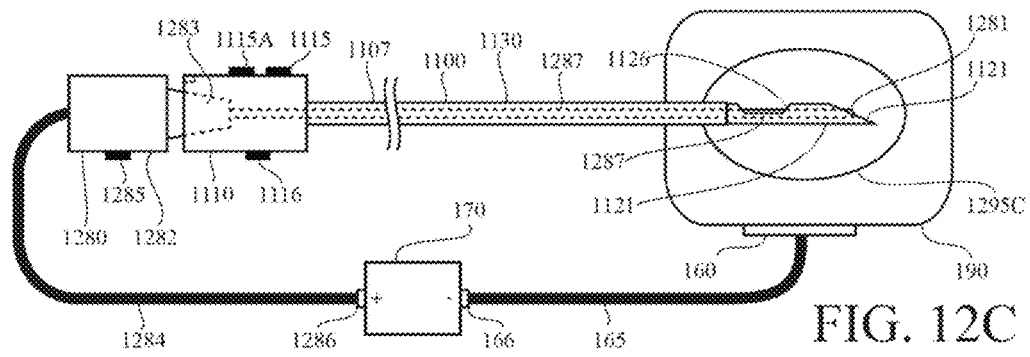
FIG. 12A
FIG. 12B
FIG. 12C

ELECTROSURGICAL SYSTEM

PRIORITY CLAIM

This application is a continuation in part of U.S. application Ser. No. 14/520,305, filed Oct. 21, 2014, which is incorporated by reference in its entirety.

TECHNICAL FIELD

This invention relates generally to the advances in medical systems and procedures for prolonging and improving human life. The present invention also relates generally to systems and methods for electrodes that extend out of an introducer cannula. The present invention also relates generally to systems and methods of side-outlet electrodes. The present invention also relates generally to a system and method for applying energy, particularly high-frequency (HF) energy, such as radiofrequency (RF) electrical energy, to a living body. The present invention also relates generally to a system and method for apply energy for the purpose of tissue ablation.

BACKGROUND

The use of radiofrequency (RF) generators and electrodes to be applied to tissue for pain relief or functional modification is well known. For example, the RFG-3C plus RF lesion generator of Radionics, Inc., Burlington, Mass. and its associated electrodes enable electrode placement near target tissue and the heating of the target tissue by RF power dissipation of the RF signal output in the target tissue. For example, the G4 generator of Cosman Medical, Inc., Burlington, Mass. and its associated electrodes (such as the Cosman CSK electrode), cannula (such as the Cosman CC and RFK cannulae), and ground pads (such as the Cosman DGP-PM) enable electrode placement near target tissue and heating of the target tissue by RF power dissipation of the RF signal output in the target tissue. Temperature monitoring of the target tissue by a temperature sensor in the electrode can control the process. Heat lesions with target tissue temperatures of 60 to 95 degrees Celsius are common. Tissue dies and nerves are severed by sustained heating above about 45 degrees Celsius, so this process produces the RF heat lesion. RF generator output is also applied using a pulsed RF method, whereby RF output is applied to tissue intermittently such that tissue is exposed to high electrical fields and average tissue temperature are lower, for example 42 degrees Celsius or less.

RF generators and electrodes are used to treat pain, cancer, and other diseases. Related information is given in the paper by Cosman E R and Cosman B J, "Methods of Making Nervous System Lesions", in Wilkins R H, Rengachary S (eds.); Neurosurgery, New York, McGraw Hill, Vol. 3, 2490-2498; and is hereby incorporated by reference in its entirety. Related information is given in the book chapter by Cosman E R Sr and Cosman E R Jr. entitled "Radiofrequency Lesions.", in Andres M. Lozano, Philip L. Gildenberg, and Ronald R. Tasker, eds., Textbook of Stereotactic and Functional Neurosurgery (2nd Edition), 2009, and is hereby incorporated by reference in its entirety. A research paper by E. R. Cosman, et al., entitled "Theoretical Aspects of Radiofrequency Lesions and the Dorsal Root Entry Zone," by Cosman, E. R., et al., Neurosurg 1984; 15:945-950, describes various techniques associated with radio frequency lesions and is hereby incorporated by reference herein in its entirety. Research papers by S. N. Goldberg, et al., entitled "Tissue Ablation with Radio Frequency: Effect of Probe Size, Gauge, Duration, and Temperature on Lesion Volume," Acad. Radiol., Vol. 2, pp. 399-404 (1995), and "Thermal Ablation Therapy for Focal Malignancy," AJR, Vol. 174, pp. 323-331 (1999), described techniques and considerations relating to tissue ablation with radio frequency energy and are hereby incorporated by reference herein in its entirety. For a given electrode temperature, size of electrode, and time of heating, you can predict reliably ablation size as described in the papers entitled "Theoretical Aspects of Radiofrequency Lesions and the Dorsal Root Entry Zone," by Cosman, E. R., et al., Neurosurg 15:945-950, 1984, and "Bipolar Radiofrequency Lesion Geometry: Implications for Palisade Treatment of Sacroiliac Joint Pain." by E. R. Cosman Jr and C. D. Gonzalez, Pain Practice 2011; 11(1): 3-22 (hereinafter "Cosman and Gonzalez"), which are herein incorporated by reference in their entireties.

The use of high frequency (HF) electrodes for heat ablation treatment in the destruction of tumors is well known. One example is the destruction of cancerous tumors of the kidney using radio frequency (RF) heat ablation. A paper by D. W. Gervais, et al., entitled "Radio Frequency Ablation of Renal Cell Carcinoma: Early Clinical Experience," Radiology, Vol. 217, No. 2, pp. 665-672 (2000), describes using a rigid tissue perforating and penetrating electrode that has a sharpened tip to self-penetrate the skin and tissue of the patient. This paper is hereby incorporated by reference herein in its entirety. A paper by Luigi Solbiati et al. entitled "Hepatic Metastases: Percutaneous Radiofrequency Ablation with Cool-Tip Electrodes," Radiology 1997, vol. 205, no. 2, pp. 367-373 describes various techniques and considerations relating to tissue ablation with RF electrodes which are internally-cooled by circulating fluid, and is incorporated herein by reference. A paper by Rosenthal et al entitled "Percutaneous Radiofrequency Treatment of Osteoid Osteoma," Seminars in Musculoskeletal Radiology, Vol. 1, No. 2, 1997 reports the treatment of a primary benign bone tumor and the management of concomitant pain using a percutaneously placed radiofrequency electrode, and is incorporated herein by reference. United States patents by E. R. Cosman and W. J. Rittman, III, entitled "Cool-Tip Electrode Thermal Surgery System," U.S. Pat. No. 6,506, 189 B1, date of patent Jan. 14, 2003, and "Cluster Ablation Electrode System," U.S. Pat. No. 6,530,922 B1, date of patent Mar. 11, 2003, described systems and method related to tissue ablation with radiofrequency energy and electrodes and are hereby incorporated by reference herein in their entirety. Another example of probes for high-frequency tissue ablation includes microwave (MW) antennae. Another example of probes for tissue ablation are irreversible-electroporation (IRE) probes. Another example of probes for tissue ablation are cryogenic ablation probes.

Each Cosman CC cannula and RFK cannula, manufactured by Cosman Medical, Inc. in Burlington, Mass., includes a pointed metal shaft that is insulated except for an uninsulated electrode tip. The CC cannula has a straight shaft. The RFK cannula has a curved shaft; one advantage of a curved shaft is that it can facilitate maneuvering of the cannula's tip within tissue. Some cannula include sharp distal points, and some cannula include blunt distal points. Some cannula, for example RFK-C101020B, include a side opening to the cannula body lumen in the active tip. Each cannula includes a removable stylet rod that can occlude the inner lumen through the cannula's shaft and obturate the cannula's shaft (which can, for example, facilitate insertion of the cannula into solid tissue), and can be removed to allow for injection of fluids through the cannula shaft and out from the cannula tip, or insertion of instruments, such as an electrode. Each cannula has a hub at its proximal end, the hub sized for manual manipulation of the cannula and having a luer port to accommodate an injection syringe or a thermocouple (TC) electrode, for example the Cosman CSK electrode, Cosman TCD electrode, and Cosman TCN electrode, that can deliver electrical signal output, such as RF voltage or stimulation, to the uninsulated cannula active tip and that can measure the temperature at the cannula active tip. The Cosman CSK and TCD electrodes have a shaft that is stainless steel. The Cosman TCN electrode has a shaft that is Nitinol. One CC or RFK cannula works with one CSK, TCD, or TCN electrode as a two-piece RF electrode system configured for ablation of bodily tissue with temperature control. The Cosman CU electrode is an example of a one-piece RF electrode system wherein the electrode shaft has a tissue-piecing tip, insulation over the proximal shaft to produce an active electrode tip at the shaft distal end, a thermocouple temperature sensor with the active electrode tip, an injection port, a connection to an RF generator, and a lumen within the shaft to provide for fluid injection. The Cosman CR electrode is an example of a one-piece, tissue-piercing, radiofrequency, injection electrode that does not include a temperature sensor. The Cosman CP electrode is an example of a one-piece stimulation electrode system wherein the electrode shaft has a tissue-piecing tip, insulation over the proximal shaft to produce an active electrode tip at the shaft distal end, an injection port, a connection to an nerve-stimulation signal generator (which can be included in an RF generator, in some embodiments), and a lumen within the shaft to provide for fluid injection. Related information is given in Cosman Medical brochure "Four Electrode RF Generator", brochure number 11682 rev A, copyright 2010, Cosman Medical, Inc., and is hereby incorporated by reference herein in its entirety.

Side-outlet RF electrode system include at least one electrode that protrudes from at least one outlet in the side of a cannula shaft. Examples of side-outlet electrode systems are shown in U.S. Pat. No. 4,565,200 by E. R. Cosman, U.S. Pat. No. 5,683,384 by E.1. Gough et al., U.S. Pat. No. 5,672,173 by E. J. Gough and A. A. Stein, U.S. Patent Application Publication Number 2004/0260282 by E. J. Gough and A. A. Stein, and patent application PCT/US2013/027038 by Stryker Corporation, which are hereby incorporated by reference in their entirety. Examples of side-outlet electrode systems are the SSE Siegfried Side-Outlet Stereotactic Electrode, ZHK Zervas Hypophysectomy Kit, and TCS-1 Side Outlet Stereotactic Electrode Kit systems manufactured by Radionics (Burlington, Mass.) in the 1970s and 1980s. Related information is presented in Cosman E R, Cosman B J. Methods of Making Nervous System Lesions. In: Wilkins R H, Rengachary S S, eds. Neurosurgery. New York: McGraw-Hill; 1984: 2490-2499 which is hereby incorporated by reference in its entirety. Related information is given in the book chapter by Cosman E R Sr and Cosman E R Jr. entitled "Radio frequency Lesions", in Andres M. Lozano, Philip L. Gildenberg, and Ronald R. Tasker, eds., Textbook of Stereotactic and Functional Neurosurgery (2nd Edition), 2009, which is hereby incorporated by reference in its entirety.

SUMMARY

In one aspect, the present invention relates to the use of an RF electrode having a straight shaft to generate an RF heat lesion that is asymmetric about the central axis of the cannula through which the RF electrode is introduced into bodily tissue.

In one aspect, the present invention relates to the use of an RF electrode having a straight shaft to bias the formation of an RF heat lesion to one side of the active tip of the cannula through which the RF electrode is introduced into bodily tissue and to which the electrode conducts RF current.

In one aspect, the present invention relates to the use of an RF electrode whose shaft is not shaped to define a bend into order to enlarge the size of the heat lesion generated around the active tip of the cannula through which the RF electrode is inserted into bodily tissue and which the electrode energizes.

In one aspect, the present invention relates to a straight electrode and a cannula to generate an RF heat lesion in bodily tissue wherein the straight electrode extends from a side opening in the cannula shaft.

In one aspect, the present invention relates to an RF cannula which can be used with a straight RF electrode to generate a RF lesion in bodily tissue around both the active tip of the cannula and an extension of the conductive electrode shaft out from the cannula lumen through a hole in the side wall of the cannula active tip.

In one aspect, the present invention relates to an RF cannula which can be used with an RF electrode whose shaft is not shaped to define a bend, in order to generate an asymmetric RF lesion in bodily tissue around both the active tip of the cannula and an extension of the conductive electrode shaft out from the cannula lumen through a hole in the side wall of the cannula active tip.

In one aspect, the present invention relates to an RF cannula which can be used with an RF electrode whose shaft is not shaped to define a bend, in order to generate a RF lesion in bodily tissue around both the active tip of the cannula and an extension of the conductive electrode shaft out from the cannula lumen through a hole in the side wall of the cannula active tip, wherein the electrode shaft remains substantially straight over its entire length, including at points within and around the cannula side opening.

In one aspect, the present invention relates to an RF cannula which can be used with an RF electrode whose shaft is stiff and straight, in order to generate a RF lesion in bodily tissue around both the active tip of the cannula and an extension of the conductive electrode shaft out from the cannula lumen through a hole in the side wall of the cannula active tip, wherein the electrode shaft remains substantially straight over its entire length, including at points within and around the cannula side opening.

In one aspect, the present invention relates to an internally-cooled RF electrode and RF cannula wherein the conductive shaft of the internally-cooled RF electrode extends into tissue from a side opening in the conductive active tip of the cannula, and both the electrode conductive shaft and the cannula active tip conduct RF current into the bodily tissue.

In one aspect, the present invention relates to an RF electrode and a curved-tip RF cannula having a side opening to the cannula lumen from which the conductive shaft of the RF electrode exclusively extends into bodily tissue through the side opening when the electrode is fully inserted into the cannula lumen from the cannula non-tissue-penetrating end.

In one aspect, the present invention relates to a straight-shaft RF electrode and a curved-tip RF cannula having a side opening to the cannula lumen from which the shaft of the RF electrode consistently extends into bodily tissue through the side opening when the electrode is fully inserted into the cannula lumen from the cannula non-tissue-penetrating end.

In one aspect, the present invention relates to an RF electrode and a straight-tip RF cannula having a side opening to the cannula lumen from which the shaft of the RF electrode consistently extends into bodily tissue through the side opening when the electrode is fully inserted into the cannula lumen from the cannula non-tissue-penetrating end.

In one aspect, the present invention relates to an RF electrode having a bent shaft, and a straight-tip RF cannula having a side opening to the cannula lumen from which the bent shaft of the RF electrode consistently extends into bodily tissue through the side opening when the electrode is fully inserted into the cannula lumen from the cannula non-tissue-penetrating end.

In one aspect, the present invention relates to an RF electrode having a bent shaft, and a bent-tip RF cannula having a side opening to the cannula lumen from which the bent shaft of the RF electrode extends into bodily tissue through the side opening when the electrode is fully inserted into the cannula lumen from the cannula non-tissue-penetrating end, irrespective of the rotational orientation of the electrode shaft within the cannula shaft.

In one aspect, the present invention relates to an RF electrode having a bent shaft, and a RF cannula having a side opening to the cannula lumen from which the bent shaft of the RF electrode extends into bodily tissue through the side opening when the electrode is fully inserted into the cannula lumen from the cannula non-tissue-penetrating end, wherein the electrode shaft cannot be fully inserted into the cannula lumen unless the electrode is in a rotational orientation around the electrode longitudinal axis in which the electrode shaft extends through the side opening.

In one aspect, the present invention relates to an RF cannula having a flap of the cannula side wall that forms an opening to the cannula lumen through the cannula side wall, and that directs out of the opening the shaft of an electrode inserted into the cannula lumen through the non-tissue-penetrating end of the cannula.

In one aspect, the present invention relates to an RF cannula having a closed distal end, a side opening to the cannula lumen in the cannula active tip, a structure in the lumen configured to direct an electrode shaft out from the opening into tissue when the electrode shaft is inserted into the cannula hub.

In one aspect, the present invention relates to an RF electrode having a shaft include two bends configured to facilitate sliding of the electrode shaft through the lumen of a cannula.

In one aspect, the present invention relates to an RF electrode having a shaft include two bends configured to facilitate sliding of the electrode shaft through the lumen of a cannula into which the electrode shaft is inserted, and to provide for user selection of the rotational orientation of the electrode shaft distal end within the cannula lumen.

In one aspect, the present invention relates to an RF electrode having a shaft include two bends configured to facilitate sliding of the electrode shaft through the lumen of a cannula into which the electrode shaft is inserted, and to provide for direction of the distal tip through at least two branches of the lumen by rotation of the electrode shaft within the lumen.

In one aspect, the present invention relates to an RF electrode having a shaft include two bends configured to ensure contact between the walls of a cannula lumen through which the electrode shaft is inserted.

In one aspect, the present invention relates to an RF electrode having a conductive shaft include two bends configured to ensure electrical contact between the conductive walls of a cannula lumen through which the electrode shaft is inserted.

In one aspect, the present invention relates to an RF electrode having a shaft include two bends configured to position the distal tip of the electrode shaft within the lumen of a cannula through which the electrode shaft is inserted.

In one aspect, the present invention relates to an RF cannula and RF electrode assembly, the electrode having a conductive shaft shaped to form at least one bend, the cannula having a straight shaft partially covered by electrical insulation and partially uncovered to form an active tip region, a lumen through the cannula shaft having a side opening through the wall of the active tip, the electrode shaft being configured to be inserted into the cannula lumen and conduct an electrical potential to the cannula active tip by contacting the walls of the cannula lumen, the electrode shaft being configured to extend out of the cannula side opening when the electrode is inserted into the cannula lumen in a first rotational orientation about the cannula longitudinal axis, and the electrode shaft being configured to enter the lumen within the active tip beyond the cannula side opening when the electrode is inserted into the cannula lumen in a second rotational orientation about the cannula longitudinal axis.

In one aspect, the present invention relates to an RF cannula and RF electrode assembly, the electrode having a conductive shaft shaped to form at least one bend, the cannula having a straight shaft partially covered by electrical insulation and partially uncovered to form an active tip region, a lumen through the cannula shaft having a side opening through the wall of the active tip, the electrode shaft being configured to be inserted into the cannula lumen and conduct an electrical potential to the cannula active tip by contacting the walls of the cannula lumen, the electrode shaft being configured to extend out of the cannula side opening when the electrode is inserted into the cannula lumen in a first rotational orientation about the cannula longitudinal axis, the electrode shaft being configured to pass by the cannula side opening and stay within the cannula lumen when the electrode is inserted into the cannula lumen in a second rotational orientation about the cannula longitudinal axis, the electrode including an electrode indicia, the cannula including two distinguishable cannula indicia near the end of the cannula shaft into which the electrode shaft is inserted, the first cannula indicia aligning with the electrode indicia when the electrode shaft is inserted into the cannula shaft in the first rotational orientation, and the second cannula indicia aligning with the electrode indicia when the electrode shaft is inserted into the cannula shaft in the second rotational orientation.

In one aspect, the present invention relates to an RF cannula and RF electrode assembly, the electrode having a conductive shaft shaped to form a hook-shaped bend, the cannula having a straight shaft partially covered by electrical insulation and partially uncovered to form an active tip region, a lumen through the cannula shaft having a side opening through the wall of the active tip, the electrode shaft being configured to be inserted into the cannula lumen and conduct an electrical potential to the cannula active tip by contacting the walls of the cannula lumen, the electrode shaft being configured to extend out of the cannula side opening when the electrode is inserted into the cannula lumen in a first rotational orientation about the cannula longitudinal axis, and the electrode shaft being configured to pass by the cannula side opening and stay within the cannula lumen when the electrode is inserted into the cannula lumen in a second rotational orientation about the cannula longitudinal axis.

In one aspect, the present invention relates to an RF cannula and RF electrode assembly, the electrode having a conductive shaft shaped to form at least one bend, the cannula having a shaft partially covered by electrical insulation and partially uncovered to form an active tip region, a lumen through the cannula shaft having a side opening through the wall of the active tip, the lumen through the cannula shaft having a distal opening through the tissue-piercing point of the cannula shaft, the electrode shaft being configured to be inserted into the cannula lumen and conduct an electrical potential to the cannula active tip by contacting the walls of the cannula lumen, the electrode shaft being configured to extend out of the cannula side opening when the electrode is inserted into the cannula lumen to a first position and in a first rotational orientation about the cannula longitudinal axis, the electrode shaft being configured to pass by the cannula side opening and stay within the cannula lumen within the active tip when the electrode is inserted into the cannula lumen to a second position and in a second rotational orientation about the cannula longitudinal axis, and the electrode shaft being configured to pass by the cannula side opening and to extend out of the cannula distal opening when the electrode is inserted into the cannula lumen to a third position and in the second rotational orientation about the cannula longitudinal axis.

In one aspect, the present invention relates to an electrosurgical ablation system including an electrode and a cannula, the electrode having an electrically-insulated shaft and a conductive active tip, the cannula having an electrically-insulated shaft and a conductive active tip inserted into bodily tissue, the cannula having a side opening to the cannula lumen in the cannula active tip, the electrode shaft being inserted into the cannula lumen through the non-tissue-piercing end of the cannula shaft and extending out of the side opening into the bodily tissue such that the active tip of the electrode and the active tip of the cannula are physically separately and electrically isolated within the assembly of the electrode and the cannula, an electrosurgical generator applying current between the active tip of the electrode and the active tip of the cannula to heat the tissue.

In one aspect, the present invention relates to an electrosurgical ablation system including an internally-cooled electrode and a cannula, the electrode having an electrically-insulated shaft and a conductive active tip, the cannula having an electrically-insulated shaft and a conductive active tip inserted into bodily tissue, the cannula having a side opening to the cannula lumen in the cannula active tip, the electrode shaft being inserted into the cannula lumen through the non-tissue-piercing end of the cannula shaft and extending out of the side opening into the bodily tissue such that the active tip of the electrode and the active tip of the cannula are physically separately and electrically isolated within the assembly of the electrode and the cannula, an electrosurgical generator applying current between the active tip of the electrode and the active tip of the cannula to heat the tissue.

In one aspect, the present invention relates to an electrosurgical ablation system including an electrode and a cannula, the electrode having an electrically-insulated shaft and a conductive active tip, the cannula having an electrically-insulated shaft and a conductive active tip inserted into bodily tissue, the cannula having a side opening to the cannula lumen in the cannula active tip, the electrode shaft being inserted into the cannula lumen through the non-tissue-penetrating end of the cannula shaft and extending out of the side opening into the bodily tissue such that the active tip of the electrode and the active tip of the cannula are physically separately and electrically isolated within the assembly of the electrode and the cannula, the electrode including a hub at its non-tissue-penetrating end, the cannula including a hub at its non-tissue-penetrating end, the electrode hub conducting a signal to the cannula active tip by abutting a conductive surface of the cannula hub, an electrosurgical generator applying current between the active tip of the electrode and the active tip of the cannula to heat the tissue.

In one aspect, the present invention relates to an electrosurgical ablation system including an electrode and a cannula, the electrode having an electrically-insulated shaft and a conductive active tip, the cannula having an electrically-insulated shaft and a conductive active tip inserted into bodily tissue, the cannula having a distal opening to the cannula lumen at the tissue-penetrating point of the cannula shaft, the electrode shaft being inserted into the cannula lumen through the non-tissue-piercing end of the cannula shaft and extending out of the distal opening into the bodily tissue such that the active tip of the electrode and the active tip of the cannula are physically separately and electrically isolated within the assembly of the electrode and the cannula, an electrosurgical generator applying current between the active tip of the electrode and the active tip of the cannula to heat the tissue.

In one aspect, the present invention relates to an electrosurgical ablation system including an internally-cooled electrode and a cannula, the electrode having an electrically-insulated shaft and a conductive active tip, the cannula having an electrically-insulated shaft and a conductive active tip inserted into bodily tissue, the cannula having a distal opening to the cannula lumen at the tissue-penetrating point of the cannula shaft, the electrode shaft being inserted into the cannula lumen through the non-tissue-piercing end of the cannula shaft and extending out of the distal opening into the bodily tissue such that the active tip of the electrode and the active tip of the cannula are physically separately and electrically isolated within the assembly of the electrode and the cannula, an electrosurgical generator applying current between the active tip of the electrode and the active tip of the cannula to heat the tissue.

In one aspect, the invention relates to ablation probes, electrodes, and cannula that can be used in one or more organs in the body, including without limitation organs in the following list: brain, spine, liver, lung, bone, vertebral bone, kidney, abdominal structures, nerves, peripheral nerve, central nervous system, peripheral nervous system, pancreas. The invention relates to probes configured for use for one or more medical applications, including without limitation applications selected from the following list: the treatment of cancerous tumors, treatment of pathological target volumes, treatment of a pain, treatment of movement disorders, treatment of high blood pressure, treatment of cardiac malfunction, or treatment of tissue target volumes in nervous tissue, a nerve located within a bone, bone tissue, cardiac tissue, muscle tissue, or other types of bodily tissues.

Other examples of embodiments of systems and methods of the present invention are given in the rest of this patent. The details of embodiments of the invention are set forth in the accompanying drawings and description below. Other features, objects, and advantages of the invention will be apparent from the description and drawings and from the claims.

BRIEF DESCRIPTION OF THE DRAWINGS

In the drawings that constitute a part of the specification, embodiments exhibited various forms and features hereof are set forth, specifically:

FIG. 12A is a schematic diagram showing an RF electrode system including an electrode and a cannula; the electrode conductive shaft having a hook-shaped curve at its tissue-piercing end; the cannula conductive, tubular shaft being covered by electrical insulation except for an uncovered active tip region at the tissue-piercing end of the cannula shaft; the cannula active tip including a side opening to the cannula lumen near the sharpened bevel at the tissue-piercing end of the cannula shaft; the electrode shaft being configured for insertion of the lumen of the cannula shaft through the cannula hub at the cannula non-tissue-piercing end, and for conduction of an electrical signal to the cannula active tip by contact between the cannula shaft and the electrode shaft when the electrode is inserted into the cannula lumen; the electrode hub at the electrode non-tissue-penetrating end having an curve mark indicating the direction of the electrode shaft curve; the cannula hub including an opening mark aligned circumferentially with the side opening in the cannula active tip; the cannula hub including an anti-opening mark 180 degrees out of alignment with the central circumferentially position of the side opening in the cannula active tip; the electrode curve and the cannula side opening being configured such that when the electrode is advanced sufficiently far through the cannula hub and into the cannula lumen with the electrode curve mark aligned with the cannula opening mark, the tissue-piercing end of the electrode shaft emerges from the side opening; and the electrode curve and the cannula side opening being configured such that when the electrode is advanced sufficiently far through the cannula hub and into the cannula lumen with the electrode curve mark aligned with the cannula anti-opening mark, the tissue-piercing end of the electrode shaft extends to the tissue-piercing end of the cannula shaft within the cannula shaft lumen.

FIG. 12B is a schematic diagram showing an assembly of electrode and the cannula of FIG. 12A wherein the cannula is inserted into bodily tissue; the electrode is fully inserted through the cannula hub into the cannula lumen with the electrode curve mark aligned with the cannula opening mark so that the tissue-piercing end of the electrode shaft extends from the side opening and into the bodily tissue; an RF generator generates an RF voltage between the electrode shaft and a ground pad placed on the surface of the bodily tissue; RF current flows through the bodily tissue from both the cannula active tip and the electrode shaft to the ground pad; and a monopolar RF heat lesion forms in the tissue surrounding the cannula active tip and the extension of the electrode shaft without the tissue.

FIG. 12C is a schematic diagram showing an assembly of electrode and the cannula of FIG. 12A wherein the cannula is inserted into bodily tissue; the electrode is fully inserted through the cannula hub into the cannula lumen with the electrode curve mark aligned with the cannula anti-opening mark so that the tissue-piercing end of the electrode shaft to the tissue-piercing end of the cannula shaft within the cannula shaft lumen; an RF generator generates an RF voltage between the electrode shaft and a ground pad placed on the surface of the bodily tissue; RF current flows through the bodily tissue from cannula active tip and the electrode shaft to the ground pad; and a monopolar RF heat lesion forms in the tissue surrounding the cannula active tip.

DETAILED DESCRIPTION OF THE INVENTION

Figure 1A:
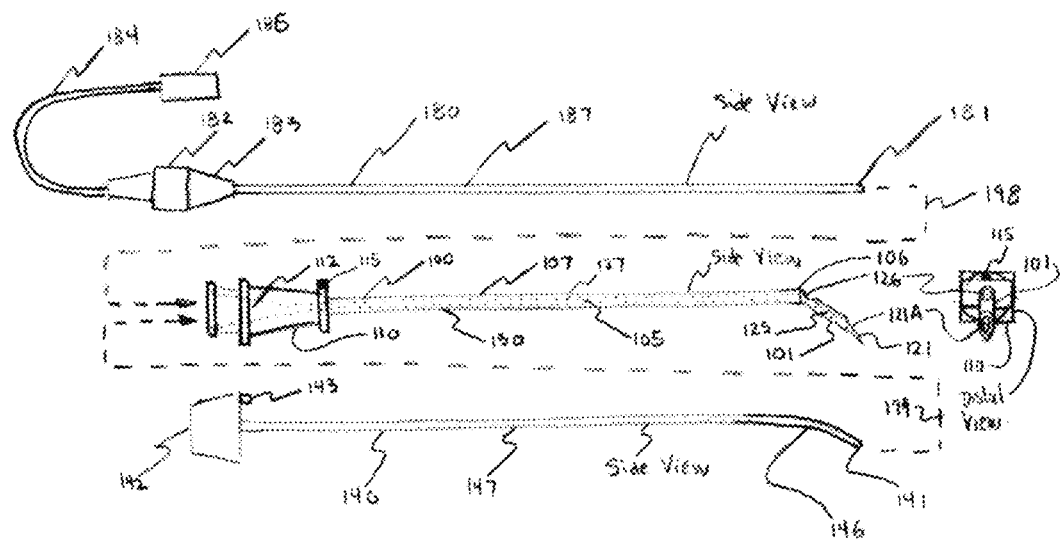
FIG. 1A is a schematic diagram showing an RF cannula and electrode system wherein the conductive shaft of the electrode is not shaped to define a bend, the cannula shaft includes a bend and a side opening to the cannula lumen which are both near the tissue-piercing end of the cannula shaft and are configured to provide for consistent passage of the electrode shaft out from the cannula lumen through the cannula opening when the electrode is fully inserted into the cannula lumen through the cannula hub.
Figure 1B:
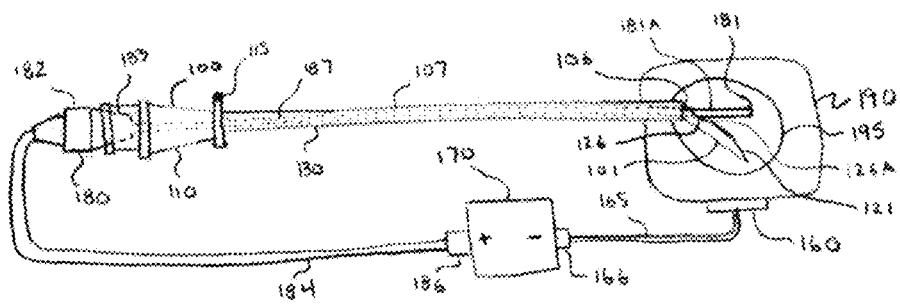
FIG. 1B is a schematic diagram showing the assembly of the RF cannula and RF electrode shown of FIG. 1A, wherein the cannula is inserted in bodily tissue, the electrode is fully inserted in the cannula, a portion of the electrode conductive shaft protrudes from the side opening of the cannula shaft, the electrode conductive shaft is energized by an RF generator whose reference connection is connected to a ground pad in contact with the bodily tissue, the electrode conductive shaft energizes the conductive active tip at the tissue-piercing end of the cannula shaft, and a radiofrequency heat lesion forms due to radiofrequency current flowing from both the cannula active tip and the portion of the electrode conductive shaft that protrudes from the side opening of the cannula shaft.
Figure 1C:
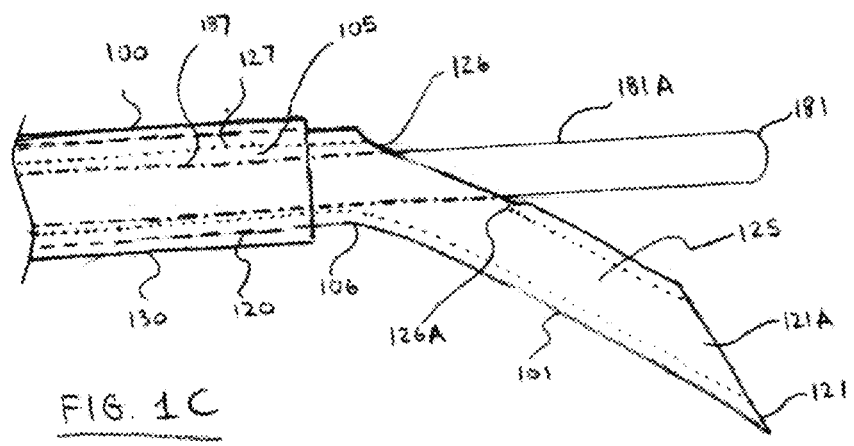
FIG. 1C is a schematic diagram showing a detail of the tissue-penetrating end of the assembly of the RF cannula and RF electrode shown in FIG. 1B, wherein the electrode passes out from the cannula lumen through the side opening without being deflected by the edges of side opening.

Referring now to FIG. 1, in accordance with several aspects of the present invention, FIG. 1 refers collectively to FIG. 1A, FIG. 1B, and FIG. 1C. FIG. 1 presents schematically several embodiments of a electrosurgical ablation probe system including a cannula 100 having an insulated shaft 130 and an active tip 101, and an electrode 180 that electrifies the cannula active tip 101 and consistently extends out from a side opening 126 near the cannula tissue-penetrating end 121 when the electrode shaft 187 is fully inserted into the cannula lumen 105 through the cannula hub 110. In one aspect, FIG. 1 relates to a cannula 100 having an active tip 101 and shaft bend 106, and an electrode 180 having a substantially straight shaft 187 that electrifies the cannula active tip 101 and extends from a side opening 126 near the cannula tissue-penetrating end 121, wherein the assembly of the electrode 180 and the cannula 100 generates a heat lesion around both the cannula active tip 101 and the portion of the electrode shaft 187 that extends out of the cannula side opening 126. In one aspect, FIG. 1 relates to a side-outlet RF ablation system that includes a standard thermocouple RF electrode, such as the Cosman TCN Nitinol-shaft electrode, used with an RF cannula having a side opening. In one aspect, FIG. 1 relates to the adaptation of an electrode having a straight, elastic shaft to effect a side-outlet ablation probe configuration. In one aspect, FIG. 1 relates to the adaptation of an electrode having a stiff, straight shaft to effect a side-outlet ablation probe configuration. In one aspect, FIG. 1 relates to the adaptation of a cooled-RF electrode having a stiff, straight shaft to effect a side-outlet ablation probe configuration.

FIG. 1 shows a medical probe system including an electrode 180, a cannula 100, and a stylet 140. The electrode includes an generator connector 186 configured to carry RF current from an RF generator to the electrode shaft 187 and to carry a temperature signal from the electrode temperature sensor 181 to the RF generator; a generator cable 184; a hub 182 at the electrode proximal, non-tissue-penetrating end, the hub having a male luer taper 183; an substantially straight, conductive metal shaft 187 configured to contact the inner surface of the cannula shaft 127 in order to conduct the RF current from the RF generator to the cannula active tip 101 when the electrode shaft 187 is inserted into the cannula lumen 105; a tip 181 including a temperature sensor at the distal, tissue-penetrating end of the shaft 187. The cannula 100 has a stiffer shaft 107 than does the electrode 180 and is configured to penetrate tissue, to provide a channel for insertion of the electrode 100 into tissue, and to provide an active tip 106 for delivering of RF current to bodily tissue from the electrode 180. The cannula 100 includes a hub 110 at the cannula proximal, non-tissue-penetrating end, the hub having a proximal female luer port 112 connected to the lumen 105 of the shaft 107 and sized to engage with the electrode male-luer hub taper 183; a shaft 107 composed of conductive metal hypodermic tubing 120 whose proximal end is covered by electrical insulation 130 and whose distal, tissue-penetrating end is uncovered to form a cannula active tip 101; a lumen 105 through the cannula shaft 107 sized to admit the electrode shaft 187; a sharp flat tissue-piercing bevel 121 at the distal end of the shaft, the bevel including an distal opening 121A to the cannula lumen 105; a shaft bend 106 oriented to the side of the shaft opposite from the side opening 126, the bend 106 and the side opening 126 being configured so that the electrode distal end 181 consistently exits the side opening 126 when the electrode shaft is fully inserted into the cannula lumen through the cannula hub port 112 such that the electrode hub luer 183 engages with the cannula hub luer 112, irrespective of the rotational orientation of the electrode 180 about the electrode longitudinal axis; a side opening 126 to the lumen 105 in the active tip 101; and a visual marker 115 on the hub 110 that is aligned with the side opening 126. The stylet 140 is configured to be inserted into the cannula 100 to stiffen the cannula shaft and/or to occlude the distal open 121A of the cannula shaft 107 during tissue penetration. The stylet 140 includes a cap 142 at the stylet proximal, non-tissue-penetrating end configured to engage with the cannula hub 110; an elongated shaft 147 configured to be inserted into the cannula lumen 105, having a bend 146, and having a tip 141 at the stylet distal, tissue-penetrating end, the tip being rounded to facilitate smooth sliding of the stylet shaft 147 through the cannula lumen 105; a tab 143 on the hub configured to engage with a slot in the cannula hub 110 only in an orientation that aligns the stylet shaft bend 146 with the cannula shaft bend 106 to ensure the stylet distal end 141 passes by the cannula side opening 126 and stays within the cannula lumen 105 distal to the side opening in order to align with the distal cannula bevel 121 when the stylet shaft 147 is fully inserted into the cannula lumen 105 such that the stylet cap 142 abuts the cannula hub 110. The electrode shaft 187 is not shaped to define a bend. In some embodiments, the electrode shaft 187 can be constructed from a substantially straight metal rod or tube that resists taking a bend during normal use of the electrode, such as a Nitinol rod or tube. In some embodiments, the electrode shaft 187 can be constructed from a stainless steel tube that is substantially straight. In some embodiments, the electrode shaft 187 can be constructed from a stainless steel tube has spring temper to resist taking a bend in normal use. In some embodiments, the electrode shaft 187 contains delicate internal structures, such as temperature-signal wires or internal-coolant tubing, that would be damaged by bending of the shaft. In some embodiments, the electrode shaft 187 can be substantially stiff (for example due to the electrode having a large diameter, being constructed from heavy tubing, containing numerous internal structures, containing numerous interneral structures for temperature monitoring and internal coolant flow) such that bending of the electrode shaft as the electrode 187 is advanced by a physician through a cannula during clinical use is not possible or practical; one of advantage of embodiments presented in FIG. 1 is that they provide a way to adapt such a substantially stiff electrode 187 for use in the a side-outlet ablation probe configuration. In some embodiments, the metal hypodermic tubing 120 can be stainless steel hypodermic tubing. The electrical insulation 130 can be a plastic coating or plastic tubing. The hub markers 115 can be a visual guide to the user for alignment of the stylet curve 146 with the cannula curve 106, and/or to indicate the orientation of the bend 106 when the cannula 100 inserted into bodily tissue. In some embodiments, the construction and dimensions of the electrode 180, the cannula 100, and stylet 140 can be typical of the electrodes, cannulae, and stylets used in existing RF ablation systems, such as the Cosman TCN electrode, Cosman CSK electrode, Cosman TCD electrode, Cosman CC cannula, and Cosman RFK cannula. In some embodiments, the size of the cannula tubing 120 can be a value selected from a value or range in the list: 22, 21, 20, 19, 18, 17, 16, 15, 14, 13 gauge, larger than 13 gauge, less than 22 gauge. The wall thickness of the cannula tubing 120 can be selected from regular wall, thin wall, heavy wall, and special wall-thicknesses. In some embodiments, the outer diameter of the electrode shaft 187 can be a value selected from a value or range in the list: 0.010" to 0.020", less than 0.010", greater than 0.020", 24 to 15 gauge, greater than 15 gauge, less than 24 gauge, a diameter less than the inner diameter of the cannula. In some embodiments, the length of the shaft 107 of the cannula 100 can be a value selected from a value or range in the list: 5, 6, 10, 12, 15, 20, 25, 30 cm, less than 5 cm, greater than 30 cm, 5-30 cm. In some embodiments, the length of the active tip 101 of the cannula 100 can have a value selected from a value or range in the list: 5, 10, 15, 20, 25, 30, 40, 50, 60 mm, less than 5 mm, 5-60 mm, greater than 60 mm. In some embodiments, the length of the electrode shaft extending distal to the side opening 181A have a value be selected from a value or range in the list: 5, 10, 15, 20, 25, 30, 40, 50, 60 mm, less than 5 mm, 5-60 mm, greater than 60 mm, equal to the length of the cannula active tip, less than the cannula active tip, greater than the cannula active tip. In some embodiments, the angle of the bend 106 can be a value selected from a value or range in the list: 5, 10, 15, 20, 25, 30 degrees, value between 5 and 30 degrees, a value less than 5 degrees, a value greater than 30 degrees, a value configured to ensure convex tissue heating around the cannula active tip 101 and the election shaft extension 181A out from the side opening 126. In some embodiments, each of the distance between the cannula point 121 and the side opening 126 and the distance between the cannula point 121 and the shaft bend 106 can be a value selected from among a value or range in the list: less than 5 mm, 5 to 10 mm, 10 mm to 20 mm, 20-50 mm, greater than 50 mm, equal to the length of the active tip 101, close to the length of the active tip. In some embodiments, the electrode male luer 183 and the cannula female luer 112 can take another interlocking or complementary form that allows for seating of the electrode hub 182 against the cannula hub 110.

Referring now to FIG. 1A, the electrode 180, the cannula 100, and the stylet 140 are shown separately in a side view. The cannula 100 is additionally shown in the distal view toward the tissue-penetrating end 121 of the cannula 100.

Referring now to FIG. 1B, the cannula 100 and electrode 180 are shown assembled and producing a monopolar RF heat lesion 195 in bodily tissue 190 by application of RF current to the tissue from both the cannula active tip 101 and a portion of the electrode shaft 181A extending from the side opening 126 of the cannula shaft 107. This configuration was produced by the process of inserting the cannula 100 into the bodily tissue 190 with the stylet 140 fully inserted into the cannula lumen 105 via the cannula hub port 112, withdrawing the stylet 140 from the cannula lumen 105 from the cannula hub port 112; inserting the electrode 180 into the cannula lumen by way of the cannula hub port 112 without regard for the rotational orientation of the electrode about the longitudinal axis of the cannula shaft 107 or relative to the position of the side opening 126; connecting an RF generator 170 to the electrode and to a ground pad 160 placed on the surface of the bodily tissue 190; delivering RF current from the RF generator 170 to the electrode 180; and controlling the RF current output of the RF generator using the temperature indicated by the electrode temperature sensor 181 and measured by the RF generator 170. In some embodiments, the temperature sensor 181 can be omitted, and the control of the RF current can be performed without a temperature measurement. The said process is one example of a process for generating a heat lesion that has a larger extent to one side of a cannula active tip using an electrode not having a predetermined bend. The said process is one example of a process for creating asymmetric heat lesion about a cannula active tip using a straight electrode. The said process is one example of a process for creating a larger heat lesion that would be created by a cannula having a side opening, using an electrode not having a defined curve.

In some embodiments, the electrode shaft 187 is too thin and flexible (for example 0.010" to 0.020") to easily pierce tissue to great depths (for example, deeper than 10 mm), so the electrode shaft 187, the cannula shaft 107, and the position of the side opening 126 can be positioned so that the electrode shaft portion 181A that extends from the side opening 126 has a length over which the electrode can reliably penetrate target tissue, such as muscles and connective tissue around the human spine. In some embodiments, the electrode shaft can have a blunt tip 181, however the outer diameter of the shaft 187 can be sized to be both fine enough to pierce target tissue, heavy enough to advance straight through the target tissue without being substantially deflected, and large enough to heat a substantial volume of tissue. In some embodiments, the tip 181 of the electrode can be sharpened to facilitate penetration of tissue.

In some embodiments, the length of the extension 181A of the electrode shaft 187, the length of the active tip 101, and the angle between the electrode shaft extension 181A and the cannula active tip 101 are configured so that the electrode shaft extension 181A and the cannula active tip 101 are close enough so that when the electrode shaft extension 181A and the cannula active tip 101 are brought to the same RF potential (as shown in FIG. 1B), a convex heat lesion 195 forms around both the electrode shaft extension 181A and the cannula active tip 101. In some embodiments, the length of the extension 181A of the electrode shaft 187, the length of the active tip 101, and the angle between the electrode shaft extension 181A and the cannula active tip 101 are configured so that when the electrode shaft extension 181A and the cannula active tip 101 are brought to the same RF potential, a non-convex heat lesion 195 forms around both the electrode shaft extension 181A and the cannula active tip 101.

The cannula 100 is inserted into bodily tissue 190, the electrode 180 is fully inserted into the cannula 100 such that the electrode hub taper 183 engages with the cannula hub port 112, a portion of the electrode shaft 181A extends from the side opening 126 of the cannula active tip 101, a ground pad 160 is applied to the surface of the bodily tissue 190 connected to the reference jack labeled "−" of an RF generator 170 via connection 166, electrode is connected to the electrode jack labeled "+" of the RF generator 160 via generator connection 186, a temperature signal form the electrode temperature sensor 181 is conducted to the RF generator 170 for control and/or display, RF current flows from the RF generator to the conductive electrode shaft 187 via the connection 186, to the cannula shaft 120 by contact between the electrode shaft 187 and the conductive inner surface 127 of the cannula shaft 120, to the tissue from both the cannula active tip 101 and the portion 181A of the electrode shaft 187 extending from the cannula side opening 126 into the tissue 190, and returning to the RF generator 170 via the ground pad 160. By ohmic heating, the RF current within the bodily tissue causes the tissue temperature to increase around both the cannula active tip 101 and the portion 181A of the electrode shaft 187 extending from the cannula side opening 126.

Referring now to FIG. 1C, a detail of the distal end of the assembly of the cannula 100 and electrode 180. The cannula shaft bend 106 and the cannula side opening 126 are dimensioned and positioned so that the straight electrode shaft 187 always exits the cannula lumen 105 directly out of the side opening 126 when the electrode 180 is advanced proximal to distal through the cannula shaft 107, without any deflection of the electrode shaft 187, and irrespective of rotational orientation of the electrode 180 relative to the cannula shaft 107. The electrode shaft 187 not being shaped to define a bend, the electrode shaft 187 is substantially axially symmetric, and changes in the rotational orientation of the electrode shaft 187 about its long axis (which is parallel to the long axis of the cannula shaft 107 when the electrode is inserted into the cannula lumen 105) cannot be used to direct the tip of the electrode shaft 181 to different branches of the cannula lumen, ie the opening 126 and distal lumen 125. In some embodiments, depending on the interface between the electrode tip 181 and tissue and variations in the construction of the electrode 180 and cannula 180, the electrode shaft may deflect off the distal edge 126A of the side opening 126 in the wall of the cannula tube 120 to consistently extend out of the side opening 126. The electrode shaft can be constructed from nitinol memory metal or spring temper stainless steel to ensure the electrode 181 does not enter the distal portion 125 of the cannula lumen 105 between the side opening 126 and distal point 121 of the cannula 100. The portion of the electrode shaft 187 within the cannula lumen 105 is shown as a dash-dot line. The inner surface 127 of the cannula shaft tube 120 is shown as a dotted line. The outer surface of the cannula shaft tube 120 is shown as a dashed line under the insulation 130. The cannula bevel 121 includes an end opening 121A to the cannula lumen 105. In some embodiments the end opening 121A be closed to form a solid flat bevel to facilitate insertion of the cannula 100 into bodily tissue without the use of a stylet 140.

The electrical insulation 130 is a tubular structure that is electrically insulative at electrical signal frequencies intended to be delivered deliver to bodily tissue via the probe 100. In some embodiments, said signal frequencies can include radiofrequency signal frequencies, microwave (MW) signal frequencies, the signal frequencies associated with nerve stimulation signals, the signal frequencies associated with muscle stimulation signals, high frequency signal frequencies, low frequency signal frequencies and other signal frequencies applied via probes and other electrodes to bodily tissue. The insulation 130 can have a high dielectric constant. The dielectric breakdown (also known as the dielectric strength) of the insulation 130 can be greater than 500 V/m. The electrical insulation 130 can have a wall thickness that is a value selected from a value or range of value in the list: a value in the range 0.00025 to 0.005 inches, a value less than 0.00025 inches, a value greater than 0.005 inches. The electrical insulation can have wall thickness in the range 0.001 to 0.002 inches. The electrical insulation 130 can have wall thickness configured to suit clinical needs, mechanical constraints, and/or electrical requirements. The insulation 130 can be composed of a material known the art of medical device design, such as PTFE, FEP, PET, polyolefin, polyurethane, polyimide, nylon, and other materials for medical tubing. The insulation 130 can be heat-shrinkable tubing, such as PTFE, FEP, PET, polyolefin, and other materials known in the art of medical device coating, such as needle, wire, guidewire, and coil coating. The insulation 130 can be tapered and/or adhered to the shaft 120 at the distal end of the insulation. In some embodiments, the electrical insulation 130 can be an electrically-insulative coating, such as a coating that can be painted or sprayed onto the cannula shaft tube 120, such as an elastomeric coating, powered paint, fluid paint, or another kind of paint.

In some embodiments, the cannula shaft point 121 have a geometry selected from the list: closed distal end, blunt tip, solid trocar tip, tuohy, crawford, hustead, weiss, sprotte spezial, epidural-type tip, tip configured for passage of a catheter, tip configured for introduction of an epidural catheter, square tip, square tip with tapered sharpened distal edge, non-coring tip, spinal needle tip, quincke, sise tip, kirschner, lemmon, whitacre, crawford tip, lutz, hanaoka, sprotte, courand, seldinger, franseen, chiba, tip matched to the stylet tip 141 geometry, and other medical needle tip geometries. In these embodiments, the stylet 141 can have one of a variety of geometries matched to the cannula shaft bevel 121 in order to serve a functional need, such as forming a substantially solid distal needle point that facilitate penetration of bodily tissue with minimal coring. In some examples, the shaft tip 121 and stylet bevel 141 can be configured to provide for penetration into bone, such as vertebral bone or any bone in the body, for access to nerve within bone, osteoid osteoma, bone tumors, or another intra-bone structures. In some embodiments, the stylet shaft 147 can have a length sized to extend beyond the distal end 121 of the needle shaft 120. In some embodiments, the cannula 100 and electrode 180 can be configured to be placed in a specific part of the body such as the spine, a blood vessel, the epidural space, the spinal cord, a visceral organ, the liver, the kidney, the pancreas, the lung, the brain, a gland, the tyroid, the adrenal gland, a bone, a vertebral bone.

Figure 2:
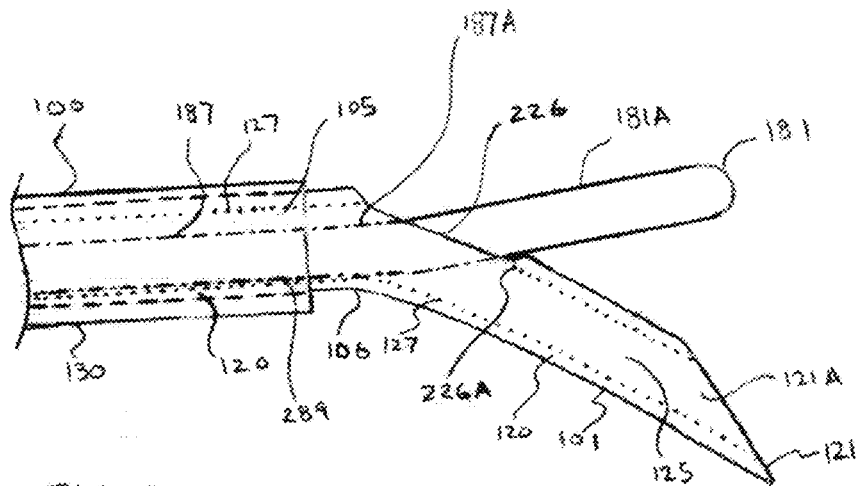
FIG. 2 is a schematic diagram showing the assembly a straight RF electrode and a curved RF cannula wherein the electrode tip exits the cannula lumen though a side hole in the cannula active tip near the cannula tissue-penetrating end, the electrode tip is deflected lateral to the cannula active tip by an edge of the side hole, and the curve and side hole of the cannula shaft are configured so that the electrode tip always exits the cannula lumen through the side hole when the electrode shaft is fully inserted into non-tissue-piercing end of the cannula shaft.

Referring now to FIG. 2, in accordance with several aspects of the present invention, FIG. 2 presents schematically several embodiments of the electrosurgical ablation probe system including cannula 100 and electrode 180 as described in FIG. 1, wherein cannula side opening 126 is replaced by cannula side opening 226. Cannula side opening 226 is positioned so that the electrode shaft 187 is deflected away from the cannula tip when it exits the lumen 105 of cannula 100 by physical contact between the electrode shaft 187 and the distal edge 226A of the side opening 226. As in FIG. 1, the electrode tip 181 always exits the side opening 226 when the electrode 180 is inserted into the cannula 100 via the cannula hub 110, for all rotational orientations of the electrode 180 relative to the longitudinal axis of the cannula shaft 107 and the position of the side opening 226.

Figure 3:
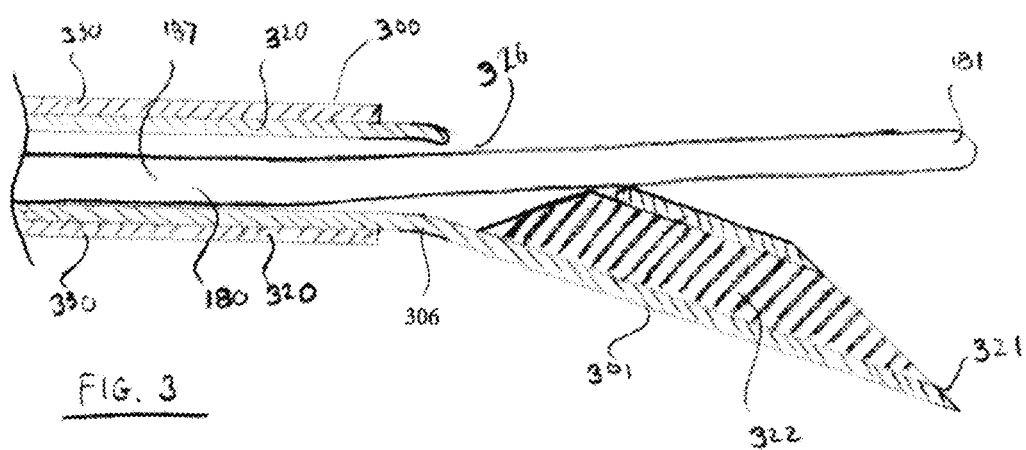
FIG. 3 is a schematic diagram showing the assembly of a straight RF electrode and a curve-tip RF cannula wherein the electrode tissue-penetrating end extends out of the cannula lumen through an opening in the side of the cannula active tip at the cannula tissue-penetrating end, wherein the bevel of the cannula tissue-penetrating end is closed, and wherein the electrode extends out of the cannula lumen through the said opening when the cannula is inserted into bodily tissue and the electrode is fully inserted into the lumen at the non-tissue-penetrating end of the cannula.

Referring now to FIG. 3, in accordance with several aspects of the present invention, FIG. 3 presents schematically, in a cross-sectional view, several embodiments of the electrosurgical ablation probe system including cannula 100 and electrode 180 as described in FIG. 1, wherein cannula 100 is replaced by RF cannula 300, which differs from cannula 100 in that the lumen distal to the side opening is closed off in cannula 300, whereas it is open in cannula 100 (see element 125). The closure 322 of the distal lumen of cannula 300 provides a ramp-like surface that moderately deflects the tip of electrode 181 out of the side opening 325 of cannula 300. The electrode 180 can only extend from the side opening 326 of the cannula and cannot enter the distal lumen within the cannula active tip 301. The geometry of the side opening, the closure 322, the shaft bend 306, the flexibility and geometry of the electrode shaft 187 can be adjust to create a desired amount of deflection of the electrode tip 181 away from the cannula active tip 301. In some embodiments, the bend 306, opening 326, and closure 322 can be adapted so that the electrode shaft 187 exits the side opening 326 without any deflection; this can be useful for an electrode shaft 187 that is too stiff to be deflected, such as a heavy cooled RF electrode shaft. In some embodiments, the closure 322 can be selected from the list: glue, a plug, an integral closure of the shaft tubing 320, a weld of the shaft tubing 320. The closure 322 forms a solid bevel surface 321 at the distal, tissue-piercing end of the cannula. RF cannula 300 includes a hub, conductive shaft tubing 320 having a bend 306 near the distal tissue-piercing end of the cannula 300, electrical insulation 330 covering the proximal portion of the shaft to produce a conductive active tip 301, a closure 322 of the cannula distal end, and sharp tissue piercing tip 321. In some embodiments, the bend 306 can be omitted and the cannula shaft can be substantially straight over the entirety of its length.

Figure 4A:
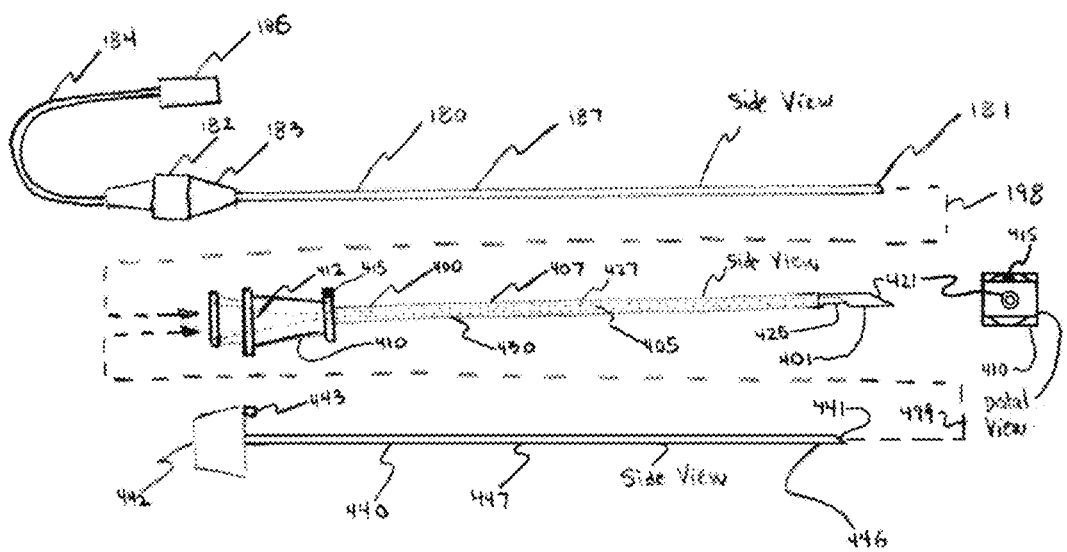
FIG. 4A is a schematic diagram showing an electrosurgical system including an electrode and a cannula, wherein the electrode includes an electrically-conductive, elastic, substantially straight shaft; the cannula includes a substantially straight shaft having an electrically conductive active tip and sharpened point at its tissue-penetrating end, and being electrically insulated over the remainder of the cannula shaft; the cannula includes a lumen extending from its non-tissue-penetrating hub to its active tip, and exiting the cannula shaft from the side of the active tip such that the cannula tissue-penetrating end is closed and form a ramp configured to provide for smooth exit and protrusion of the electrode shaft when a sufficient length of the electrode shaft is inserted into the lumen of the cannula through the cannula hub.
Figure 4B:
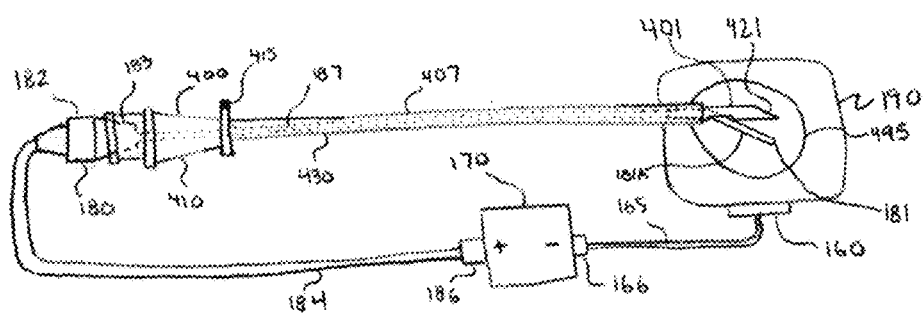
FIG. 4B is a schematic diagram showing the assembly of the electrode and the cannula of FIG. 4A where the cannula is inserted into bodily tissue, the electrode is inserted into the cannula, radiofrequency current is delivered to the electrode, and the radiofrequency current flows into the tissue from both the cannula active tip and the portion of the electrode shaft that protrudes from the side of the cannula active tip.
Figure 4C:
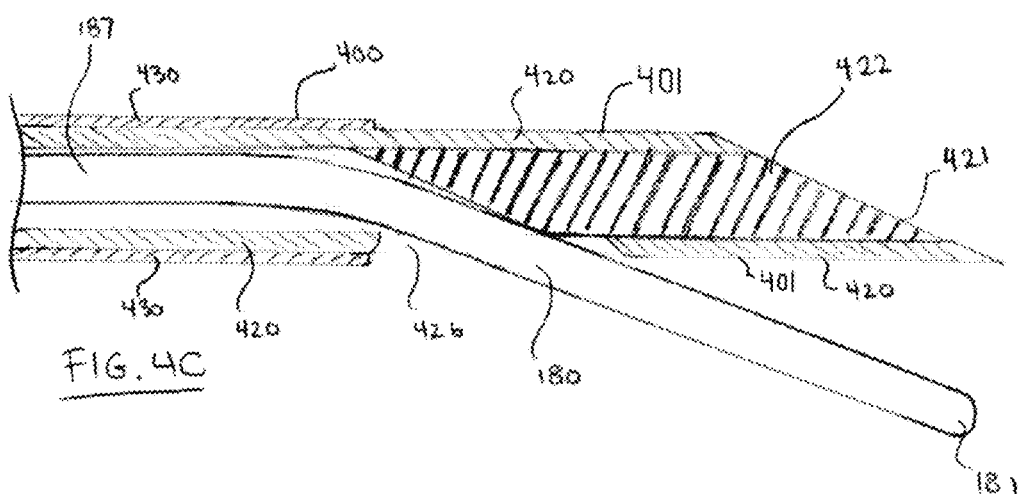
FIG. 4C is a schematic diagram showing a cross-sectional detail of the tissue-penetrating end of the assembly of FIG. 4B, wherein the electrode shaft has been deflected and directed out of the cannula lumen to the side of the cannula active tip.

Referring now to FIG. 4, in accordance with several aspects of the present invention, FIG. 4 refers collectively to FIG. 4A, FIG. 4B, and FIG. 4C. FIG. 4 presents schematically several embodiments of a electrosurgical ablation probe system including a cannula 400 having an insulated shaft 430 and an active tip 401, and an electrode 180 which electrifies the cannula active tip 401 and whose distal tip 187 consistently extends out from a side opening 426 near the cannula tissue-penetrating end 421 when the electrode shaft 187 is fully inserted into the cannula lumen 105 through the cannula hub 110. In one aspect, FIG. 4 relates to a cannula 400 having substantially straight shaft 407 and active tip 401, and an electrode 180 having a substantially straight and elastic shaft 187 that electrifies the cannula active tip 401 and extends from a side opening 426 near the cannula tissue-penetrating end 421, wherein the assembly of the electrode 180 and the cannula 400 can be used to generate an asymmetrical heat lesion around both the cannula active tip 401 and the portion of the electrode shaft 187 that extends out of the cannula side opening 426. In one aspect, FIG. 4 relates to a side-outlet RF ablation system that includes a standard thermocouple RF electrode, such as the Cosman TCN Nitinol-shaft electrode, used with an RF cannula having a side opening. In one aspect, FIG. 4 relates to the adaptation of an electrode having a straight, elastic shaft to effect a side-outlet ablation probe configuration. In one aspect, FIG. 4 relates to the adaptation of an internally-cooled RF electrode having an elastic shaft to effect a side-outlet ablation probe configuration.

The cannula 400 has similar features to those of the cannula 100 but includes the modiciations: the shaft 407 is straight over its entire length, the distal bevel 411 does not have an opening to the cannula lumen 405, the cannula 400 includes an internal structure 422 that directs the electrode 180 out of the side opening 426 when the electrode 180 is inserted into the cannula lumen 405 through the port 412 of the cannula hub 410. The stylet 440 has similar features those of the stylet 140 but includes the modifications: the shaft 447 does not have a bend, and the shaft 447 of the stylet 440 does not extend through the entirety of the cannula shaft 407, but rather stops at the closure 422 at the distal end of the cannula 400. The cannula includes hub 410 at the cannula proximal non-tissue-penetrating end of the cannula 400, hub port 412, shaft 407 consisting of metal tube 420 covered by electrical insulation 430, active tip region 401, side opening 401, lumen 405, hub marker 415, shaft tube inner surface 427, shaft bevel 421 at the distal tissue-piercing end of the cannula 400. The sytlet 440 include cap 442, indexing tab 443, straight shaft 447, distal bevel 441.

Referring now to FIG. 4A, the electrode 180, cannula 400, and stylet 440 are shown separately in a side view. The cannula 400 is additionally shown in a distal view oriented toward the distal, tissue-penetrating tip 421 of the cannula 400. The hub marker 415 is positioned 180 degrees opposite the side opening 426 in the cannula shaft 407. In some embodiments, the hub marker 415 can be aligned rotationally with the side opening 426.

Referring now to FIG. 4B, the electrode 180 and cannula 400 are assembled with the cannula having been inserted into bodily tissue 190, connected operably to an RF generator 170 and a ground pad 160, and used to create a monopolar RF heat lesion 495 within the bodily tissue. The configuration was produced by first inserting the cannula 400 into the tissue 190 with the sylet 440 in place within the cannula lumen 405, replacing the stylet 440 with the electrode 180, and energizing the electrode 180 and cannula 400 by the RF generator 170. The heat lesion 495 is asymmetric about the longitudinal axis of the cannula shaft 407 due to the extension of the electrode shaft 187 into the tissue 190. Using the electrode 180 and cannula 400, a physician can bias the location of a heat lesion to a side of the cannula shaft 407 by rotation of the cannula 400 about its longitudinal, proximal-distal axis when the electrode is withdrawn into the cannula lumen 405, or not inserted into the cannula 400 at all. The volume of the heat lesion 495 can generally be larger than then volume of the heat lesion that would be produced if the electrode shaft 187 were positioned inside the cannula active tip 401 with the electrode temperature sensor 181 aligned with the distal point 421 due to the increased surface area and spatial extent of the combined active tip comprising the extension 181A of the electrode shaft 187 into the tissue 190 and the cannula active tip 401 itself.

Referring now to FIG. 4C, a cross-sectional detail of the detail tissue-penetrating end of the assembled electrode 180 and cannula 400 is shown. In some embodiments, the cannula 400 can be the cannula 300 with the shaft bend 306 omitted. The closure 422 at the distal end of the cannula 400 consistently directs the electrode tip 181 out of the side opening 426 when the electrode 180 is fully inserted into the cannula lumen 405 via the port 412 in the cannula hub 410.

Figure 5A:
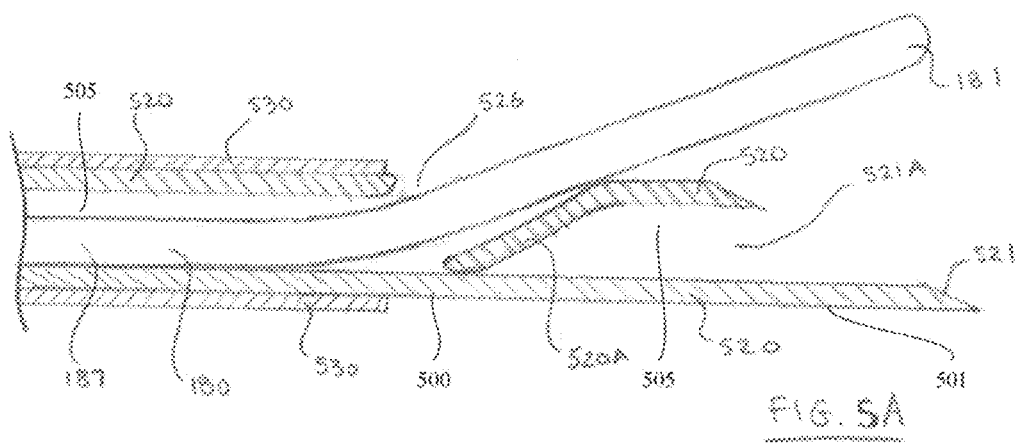
FIG. 5A is a schematic diagram showing a cross-section detail of the tissue-penetrating end of an radiofrequency ablation probe system including an RF cannula and an RF electrode wherein the electrode shaft is electrically conductive and is substantially straight when not subjected to substantial external forces; the cannula shaft is substantially straight, is formed form electrically-conductive metal tubing, and is covered by electrical insulation except for an uninsulated active tip portion at the shaft tissue-penetrating end; the cannula active tip includes a side opening to the cannula lumen within the cannula tubing, the side opening being formed by a deflection of a flap of the side wall of the cannula shaft tubing into the cannula lumen; when the electrode is inserted into the cannula lumen at its non-tissue-penetrating end, the electrode tip is deflected by the flap out of the opening; and the electrode shaft conducts a radiofrequency ablation signal to the cannula active tip.
Figure 5B:
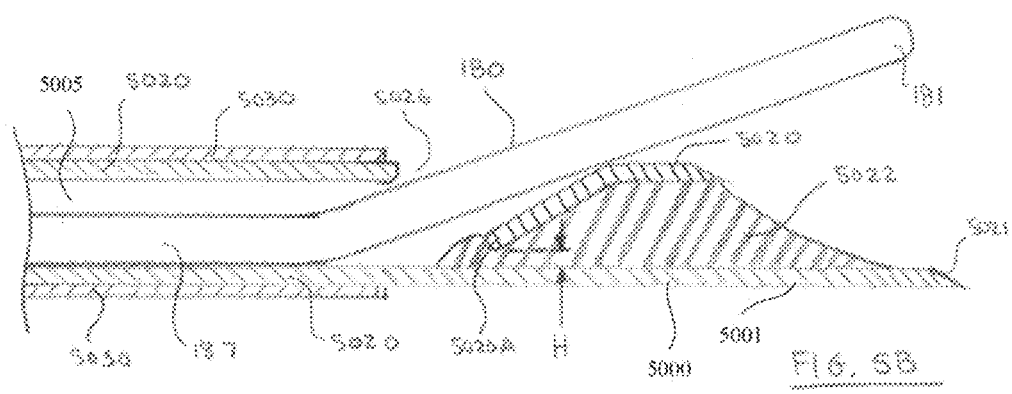
FIG. 5B is a schematic diagram showing a cross-section detail of the tissue-penetrating end of an RF lesioning system comprising an electrode that slides through a cannula lumen wherein the electrode includes an elongated metal shaft having a proximal non-tissue-penetrating end and a distal tissue-penetrating end; the cannula shaft has a distal tissue-piercing end and a proximal non-tissue-piercing end; the cannula shaft includes metal hypodermic tubing whose proximal end is covered by electrical insulation, whose distal end is uninsulated to form an active tip, and whose distal end is sharpened into a flat bevel; the active tip includes a side opening to the cannua lumen formed by bending a flap of the metal hypodermic tubing of the cannula shaft into the cannula lumen; the cannula lumen distal to the flap is filled to close the distal end of the cannula shaft; the flap deflects the electrode distal end out of the cannula side opening when the cannula is positioned in bodily tissue and the electrode shaft is inserted into the proximal end of the cannula lumen; and a radiofrequency signal conducted to the electrode shaft is also conducted to the cannula active tip via the physical contact between the cannula metal tubing and the electrode metal shaft.

Referring now to FIG. 5, in accordance with several aspects of the present invention, FIG. 5 refers collectively to FIG. 5A and FIG. 5B. FIG. 5 presents schematically several embodiments of a electrosurgical ablation probe system of alternative constructions of the cannula 400 presented FIG. 4, wherein electrode 180 is directed out of the side opening in a straight cannula shaft by means of a flap of the wall of the cannula shaft at the distal aspect of the side opening.

Referring now to FIG. 5A, an assembly of the electrode 180 and a straight RF cannula 500 having a side outlet 526 is shown in a cross-sectional view of the tissue-penetrating end of the assembly. The cannula 500 generally has features similar to that of cannula 400 with modification of the construction of the side opening and distal end of the cannula. The cannula 500 includes a metal tubular shaft 520 whose proximal, non-tissue-penetrating end is covered by electrical insulation 530, leaving an active tip 501 at the cannula distal end formed from the uncovered portion of the tube 520. The shaft tube 520 has a sharp flat bevel 521 at its distal tissue-penetrating end, the bevel 521 including an opening 521A to the cannula lumen 505. The side opening 526 is formed by a flap 520A of the wall of the tube 520 that is deflected into the cannula lumen 505 to the opposite wall of the cannula shaft tube 520. When the straight-shaft electrode 180 is fully inserted into cannula 500, the electrode shaft tip 181 always exits the side opening 526, irrespective of the rotational alignment of the electrode shaft 187 within the cannula lumen 505, as long as solid tissue positioned at the side opening 526 does not prevent the exit. The flap 520A does not create a fluid-tight seal between the end opening 521A and the proximal part of the cannula lumen, so fluids injected through the cannula lumen are dispersed both into tissue lateral to the side outlet 526 and distal to the cannula tip 521; this is an advantage of this cannula construction which provides both for consistent extension of the electrode tip 181 from the cannula side outlet 526 and a fluid injection both distal to and to the side of the cannula active tip 501. In some embodiments, the flap 520A is not deflected entirely across the cannula lumen 505, but rather substantially across the cannula lumen 505 so that the inserted electrode 180 always exits the side outlet 526 and never enters the lumen 505 between the side opening 526 and the end opening 521A. In some embodiments, the flap can be an inward bump or dent into the cannula lumen.

Referring now to FIG. 5B, an assembly of the electrode 180 and a straight RF cannula 5000 having a side outlet 5026 is shown in a cross-sectional view of the tissue-penetrating end of the assembly. The cannula 5000 generally has features similar to that of cannula 400 with modification of the construction of the side opening and distal end of the cannula. The cannula 5000 generally has features similar to that of cannula 4500 with modification that the distal opening in the bevel 5021 of cannula 5000 is closed by structure 5022. The cannula 5000 includes a metal tubular shaft 5020 whose proximal, non-tissue-penetrating end is covered by electrical insulation 5030, leaving an active tip 5001 at the cannula distal end formed from the uncovered portion of the tube 5020. The shaft tube 5200 has a sharp flat bevel 5021 at its distal tissue-penetrating end. The side opening 5026 is formed by a flap 5020A of the wall of the tube 5020 that is deflected into the cannula lumen 5005 toward the opposite wall of the cannula shaft tube 520. The distance H between the flap 5020A and the inner wall of the cannula tube 5020 is greater than zero (though in some other embodiments of cannula 5000 H can equal zero). The cannula lumen between the flap 5020A and the distal bevel 5021 is filled with solid glue 5022. The glue fills the gap between the flap 5020A and the inner wall of the cannula shaft tube 5020 to close the distal end of the cannula 5021 and to provide for smooth deflection of the inserted shaft 187 of the electrode 180 toward and out of the side port 5026. When the straight-shaft electrode 180 is fully inserted into cannula 5000, the electrode shaft tip 181 always exits the side opening 5026, irrespective of the rotational alignment of the electrode shaft 187 within the cannula lumen 5005. The flap 5020A and glue 5022 create a fluid tissue seal so that fluid injected through the cannula lumen 5005 is directed to tissue at the side of the cannula active tip 5001 into which an inserted electrode shaft 187 extends. The closure 5022 of the cannula distal end 5021 creates a solid bevel tip that reduces tissue coring as the cannula penetrates solid tissue. In some embodiments, the flap 5020A is deflected entirely across the cannula lumen 5005. Injection of glue 5022 distal and proximal to the flap 5020A creates a mechanical lock that prevent dislodgement of the glue plug 5022.

Figure 6A:
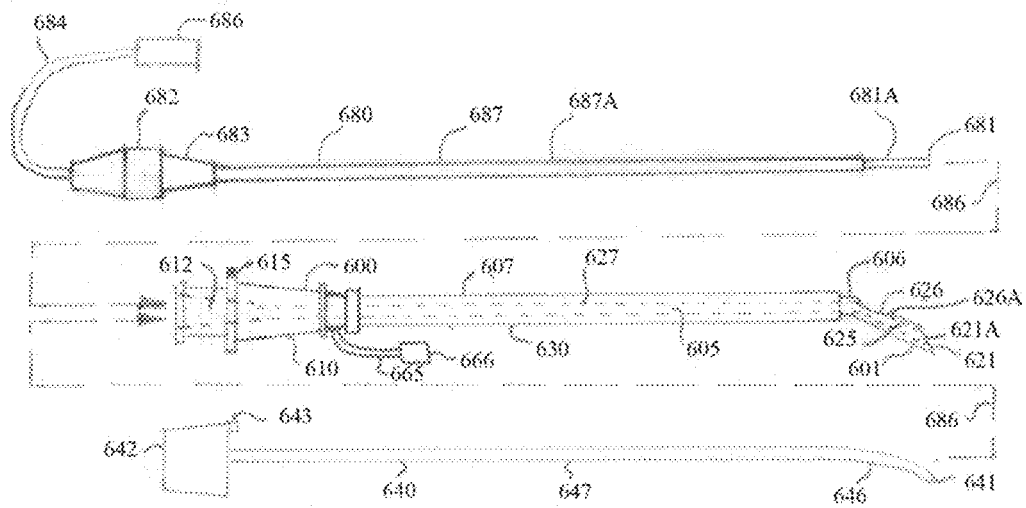
FIG. 6A is a schematic diagram showing a two-piece bipolar RF ablation probe system including a cannula and an electrode each having a distal tissue-penetrating end and a proximal non-tissue-penetrating end, wherein the electrode shaft is electrically insulative over its proximal length and has a conductive active tip at its distal end; the electrode shaft does not have a predetermined bend; the cannula includes a lumen through its proximal hub and shaft; the cannula shaft is electrically insulative over its proximal length and has a conductive active tip at its distal end; the cannula shaft includes a bend and a side opening to the cannula lumen configured so that the electrode shaft always exits the cannula side opening when the electrode shaft is fully inserted into the cannula lumen via the cannula hub; the electrode active tip and cannula active tip are electrically isolated when the electrode is fully inserted into the cannula lumen via the cannula hub; the electrode includes an electrode connection to an electrosurgical generator by means of which the electrode active tip can be electrified; the cannula includes a cannula connection to an electrosurgical generator by means of which the cannula active tip can be electrified
Figure 6B:
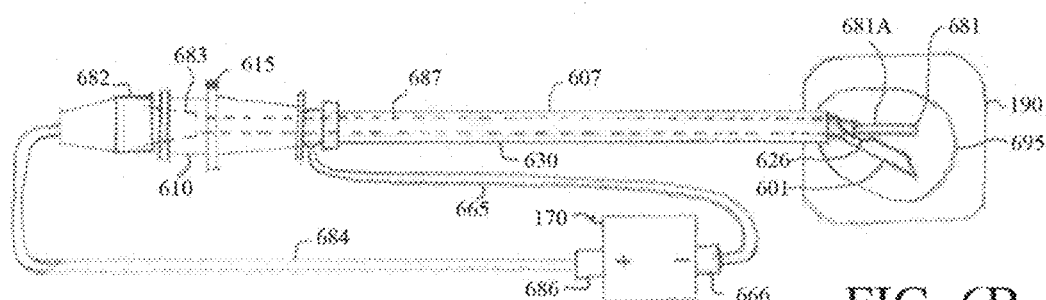
FIG. 6B is a schematic diagram showing the system of FIG. 6A wherein the cannula has been inserted into bodily tissue, the electrode has been fully inserted into the cannula lumen via the cannula hub and extends into the bodily tissue via the side opening in the cannula shaft, the electrode active tip is connected to a first output jack of RF generator, the cannula active tip is connection to a second output jack of an RF generator, RF current from the RF generator flows through the bodily tissue from the electrode active tip to the cannula active tip thereby forming an RF heat lesion in the bodily tissue.

Referring now to FIG. 6, in accordance with several aspects of the present invention, FIG. 6 refers collectively to FIG. 6A and FIG. 6B. FIG. 6 presents schematically several embodiments of a bipolar RF heating lesioning system including an electrode 680, stylet 640, and a cannula 600; the electrode 680 including a generator connection 686 and a substantially straight shaft 687, the shaft 687 including an electrically-insulated proximal portion 687A and an electrically conductive distal electrode active tip portion 681A, the generator connection 686 and cable 684 carrying an RF signal from an RF generator 170 to the electrode active tip 681A and a temperature signal from a temperature sensor in the electrode distal point 681 to the RF generator; the cannula 600 into whose lumen 605 the electrode 680 is configured to be inserted includes an electrically-insulated shaft 607 having a conductive active tip 601, an generator connection 666 that conducts an RF signal from an RF generator to the cannula active tip 601, a bend 606 near the cannula active tip, a side opening 626 out of which the electrode tip 681 extends when the electrode 680 is fully inserted into the cannula lumen via the port 612 in the cannula hub at the proximal end of the cannula, a sharpened distal bevel 621 including an distal opening 621A to the cannula lumen 605, and a hub marker circumferentially aligned with the side opening 626; the stylet 640 having a curved shaft 647 wherein the shaft curve is configured to allow the stylet shaft 647 to enter the distal lumen 625 of the cannula shaft 607 within the cannula active tip and thereby occlude the opening 621A in the cannula distal bevel 621. The electrode 680 has similar features to the electrode 180 with the exception that the electrode shaft 687 is partially covered by electrical insulation 687A, so that the electrode active tip 681A is only a portion of the shaft 687, rather than being the entire shaft 187 in electrode 180. The cannula 600 has similar features to the cannula 100 with the exception that the cannula 600 includes a generator connection 666 that conducts an RF potential to the conductive tubing forming the cannula shaft 607 and thus to the cannula active tip 601, which is a part of said conductive tubing. The electrode 680 and the cannula are configured such that when the electrode 680 is fully inserted into the cannula 600 such that the electrode hub 682 and the cannula hub 610 engage, the electrode active tip 681A and a distal portion of the electrode shaft insulation 687A extend out from cannula side opening 626; the electrode active tip 681A and the cannula active tip 601 are physically and electrically separated; there is no path for substantial conduction of electrical current from the electrode active tip 681A and the cannula active tip 601 within the assembly of the electrode 680 and cannula 600; the cannula active tip 601 can be connected to one output pole of an RF generator by connection 666 and the electrode active tip 681A can be connection to the opposite output pole of an RF generator by connection 686, in order to create a bipolar RF heat lesion in tissue in which both the electrode active tip 681A and the cannula active tip 601 are inserted. In some embodiments, the entirety of the electrode hub 682 and the entirely of the cannula hub 610 are composed of electrically-insulating materials to prevent conduction between the electrode active tip 681A and the cannula active tip 601 within the assembly of the electrode 680 and the cannula 600. In some embodiments, only the interfacing surfaces of the electrode hub 683 and the cannula hub 612 are electrically insulative. The bend in the cannula shaft 606, the side opening 626, and electrode shaft 687 are configured such that the distal end of the electrode 681 will consistently exit the cannula lumen 605 via the side opening 626 and never enter the cannula lumen 625 between the side opening 626 and the cannula bevel 621.

Referring now to FIG. 6A, the electrode 680, cannula 600, and stylet 640 are shown separately from their sides.

Referring now to FIG. 6B, an assembly of the electrode 680 and the cannula 600 is operably connected to an RF generator 170 and a bipolar RF heat lesion is formed in the tissue 190 in which the cannula 600 and the electrode 680 are inserted. The cannula 600 is inserted into the tissue first, and then the electrode 680 is inserted into the cannula 600 to produce this configuration. The electrode active tip 681A is connected to the "+" pole of the RF generator 170, and the cannula active tip 601 is connected to the "−" pole of the RF generator 170 by connections 686 and 666, respectively. Electrical insulation 687A along the electrode shaft electrically isolates the electrode shaft 687 from the inner surface of the conductive tubing 620 forming the cannula shaft 607 In some embodiments the electrode shaft insulation 687A can extend farther distally and/or the bend angle 606 can be increased to increase the physical separation between the electrode active tip 681A and the cannula active tip 601 to prevent short circuiting of RF current between the active tips 681A and 601 and/or produce a bipolar lesion that surround a greater portion of the active tip 681A and 601.

Figure 7A:
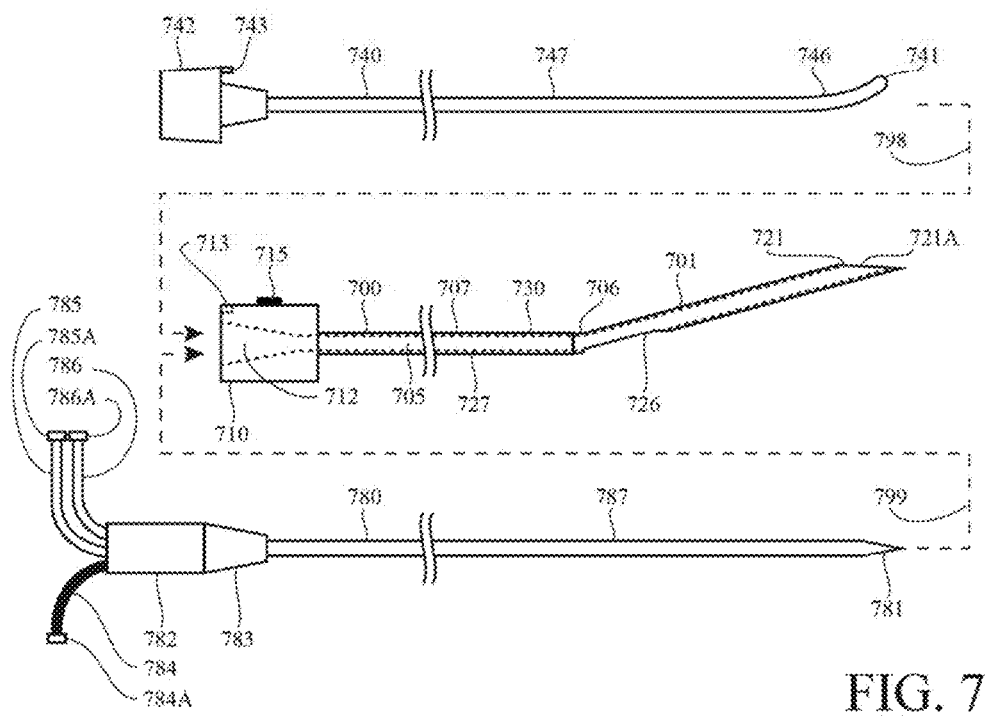
FIG. 7A is a schematic diagram showing a cooled RF electrosurgical system including an internally-cooled RF electrode, an RF cannula, and a stylet for the RF cannula, wherein the electrode shaft is substantially straight and electrically-conductive; the electrode includes an inflow port and an outflow port through which a fluid can be circulated within the electrode shaft; the electrode includes a generator connection by which the electrode shaft can be electrified by an RF generator; the cannula includes a hub at a first end of the cannula shaft through which the electrode shaft can be inserted into the cannula shaft lumen; the cannula shaft includes an electrically-conductive tube of which the portion attached to the cannula hub is covered by electrical insulation and of which the active tip portion at the second end of the cannula shaft opposite the first end is not covered by electrical insulation; the electrically-conductive electrode shaft contacts the electrically-conductive cannula tube when the electrode is inserted into the tube via the cannula hub; the cannula active tip portion includes a curve, a side opening to the cannula shaft lumen, and a sharpened distal bend configured to pierce tissue; the electrode shaft geometry, the cannula curve, and the cannula side opening are configured so that the electrode shaft consistently extends out of the cannula shaft lumen from the side opening when the electrode is inserted into cannula hub.
Figure 7B:
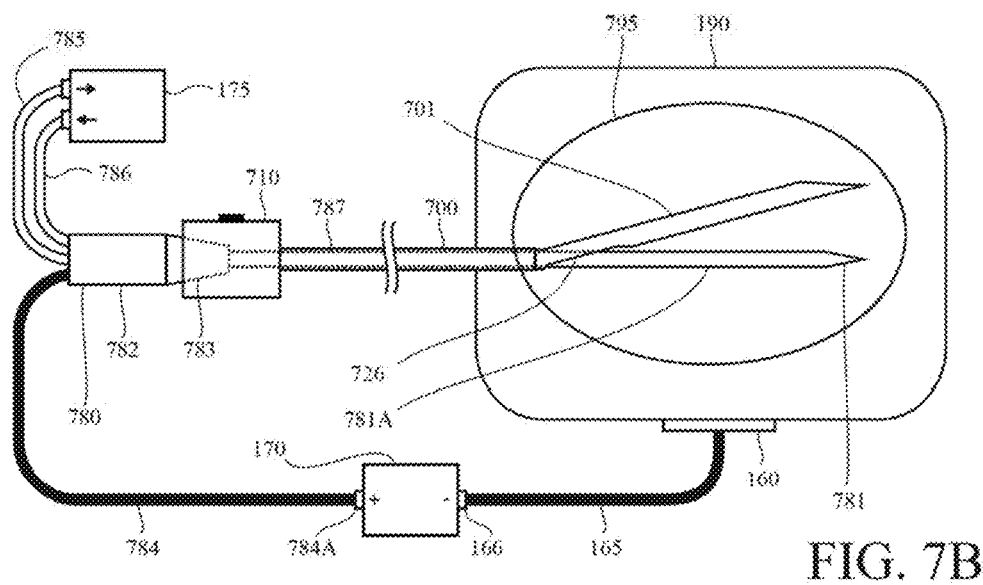
FIG. 7B is a schematic diagram showing the cooled RF electrosurgical system of FIG. 7A wherein the cannula is inserted into bodily tissue; a fluid pump circulates fluid through the electrode shaft via the electrode inflow port and outflow port; the electrode shaft is inserted through the cannula hub, extends into the tissue via the side opening in the cannula active tip, and is electrically connected to a first output pole of an RF generator via the electrode generator connection; a reference plate electrode is placed on the surface of the bodily tissue and is electrically connected to the second output pole of an RF generator; and the RF generator generates an RF potential between the first pole and the second pole so that RF current flows through the tissue from both the cannula active tip and the electrode shaft to the reference plate electrode, thereby heating the bodily tissue.
Figure 7C:
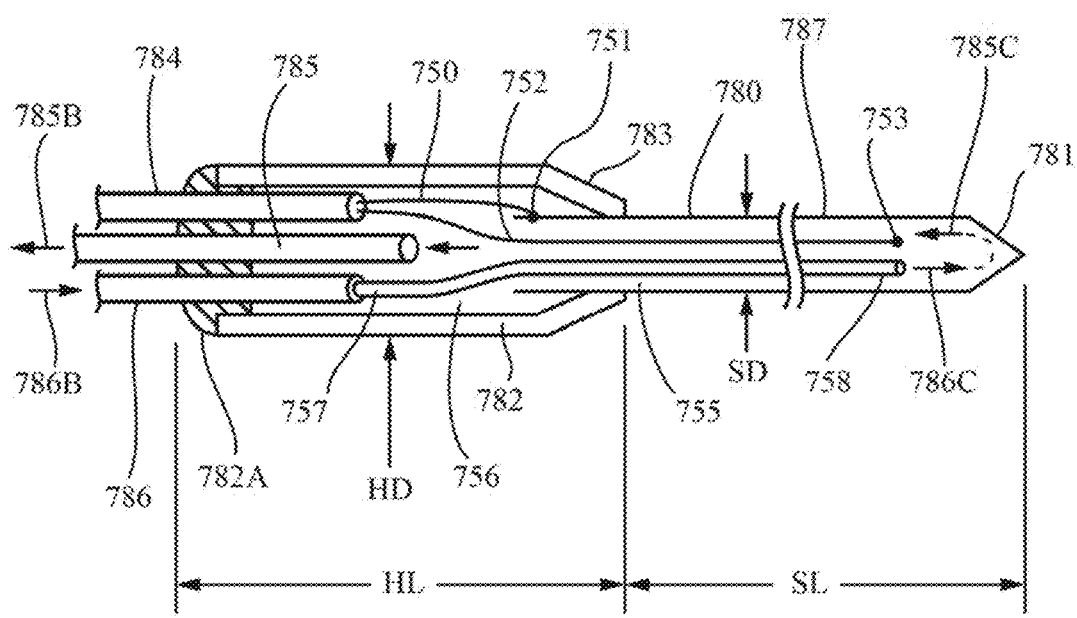
FIG. 7C is a schematic diagram showing a construction of an internally-cooled RF electrode.

Referring now to FIG. 7, in accordance with several aspects of the present invention, FIG. 7 refers collectively to FIG. 7A, FIG. 7B, and FIG. 7C. FIG. 7 presents schematically several embodiments of a side-outlet cooled RF ablation probe system including a cannula 700 having an insulated shaft 730 and an active tip 701 at its distal tissue-piercing end, a cannula stylet 740 including a shaft bend 746 that allows the stylet to be directed past cannula side opening 726 into the cannula lumen 705 distal to the side opening 726, and an internally-cooled RF electrode 780 that electrifies the cannula active tip 701 and consistently extends out from a side opening 726 near the cannula distal end 721 when the straight conductive electrode shaft 787 is fully inserted into the cannula lumen 705 through the cannula hub 710 such that the distal electrode hub 783 engages with the cannula hub port 712 at the cannula proximal non-tissue-piercing end. The electrode 780 includes a sharpened distal point 781, coolant inflow tube 786 with connector 786A, and coolant outflow tube 785 with connector 785A, and generator connection wire 784 with connector 784A. Coolant pumped by coolant pump and source 175 through tube 786 flows to the distal end 781 of the electrode shaft 787, then reverses direction to flow back to the proximal hub 782 and out through the tube 785. RF signals applied connector 784A are conducted through cable 784 to the conductive electrode shaft 787 outer surface. Temperature signals measured at the electrode distal end 781 are conducted through cable 784 to connector 784A from which the signals can be measured by an RF generator 170. The shaft 787 of the electrode is stiff to provide for penetration of solid tissue. In some embodiments, the distal tip 781 can be blunt. In some embodiments, the distal tip 781 can include an coaxial or lateral extension that hold a temperature sensor at a distance from the conductive shaft 781, wherein the extension can be either electrical connected to the shaft 781 or electrically insulated from the shat, and wherein the extension can either be fixed to the shaft 787 or movable relative to the shaft 787. The cannula bend 706 and side opening 726 are configured so that the electrode shaft 787 will not enter the distal portion of the lumen 705 within the cannula active tip 701 when the electrode is inserted into the cannula lumen 705 through the cannula hub 701 in any rotational orientation. In some embodiments, the electrode 780 and cannula 700 can have dimensions in the same ranges as those possible for embodiments of the electrode 180 and the cannula 100. For some tissue ablation applications in large organs such as the liver, the electrode shaft can be 17 gauge and the cannula shaft can be 15 gauge. In some embodiments, the electrode 780, cannula 700, and stylet 740 can have the same general features and dimensions of the electrode 180, cannula 100, and stylet 140.

In one aspect, FIG. 7 relates to a cannula 700 having an active tip 701 and a bend 706 in the cannula shaft 707, and an internally-cooled RF electrode 780 having a substantially straight shaft 787 that electrifies the cannula active tip 701 and extends from a side opening 726 near the cannula tissue-penetrating end 721, wherein the assembly of the electrode 780 and the cannula 700 can be used to generate a large, asymmetrical heat lesion around both the cannula active tip 701 and the portion of the electrode shaft 787 that extends out of the cannula side opening 726. In one aspect, FIG. 7 relates to a side-outlet cooled RF ablation system that includes a standard cooled RF electrode, such as the Radionics Cool-Tip electrode, and an RF cannula having a side opening from which the electrode extends into tissue. In one aspect, FIG. 7 relates to the adaptation of an internally-cooled RF electrode having a stiff, straight shaft to a side-opening RF ablation configuration.

Referring now to FIG. 7A, the electrode 780, cannula 700, and stylet 740 are shown separately in an external view of the side of each element.

Referring now to FIG. 7B, the electrode 780 and cannula 700 are assembled and operably connected to an RF generator 170, a coolant pump 175, and a ground pad 160 to produce an monopolar RF heat lesion 795 within bodily tissue 190. This configuration was achieved by the process of inserting the cannula 700 into the tissue 190 with the stylet 740 fully inserted into the cannula lumen 705, removing the stylet 740 from the cannula 700, inserting the electrode 780 into the cannula lumen 705 via the cannula hub 710, connecting the electrode 780 to the pump 175 and RF generator 170, connecting the RF generator 170 to one or more ground pads 160 places on the surface of bodily tissue 190, circulating cooling fluid such as saline or water through the electrode shaft 787 by means of the pump 175, and applying an RF potential between the electrode shaft 787 and the ground pad 160 by means of the RF generator 170. RF current flow into tissue 190 from both the extension of the electrode shaft out of the cannula side opening 781A and the cannula active tip 701, due to conduction of RF current between the electrode conductive shaft 787 and conductive inner wall of the cannula shaft 707.

Referring now to FIG. 7C, an internal view of the internally-cooled electrode 780 is shown in schematic form. Coolant, such as saline or water, flows through inflow tube 786, as indicated by arrow 786B, into shaft tube 757 within the electrode shaft 787, and out from the distal end 758 of the shaft tube 575 into the lumen 755 of the electrode shaft 787. The coolant then reveres direction as indicates by arrows 786C and 785C to flow in a distal to proximal direction within lumen 755 into the hub lumen 756 and out through tube 785 as indicated by arrow 785B. Generator cable 784 includes an RF connection wire 750 that attaches to conductive shaft tube 787 at junction 751 to conduct an RF potential from an RF generator to the outer surface of shaft 787. Generator cable 784 also includes a temperature connection wire 752 that conducts temperature signals from temperature sensor 753 near the distal end 781 of the electrode shaft 787 to the RF generator. The temperature sensor 753 can be a thermocouple, a thermistor, or another type of temperature sensor. In some embodiments, the electrode 780 can include an addition tube with the electrode shaft to conduct coolant out of the shaft. In some embodiments, the temperature sensor 783 can extend from the electrode shaft 787 either from the distal end 781 or the side of shaft 787, either fixedly or slidably attached to the shaft 787, and either electrically insulated or electrically-connected to the shaft 787, to measure a temperature at a distance from the shaft 787.

Figure 8A:
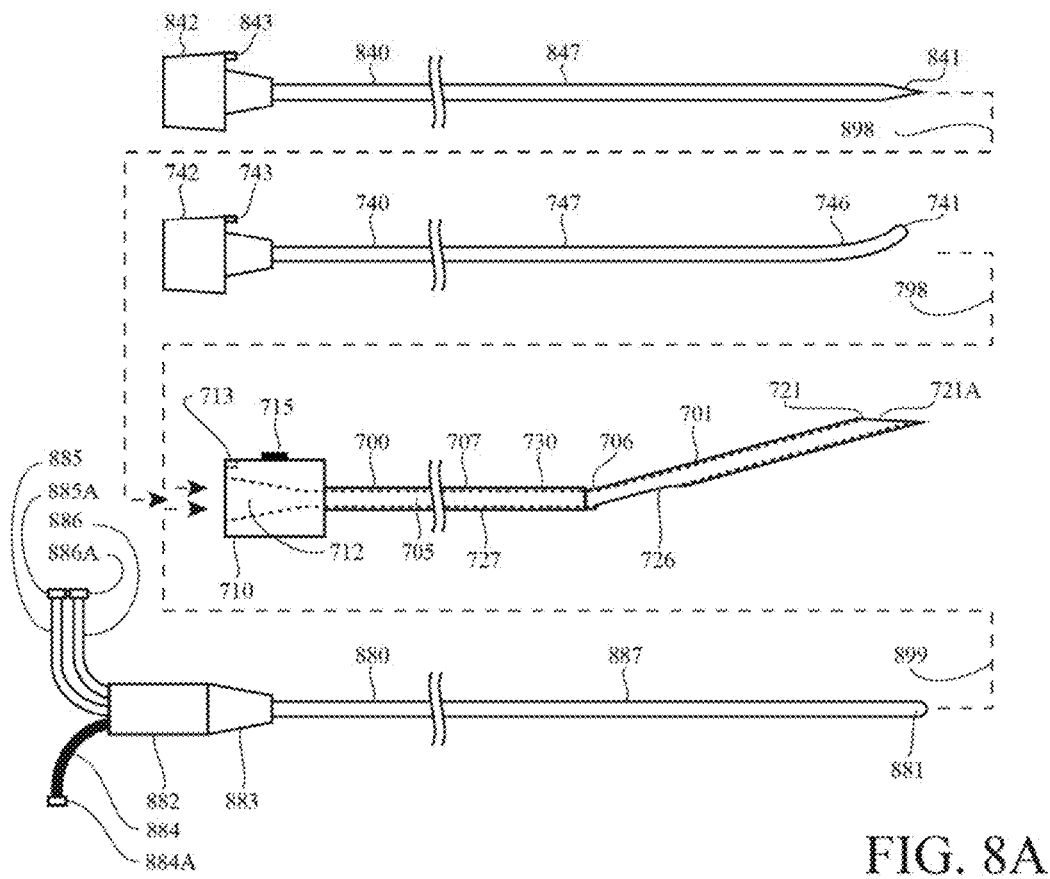
FIG. 8A is a schematic diagram showing a cooled RF system including a blunt-tip internally-cooled RF electrode, an RF cannula, a cannula stylet, and a tissue-piercing extension stylet wherein the extension stylet is configured to extend from a side opening at a bend in the cannula active tip to make a path in bodily tissue for the electrode, and the electrode is configured to consistently extend from a side opening at a bend in the cannula active tip.
Figure 8B:
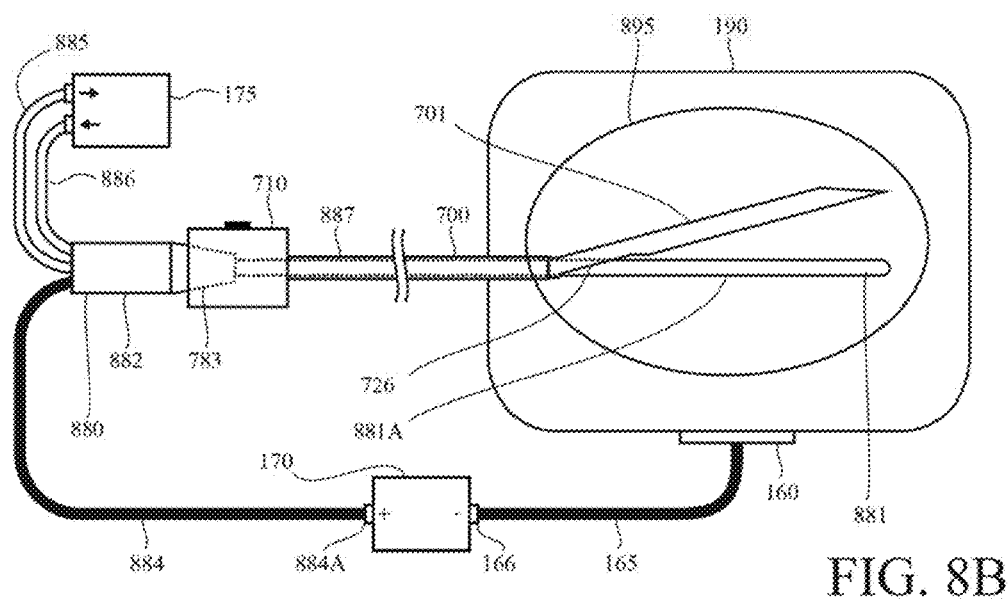
FIG. 8B is a schematic diagram showing the operation of the cooled RF system wherein an RF ablation zone is created in bodily tissue around the assembly of the cannula active tip and the portion of the electrode shaft extending from the side opening in the cannula active tip.

Referring now to FIG. 8, in accordance with several aspects of the present invention, FIG. 8 refers collectively to FIG. 8A, FIG. 8B, and FIG. 8C. FIG. 8 presents schematically several embodiments of a cooled RF ablation probe system including the cannula 700 and stylet 740 presented in FIG. 7, an internally-cooled RF electrode 880 which electrifies the cannula active tip 701 and whose blunt distal end 881 consistently extends out from a side opening 726 near the cannula tissue-penetrating end 721 when the straight electrode shaft 887 is fully inserted into the cannula lumen 705 through the cannula hub 710, and a straight extension stylet 840 having a straight shaft 847 that extends out from the cannula side open 726 to create a path in bodily tissue for later insertion of the straight electrode shaft 887 via the cannula side opening 726. The electrode 880 is identical to the electrode 780 except that the distal point 881 at the tissue-penetrating end of the electrode 880 is blunt rather than sharpened. The shaft 847 of the extension stylet 840 is sized relative to the stylet cap 842 so that the extension stylet extends beyond the cannula side opening 726 by the same length as does the electrode shaft 880 when fully inserted into the cannula lumen 705 via the cannula hub 710. The extension stylet 840 is configured to consistently extend from the cannula side opening 726 when the extension stylet 840 is fully inserted into the cannula lumen 705 via the cannula hub 710. In one aspect, FIG. 7 relates to the use of a non-tissue-piercing cooled RF electrode 880 having a straight shaft in concert with an RF cannula to enlarge the size of an RF heating lesions both by internally-cooling of the electrode shaft and increasing the effective active tip surface (comprising both the cannula active tip 701 and the extension of the electrode shaft 887 from the cannula side outlet 726) by means of a side-outlet electrode configuration.

Referring now to FIG. 8A, the electrode 880, cannula 700, stylet 740, and extension stylet 840 are shown separately in an external side view.

Referring now to FIG. 8B, the electrode 880 and cannula 700 are shown in assembled configuration, producing an RF heat lesion 895 within bodily tissue 190 using monopolar RF, internal electrode cooling, and side-outlet-tip methods at the same time. The pump and coolant source 175 cools the electrode shaft 887. The generator 170 electrifies the electrode shaft 887 and the cannula active tip 701 with an RF signal. The ground pad 160 carries return current from the electrode shaft 887 and the cannula active tip 701.

Referring now to FIG. 9, in accordance with several aspects of the present invention, FIG. 8 refers collectively to FIG. 9A, FIG. 9B, FIG. 9C, and FIG. 9D. FIG. 9 presents schematically several embodiments of a bipolar cooled RF ablation probe systems.

Figure 9A:
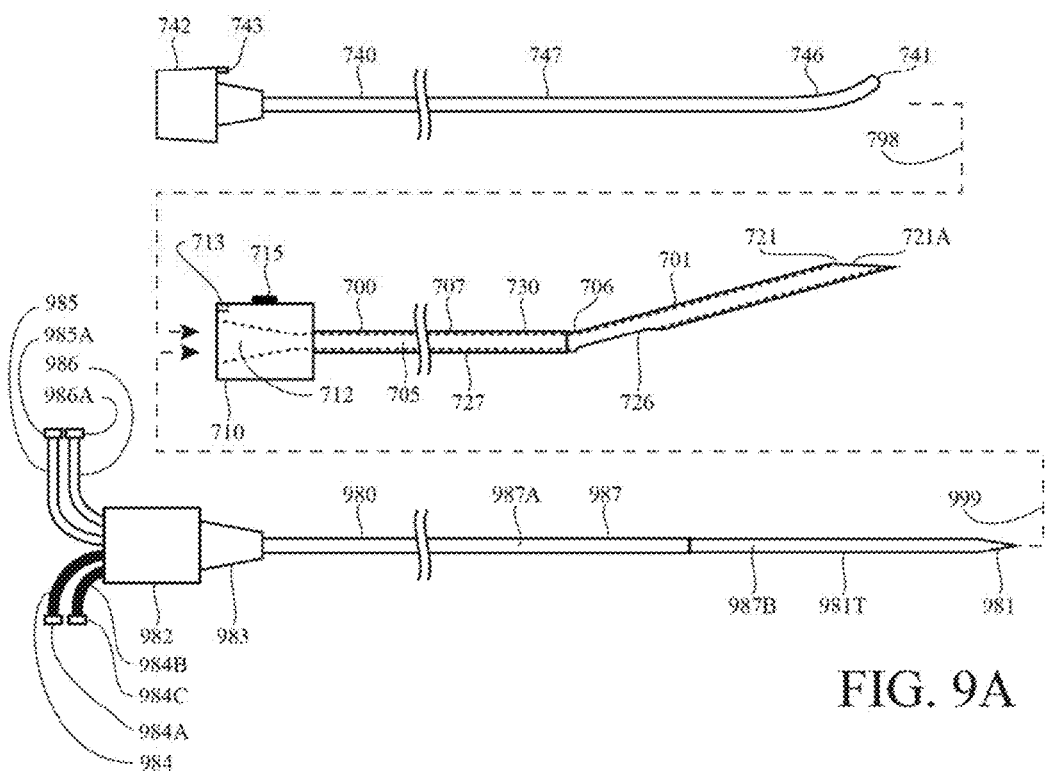
FIG. 9A is a schematic diagram showing a bipolar cooled RF probe system including an internally-cooled RF electrode having an insulated shaft and an active tip, and a bent-tip cannula having an insulated shaft and an active tip, wherein the electrode includes an inflow pump connection and an outflow pump connection for circulating of coolant within the electrode active tip, the electrode includes a first generator connection by which an electrical signal can be conducted to the electrode active tip, the electrode includes a second generator connection by which an electrical signal can be conducted to the cannula active tip via contact between a conductive surface of the electrode hub and a conductive surface of the cannula hub, the cannula active tip and the electrode active tip are electrically isolated within the system when the electrode is fully inserted into the cannula inner lumen via the cannula hub, the electrode shaft always extends from a side opening in the cannula active tip and the electrode active tip when the electrode is fully inserted into the cannula lumen via the cannula hub.
Figure 9B:
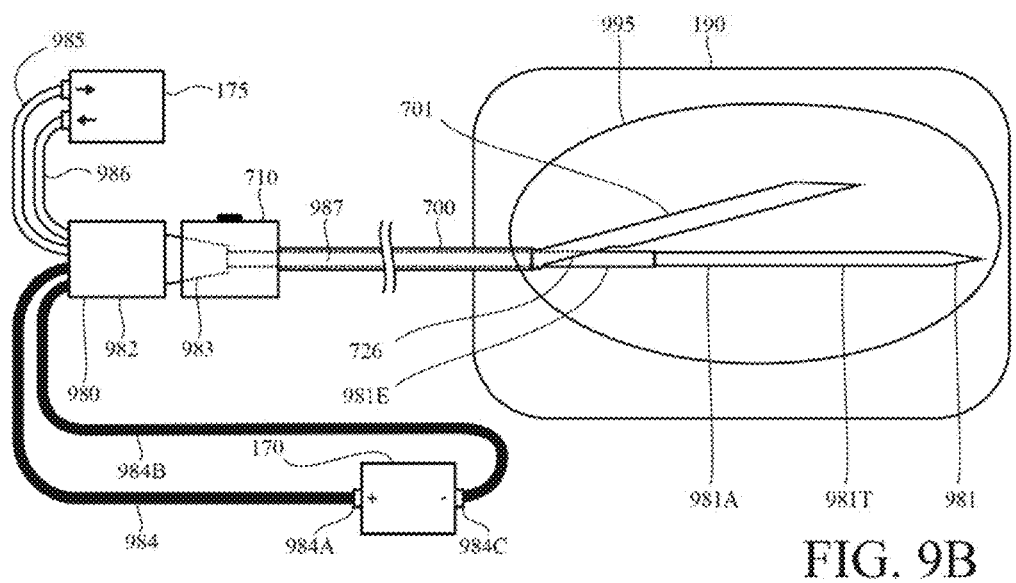
FIG. 9B is a schematic diagram showing the formation of a RF heat lesion within bodily tissue by means of the electrode and cannula of FIG. 9A inserted into the tissue, wherein a pump circulates coolant through the electrode active tip, the electrode active tip is connected to a first output pole of an RF generator, the cannula active tip is connected to a second output pole of an RF generator via the seating of the electrode hub in the cannula hub, the RF generator drives RF current through the tissue between the electrode active tip and the cannula active tip.
Figure 9C:
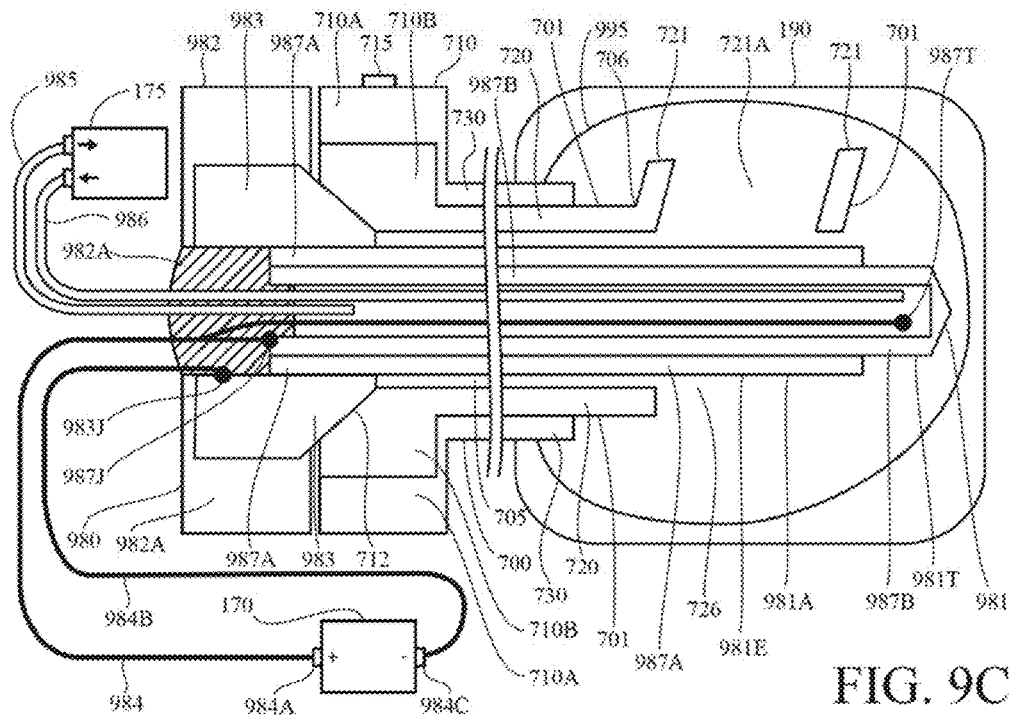
FIG. 9C is a schematic diagram showing a cross-sectional detail of the assembly of the electrode and cannula shown in FIG. 9B.

Referring now to FIGS. 9A, 9B, and 9C collectively, a bipolar side-outlet cooled RF ablation system is shown that includes the cannula 700 and stylet 740 presented in FIG. 7, and an internally-cooled RF electrode 980 having a straight partially-electrically insulated shaft 987 with active tip 981T whose sharp distal end 981 consistently extends out from a side opening 726 near the cannula tissue-penetrating end 721 when the electrode shaft 987 is fully inserted into the cannula lumen 705 through the cannula hub 710. The electrode 980 has the same general features as electrode 780 with the modification that the shaft 987 is longer to increase the separation between the electrode active tip 981T and the cannula active tip 701, the shaft 987 is electrically insulated over a proximal length 987A, the electrode 980 includes a second generator connection 984C that conducts an RF signal from an RF generator 170 to a conductive surface 983 of the electrode hub 982 that conducts the RF signal to the cannula active tip 701 by engaging with the cannula hub 710, and the electrode 980 internally isolates the RF signal conducted by the first generator connection 984A and the RF signal conductive by the second generator connection 984C. The embodiments of cannula 700 shown in FIG. 9 include a construction adapted to conduct a signal from electrode hub taper 983 to the cannula active tip 701; in one embodiment, the cannula hub port 712 is conductive, engages with the electrode hub surface 983 when the electrode 980 is inserted into the port 712, and is electrically-conductively connected to the metal tube 720 constructing the cannula shaft 707 and the cannula active tip 701. As such, then the electrode 980 is fully inserted into the cannula lumen 705 through the cannula hub 710, the distal taper 983 of the electrode 980 engages with the cannula port 712 to conduct a signal from the second generator connection 984C of electrode 980 to the cannula active tip 701.

Referring now to FIG. 9A, the electrode 980, cannula 700, and stylet 740 are shown separately in an external side view.

Referring now to FIG. 9B, the electrode 980 and cannula 700 are shown in assembled configuration, producing an RF heat lesion 995 within bodily tissue 190 using bipolar RF, internal electrode cooling, and side-outlet-tip methods at the same time. The pump and coolant source 175 cools the electrode shaft 887. The generator 170 electrifies the electrode shaft 887 and the cannula active tip 701 with an RF signal. The ground pad 160 carries return current from the electrode shaft 887 and the cannula active tip 701. The first output pole "+" of the generator 170 is connected to the electrode active tip 981T via connection 984A and cable 984. The second output pole "−" of the generator 170 is connected to the cannula active tip 701 via connection 984C, cable 984B, and the engagement of the electrode hub taper 983 and the cannula hub 710. The RF potential of the first and second output poles of the RF generator 170 are isolated from each other within the assembly of the electrode 980 and the cannula 700, but generate RF current between the cannula active tip 701 and the electrode active tip 891T within the tissue 190 to form heat lesion 995. The pump 175 circulates coolant through the electrode shaft 987. The hub marker 715 is aligned with the cannula shaft bend 706. Portions of the electrode hub 983 and shaft 987 are shown within the cannula 700 as dotted lines.

The portion of the electrode shaft 987 that extends from the cannula side opening 726 into the tissue 190 includes electrode tissue-piercing point 981, the electrode active tip 981T, and the distal portion of the electrode shaft insulation 981E. The length of the electrode shaft insulation 981E is configured to extend beyond the distal aspect of the cannula side opening 726 to prevent inadvertent short circuiting between the electrode active tip 981T and the cannula active tip 701, and reduce the degree of focusing of RF current in tissue between the point when the electrode active tip 981T and the cannula active tip 701 are closest together. The length of the electrode active tip 981T is configured to be equal to the length of the cannula active tip 701. In some embodiments, the electrode active tip 981T and the cannula active tip 701 can be sized to have the same surface area. In some embodiments, the electrode active tip 981T can be larger than the cannula active tip 701. In some embodiments, the electrode active tip 981T can be smaller than the cannula active tip 701, for example, so that the cannula active tip 701 is within the region substantially cooled by coolant within the electrode shaft 987. In some embodiments, the distal point 981 of the electrode is blunt to minimize high electric fields at the point 981.

Referring now to FIG. 9C, the electrode 980 and cannula 700 are shown the assembled, operational configuration of FIG. 9B, and one embodiments of the internal construction of the electrode 980 and cannula 701 is shown.

The electrode shaft 987 includes conductive metal tubing 987B that is covered by electrical insulation tubing 987A over the entire length of the tubing 987B except for the distal portion of the tubin 987B which forms the electrode active tip 981T. The electrode shaft 987 is fixed to the electrode hub 982. The electrode hub includes the conductive hub taper 983 and electrical insulation 982A that covers all but the portion of the taper 983 that engages with the cannula hub port 112. The electrode hub taper 983 is electrically isolated from the electrode shaft tubing 987B by the electrical insulation 987A and the electrically-insulating plug 982A that pots the interior of the hub 982 and its contents. Generator cable 984 splits into two wires within the electrode hub 982, the first wire conducting an RF potential from the "+" jack of generator 170 to conductive electrode shaft tubing 987B (and thus the electrode active tip 981T) via conductive junction 987J (which can be a solder or weld joint), and the second wire carrying a temperature signal to the generator 170 from the temperature sensor 987T within the distal tip of the electrode shaft 981. The generator cable 984B mounts to the electrode hub taper 983 via conductive junction 983J (which can be a solder or a weld joint) and conducts an RF potential from the "−" jack of generator 170. The electrode hub taper 983 is electrically isolated from the electrode active tip 981T within the electrode by the electrically-insulative plug 982J and electrode shaft insulation 987A. In some embodiments, the electrical insulation covering the cannula hub 710A is a physically separate part from the electrical insulation 730 covering the electrode shaft tube 720. In some embodiments, particularly those not specialized to a bipolar electrode and cannula system, the cannula hub 710 is constructed from a first part 710B that is attached to a second part 720 forming the cannula shaft tubing, rather than 710B and 720 being integral to it as shown in the embodiment of FIG. 9C.

The cannula hub 710 includes a conductive body 710B conductively connected to the cannula shaft tube 720, electrical insulation 710A covering the conductive body 710B for handling, and port 112 to the cannula lumen 705 formed in the hub conductive body 710B. The cannula shaft includes a conductive metal tube 720 whose proximal end is covered by electrical insulation 730, leaving an uncovered active tip portion 701 which includes the bend 706, the side opening 726, the sharp distal bevel point 721, and the bevel opening 721A.

The electrode shaft 987 is inserted through the cannula hub port 712 and the conductive hub taper 983 engages with the conductive body 710B of the cannula hub 710 via the hub port inner surface 712, thereby conducting the RF potential from the "−" generator jack to the cannula shaft tube 720 and the cannula active tip 701. The electrical insulation 987A electrically isolates the electrical potential applied to the cannula shaft tube 720 and the cannula hub body 710B from the electrical potential applied to the electrode shaft tube 987B by the "+" pole of the RF generator 170. In some embodiments, the cable 984 for the electrode active tip 981T can be housed in a single cable with the cable 984B for the cannula active tip 901; this can be an important advantage in reducing procedural complexity during an RF ablation procedure.

Coolant fluid, such as saline or water, is pumped by pump 175 through tube 986 to the distal end of the electrode shaft 987, and then flows back through the lumen of the electrode shaft 987B to the tube 985, through which it flows out of the electrode 980 to be discarded or recirculated by the pump 175. The coolant fluid is electrically isolated from the potential of the cannula active tip 701 by electrically-insulative hub plug 982A which separates the fluid from conductive element 983.

In some embodiments, each of the electrode 780, electrode 880, and electrode 980 can include outflow ports near its distal end to enhance lesion size by perfusion of coolant saline into tissue as well as internal-cooling of the electrode shaft by circulation of coolant saline within the electrode shaft.

One advantage of each of the systems present in FIG. 7, FIG. 8, and FIG. 9 is that it can provide for side-outlet operation to increase the side of a heat lesion formed by a cooled RF method by means of a side-outlet electrode method. One advantage of each of the systems present in FIG. 7, FIG. 8, and FIG. 9 is that they include a cannula that operations with a stylet to close the cannula distal end and thereby facilitate insertion of the cannula and electrode into bodily tissue; in one example, this can avoid displacement of organs, such as tough organs like a cirrhotic liver containing a tumor, during insertion of the ablation system, potentially frustrating the use of pre-operative imaging for procedure guidance. One advantage of each of bipolar systems presented in FIG. 9 is that return current from the system and cannula do not need to flow long distances through the body to one or more reference electrodes, at which inadvertent skin burns can occur when applying high RF power, such as during tumor ablation using a cooled RF probe during tumor ablation.

Figure 9D:
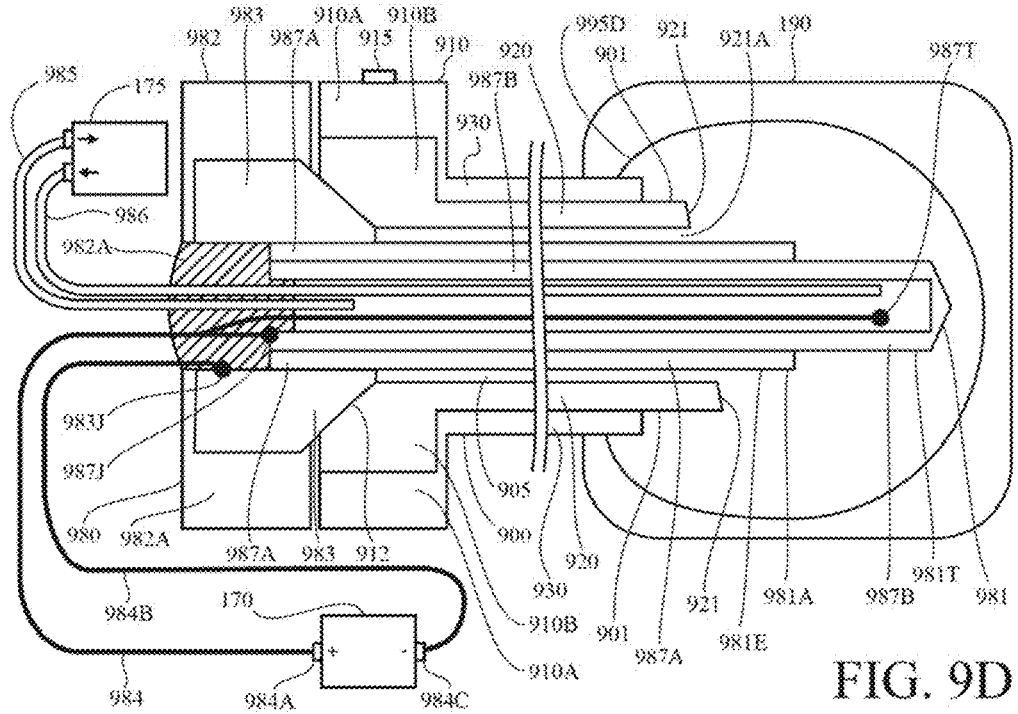
FIG. 9D is a schematic diagram showing cross-sectional detail of a bipolar cooled RF probe system including an internally-cooled RF electrode having an insulated shaft and an active tip, and a straight-tip cannula having an insulated shaft and an active tip, wherein a pump circulates coolant through the electrode active tip via inflow pump tubing and outflow pump tubing, the electrode active tip is connected to a first output jack of an RF generator via a first generator connection to the electrode, the cannula active tip is connected to a second output jack of an RF generator via a second generator connection to the electrode and via physical contact between a conductive surface of the electrode hub and a conductive surface of the cannula hub, the cannula active tip and the electrode active tip are electrically insulated from each other within the assembly of the electrode and the cannula, the cannula is inserted into bodily tissue, the electrode shaft is inserted into the cannula lumen via the cannula hub and extends from a opening in the sharp bevel at the tissue-piercing end of the cannula active tip, and the RF generator drives RF current through the tissue between the electrode active tip and the cannula active tip to form a heat lesion within the bodily tissue.

Referring now to FIG. 9D a coaxial bipolar cooled RF ablation system is presented schematically that includes the electrode 980 and a straight RF cannula 900 not having a side outlet, wherein the cannula 900 and the electrode 980 are shown in an assembled, operational configuration in which an RF generator 170 and coolant pump 175 are used to generate a bipolar RF heat lesion 995D in bodily tissue 190, into which the electrode 980 and cannula 900 are inserted. This configured as achieved by a process including inserted the cannula 900 into the bodily tissue, inserting the electrode 980 into the cannula lumen 905 through cannula hub port 912 so that the electrode shaft 987 exits the distal opening 921A to cannula lumen 905, pumping coolant through the electrode shaft 987 by means of pump 175, and applying an RF current through the tissue 190 between the cannula active tip 901 and the electrode active tip 981T and through the conductive interface between the electrode taper 983 and the cannula port 912. The construction of the cannula 900 is similar to the embodiment of the cannula 700 shown in FIG. 9C, except for the omission of a shaft bent 706, omission of a cannula side opening 726, and configuration of the length of the cannula shaft tube 920 so that the electrode 980 exits the lumen 905 of the cannula shaft tube 920 through the opening 921A in the cannula distal bevel 921 when the electrode 980 is inserted into the cannula lumen 905 through the hub port 912. The coolant within the electrode shaft cools both the electrode active tip 981T and the cannula active tip 901 by heat conduction. The coolant temperature, coolant flow rate, the wall thickness of the electrode shaft 987B, the gap between the electrode shaft 987 and the cannula shaft 907, the wall thickness of the cannula shaft 907 are each configured to provide for cooling of both the electrode active tip 981T and the cannula active tip 901, and to provide for slidable engagement between the electrode shaft 987 and the cannula shaft 907.

Figure 10A:
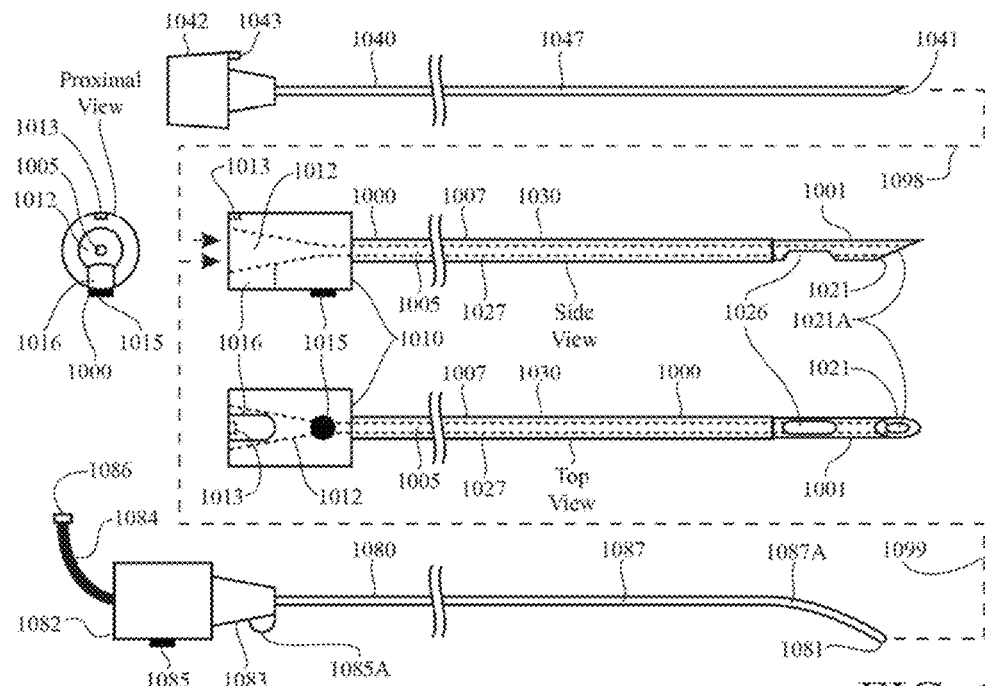
FIG. 10A is a schematic diagram showing an RF ablation probe system including an electrode and a cannula, wherein the electrode conductive shaft includes a bend near its tissue-penetrating end; the electrically-insulated shaft of the cannula is substantially straight and includes an electrically-conductive active tip; the active tip includes a side opening to the cannula lumen; the cannula lumen extends through the entire length of the cannula shaft, is open at the cannula hub and at the cannula tissue-penetrating end, and is bounded by an electrical-conductive inner surface of the cannula that is electrically connected to the cannula active tip; the electrode is configured to be inserted into the cannula lumen through the cannula hub; the electrode hub includes a tab that prevents insertion of the electrode shaft tip into the cannula lumen beyond the side opening in the cannula active tip unless the tab is aligned with a slot in the cannula hub; the bend in the electrode shaft, the side opening, the tab of the electrode hub, and the slot of the cannula hub are configured so that the electrode shaft consistently exits the side opening of the cannula active tip when the electrode is fully inserted into the cannula via the cannula hub.
Figure 10B:
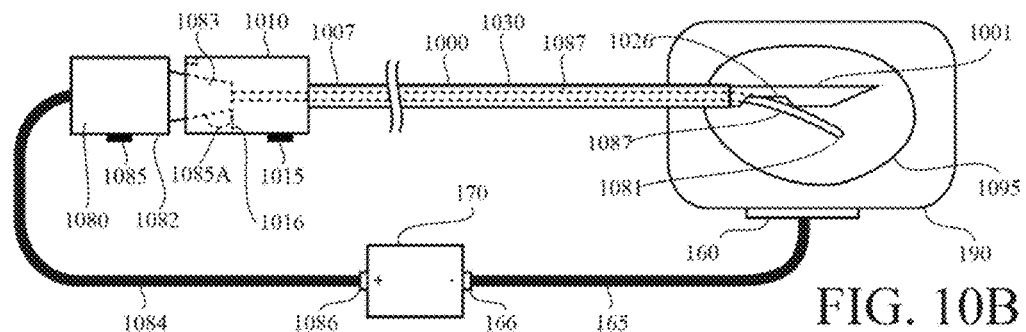
FIG. 10B is a schematic diagram showing the formation of a monopolar heat lesion in bodily tissue by means of the RF ablation probe system of FIG. 10A, wherein the cannula active tip and the portion of the electrode shaft that extends out of the side opening of the cannula active tip are brought to same electrical potential by connection of the electrode shaft to an RF generator and by contact between the conductive electrode shaft and the electrically-conductive inner surface of the cannula.
Figure 10C:
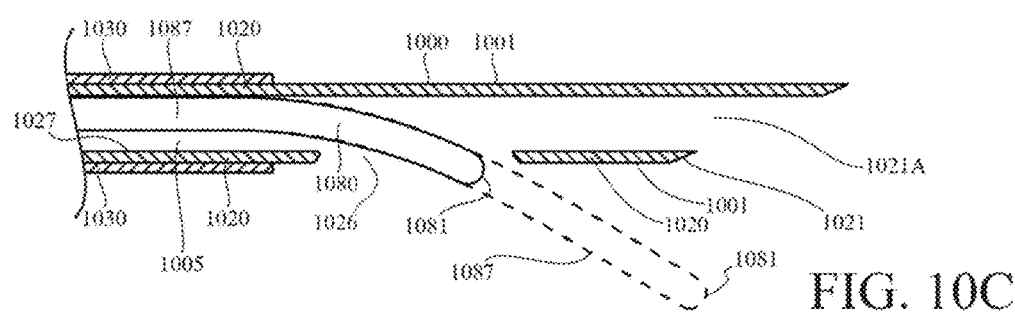
FIG. 10C is a schematic diagram showing a cross-sectional detail of tissue-penetrating end of the cannula of FIG. 10A and the tissue-penetrating end of the electrode of FIG. 10A, wherein the electrode is shown both in a first position in which the electrode tissue-penetrating tip is within the cannula lumen and is aligned with the side opening in the cannula active tip, and in a second position wherein the electrode tissue-penetrating tip is extended out from the side opening in the cannula active tip; the second position following from the first position by sliding the electrode shaft within the cannula lumen toward the cannula tissue-penetrating end with the electrode hub tab in alignment with the cannula hub slot.

Referring now to FIG. 10, in accordance with several aspects of the present invention, FIG. 10 refers collectively to FIG. 10A, FIG. 10B, and FIG. 10C. FIG. 10 presents schematically several embodiments of a side-outlet ablation system including a cannula 1000, and cannula stylet 1040, and an electrode 1080; the cannula 1000 including a hub 1010 at the cannula proximal non-tissue-penetrating end, a straight cannula shaft 1007 including an electrically-insulated proximal shaft portion 1030 and a distal electrically conductive active tip 1001, a lumen 1005 through the entire length of the cannula hub and shaft, the hub 1010 including a proximal opening to the cannula lumen 1012, the distal shaft bevel 1021 including a distal opening 1021A to the cannula lumen 1005, the shaft including a side opening 1026 to the cannula lumen 1005 within the active tip 1001, a slot 1016 in the cannula hub 1010 having an alignment with the side opening 1026, an indicia 1015 aligned with the side opening 1026; the electrode including a conductive electrode shaft 1087 shaped to form a bend 1087A near the distal end 1081 of the electrode shaft 1081, a generator connection 1086 conductively connected to the electrode conductive shaft 1087 and to a temperature sensor 1081 within the electrode shaft distal point, a hub at the proximal non-tissue-penetrating end of the electrode 1087, a tab 1085A on the electrode hub 1082 having an alignment with the bend 1087A, an indicia 1085 on the hub 1082 aligned with the bend 1087A; the stylet 1040 having a proximal cap 1042 that engages with the cannula hub 1010, cap tab 1043 that engages with cannula hub slot 1013 to key the orientation of the stylet tip 1041 relative to cannula bevel 1021, shaft 1047, and distal bevel 1041 which aligns with the distal opening 1021A and bevel 1021 of the cannula 1000 when the stylet shaft 1047 is inserted into the cannula lumen 1005 via the proximal hub port 1012; wherein the electrode shaft 1087 can be inserted into the cannula lumen 1005 via the cannula hub port 1012 and thereby conducts an electrical potential from the generator connection 1086 to the cannula active tip 1001 through the electrode shaft 1087, the electrode shaft 1087 exits the cannula lumen 1005 from the side opening 1026 when the electrode shaft 1087 is inserted into the cannula lumen 1005 and the electrode hub tab 1085A engages with the cannula hub slot 1016, the electrode hub tab 1085A and the cannula hub slot 1016 prevents advancement of the electrode shaft distal end 1081 past the cannula side opening 1026 within the cannula lumen 1005. In some embodiments, the cannula shaft 1007 can include a bend near the distal end of the cannula shaft 1021, for example, within the length of the active tip 1001, or near the active tip 1001 in the cannula insulated shaft portion 1030. One advantage of the system present in FIG. 10 is that the assembly of the electrode 1080 and cannula 1000 can be used reliably in a side-outlet RF lesioning configuration, avoiding accidental failure of the electrode tip 1081 to extend from the cannula side opening 1026 if the electrode is inserted into the cannula lumen 1005 in the wrong rotational orientation about the cannula shaft axis. In some embodiments, another form of interlocking elements can be used to key the rotational orientation of the electrode shaft bend 1087A and the cannula side opening 1026, such that the electrode tip 1081 only exits the cannula side opening 1026 when the electrode 1080 is fully inserted into the cannula 1000, and otherwise the electrode 1080 is otherwise restricted from advancing fully into the cannula 1000.

Referring now to FIG. 10A, the cannula 1000, stylet 1040, and electrode 1080 are shown separately in a side view, the cannula 1080 is additionally shown in a proximal view from the proximal aspect of the cannula hub 1010, and the cannula 1000 is additionally shown in a top view. The cannula hub port 1012, stylet tab slot 1013, and lumen 1005 are shown as dotted lines through the cannula wall.

Referring now to FIG. 10B, an assembly of the electrode 1080 and cannula 1000 are shown in a side view, the electrode 1080 being fully inserted into the cannula 1000 with the electrode hub tab 1085A engaged with the cannula hub slot 1016, the electrode shaft 1087 extending into bodily tissue 190 from the cannula side opening 1026, the assembly being inserted into bodily tissue 190 and operably connected to an RF generator 170 and ground pad 160 to produce an asymmetric monopolar heat lesion 1095 within the tissue 190 around the cannula active tip 1001 and the protruding portion of the cannula shaft 1087, wherein the RF generator 170 controls the RF output using the tissue temperature measured by the electrode tip sensor 1081.

Referring now to FIG. 10C, a cross-sectional detail of the distal end of the cannula 1000 is shown with the electrode 1080 inserted into the cannula lumen 1005 and in two positions showing the process by which the electrode tip 1081 exits the cannula side opening 1026. In the first position, the electrode shaft 1087 is shown in a solid line, and the electrode tip 1081 is positioned at the cannula side opening 1026 with the electrode tip bend 1087A directing the electrode tip 1081 toward and out of the side opening 1026. In the second position, which was achieved by advancing the electrode 1080 from the first position toward the cannula distal end 1021, the electrode shaft 1087 extends from the side opening 1026 of the cannula 1000.

Figure 11A:
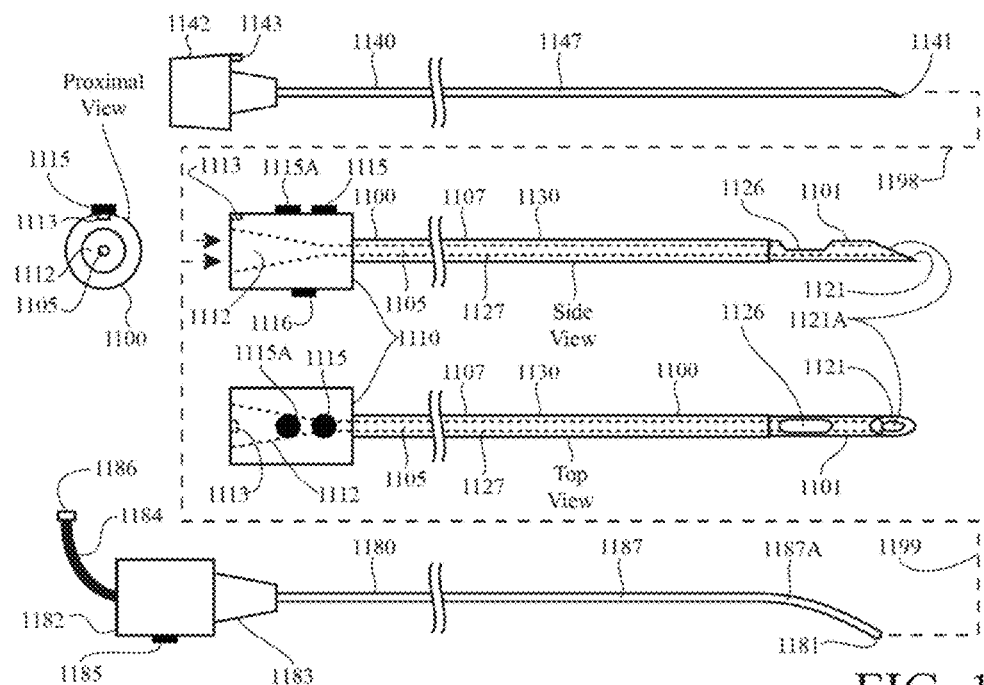
FIG. 11A is a schematic diagram showing an RF lesioning system including an electrode and a cannula, wherein the conductive electrode shaft includes a predetermined bend near the tissue-penetrating end of the electrode shaft; the electrode hub includes a first visible indicator of the orientation of the electrode shaft bend; the cannula shaft is substantially straight and is constructed from conductive tubing fully covered by electrical insulation except for an active tip region at the cannula tissue-piecing end of the cannula shaft; the active tip includes a sharpened bevel and a side outlet to the cannula lumen within the metal tubing that constructs the cannula shaft; the cannula hub includes a port opening to the cannula shaft lumen, a second visible indicator aligned circumferentially with the side outlet, and a third visible indicator positioned on the side of the cannula opposite the side outlet; the electrode shaft length, the cannula shaft length, the electrode shaft bend, and the cannula side outlet are configured such that when the first visible indicator on the electrode hub is aligned with the second visible indicator on the cannula hub, and the electrode shaft is fully inserted into the cannula lumen through the cannula hub, the electrode shaft extends out of the side outlet; the electrode shaft length, the cannula shaft length, the electrode shaft bend, and the cannula side outlet are configured such that when the first visible indicator on the electrode hub is aligned with the third visible indicator on the cannula hub, and the electrode shaft is fully inserted into the cannula lumen through the cannula hub, the electrode shaft extends into the lumen of the cannula tube beyond the side outlet, and the end of the electrode shaft is aligned with the sharpened bevel of the cannula; and the conductive shaft of the electrode conducts electricity to the cannula active tip via the conductive tubing that constructs the cannula shaft when the electrode conductive shaft is inserted into the lumen of the cannula conductive shaft tubing.
Figure 11B:
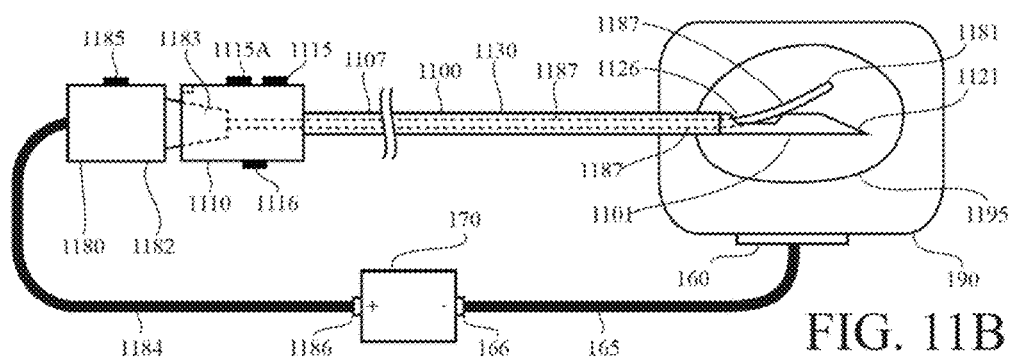
FIG. 11B is a schematic diagram showing the electrode and cannula of FIG. 11A wherein the electrode is fully inserted into the cannula, the first visible indicator is aligned with the second visible indicator, an RF generator conducts electricity to the electrode shaft, a monopolar RF heat lesion forms in tissue around the active tip of the cannula and the portion of the electrode conductive shaft extending out of the side outlet of the cannula active tip.
Figure 11C:
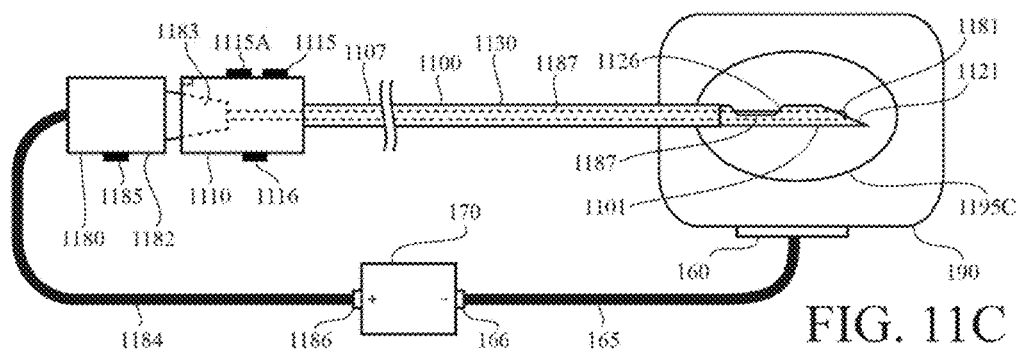
FIG. 11C is a schematic diagram showing the electrode and cannula of FIG. 11A wherein the electrode is fully inserted into the cannula, the first visible indicator is aligned with the third visible indicator, an RF generator conducts electricity to the electrode shaft, a monopolar RF heat lesion forms in tissue around the active tip of the cannula.
Figure 11D:
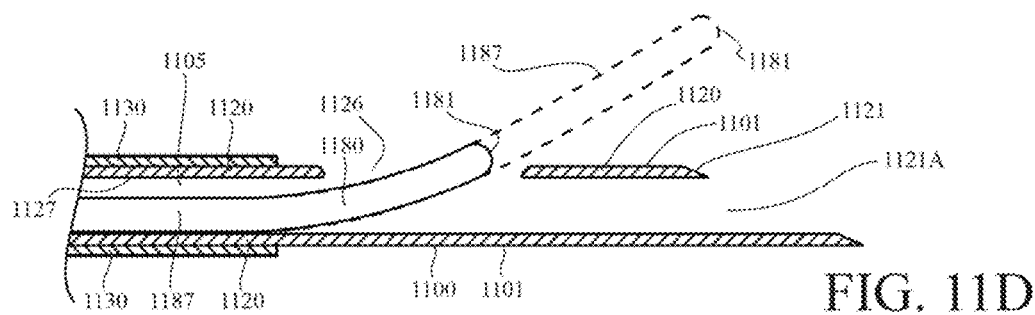
FIG. 11D is a schematic diagram showing a cross-sectional detail of the electrode and cannula of FIG. 11A wherein the electrode is shown in two positions having been inserted into the cannula lumen with the first visible indicator being aligned with the second visible indicator so that the electrode bend is oriented toward the cannula side outlet; wherein, in the first position, the electrode is not fully inserted into the cannula hub and the electrode tissue-penetrating end arcs toward the cannula side outlet due to the bend in the electrode shaft; wherein, in the second position the electrode is fully inserted into the cannula hub and the electrode tissue-penetrating end extends out of the cannula side outlet, as shown in FIG. 11B.
Figure 11E:
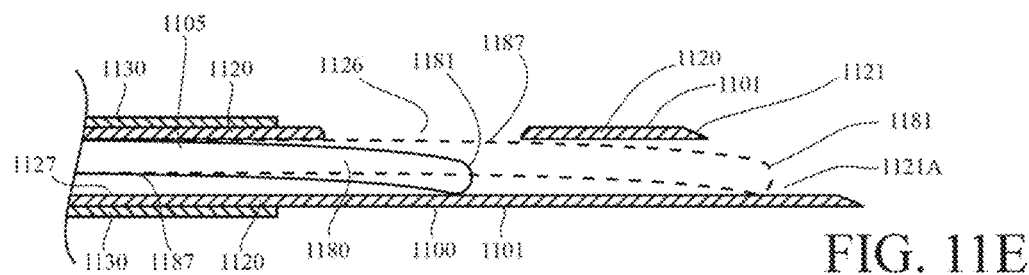
FIG. 11E is a schematic diagram showing a cross-sectional detail of the electrode and cannula of FIG. 11A wherein the electrode is shown in two positions within the cannula lumen with the first visible indicator being aligned with the visible visual indicator so that the electrode bend is oriented away from the cannula side outlet; wherein, in the first position, the electrode is not fully inserted into the cannula hub and the electrode tissue-penetrating end arcs away the cannula side outlet due to the bend in the electrode shaft; wherein, in the second position, the electrode is fully inserted into the cannula hub and the electrode tissue-penetrating end extends into the portion of the cannula lumen beyond the side outlet, as shown in FIG. 11C.

Referring now to FIG. 11, in accordance with several aspects of the present invention, FIG. 11 refers collectively to FIG. 11A, FIG. 11B, FIG. 11C, FIG. 11D and FIG. 11E. FIG. 11 presents schematically several embodiments of a side-outlet ablation system including a cannula 1100, a cannula stylet 1140, and an electrode 1180, wherein the electrode 1180 includes a bent shaft 1187 which can be inserted into the cannula lumen 1105 via the port 1112 in the cannula hub 1110, and whose shaft 1187 either extend into the distal portion of the cannula lumen 1105 distal to the cannula side opening 1126, or out from the cannula side opening 1126, depending on the rotationally orientations of the electrode 1180 relative to the cannula longitudinal axis. The electrode hub includes an indicia aligned with the shaft bend 1187A. The cannula hub 1110 includes two visually and tactilely distinguishable indicia, the first indicia including marker 1115A and marker 1115 being aligned with the cannula side opening 1126, the second indicia including marker 1116 being aligned opposite the cannula side opening 1126. When the electrode 1180 is inserted into the cannula 1000 such that the electrode indicia 1185 is aligned with the first cannula indicia 1115 and 1115A, the electrode shaft tip 11181 extends from the cannula side opening 1126, as shown in FIG. 11B and FIG. 11D. When the electrode 1180 is inserted into the cannula 1000 such that the electrode indicia 1185 is aligned with the second cannula indicia 1116, the electrode shaft tip 11181 extends into the portion of the cannula lumen within the cannula active tip 1101 distal to the side opening 1126, as shown in FIG. 11C and FIG. 11E. In some embodiments, the cannula shaft 1107 can include a bend near the distal end of the cannula shaft 1121, for example, within the length of the active tip 1101, or near the active tip 1101 in the cannula insulated shaft portion 1130. One advantage of the at least two distinguishable cannula hub indicia 1116 and 1115 & 1115A is that the user can ascertain the orientation of the side opening 1126 from when view any side of the cannula hub 1110, when the cannula shaft 1107 is inserted into bodily tissue, and can use said ascertained orientation to orient the electrode 1180 within the cannula 1100 for either side-outlet or within-lumen lesion formation. When the cannula 1100 is inserted into bodily tissue, as shown in FIG. 11B and FIG. 11C, it is not practical to remove the cannula from the tissue to ascertain the orientation of the side opening 1126. When the cannula 1100 is inserted into bodily tissue, as shown in FIG. 11B and FIG. 11C, it is not practical to view a particular side of the cannula hub 1110 in some cases.

Referring now to FIG. 11A, the cannula 1100, stylet 1140, and electrode 1180 are shown separately in a side view, the cannula 1180 is additionally shown in a proximal view from the proximal aspect of the cannula hub 1110, and the cannula 1100 is additionally shown in a top view. The cannula hub port 1112, stylet tab slot 1113, and lumen 1105 are shown as dotted lines through the cannula wall.

Referring now to FIG. 11B, an assembly of the RF electrode 1180 and RF cannula 1100 are shown in a side view, the electrode 1180 being fully inserted into the cannula 1100 with the electrode hub taper 1183 engaged with the cannula hub port 1112 and with the electrode indicia 1185 aligned with the cannula indicia 1115 and 1115A, the electrode shaft 1187 extending into bodily tissue 190 from the cannula side opening 1126, the assembly being inserted into bodily tissue 190 and operably connected to an RF generator 170 and ground pad 160 to produce an axially asymmetric monopolar heat lesion 1195 within the tissue 190 around the cannula active tip 1101 and the protruding portion of the cannula shaft 1187, the RF generator 170 controlling the RF output using the tissue temperature measured by the electrode tip sensor 1181. The portion of the electrode hub taper 1183 and the electrode shaft 1187 within the cannula 1110 are shown as dotted lines through the cannula wall.

Referring now to FIG. 11C, an assembly of the RF electrode 1180 and RF cannula 1000 are shown in a side view, the electrode 1180 being fully inserted into the cannula 1100 with the electrode hub taper 1183 engaged with the cannula hub port 1112 and with the electrode indicia 1185 aligned with the cannula indicia 1116, the electrode shaft tip 1181 extending past the side opening 1126 within the cannula lumen 1105 to align with the cannula distal bevel 1121, the assembly being inserted into bodily tissue 190 and operably connected to an RF generator 170 and ground pad 160 to produce an axially symmetric monopolar heat lesion 1195 within the tissue 190 around the cannula active tip 1101, the RF generator 170 controlling the RF output using the temperature at the cannula distal end 1121 measured by the electrode tip sensor 1181. The portion of the electrode hub taper 1183 and the electrode shaft 1187 within the cannula 1110 are shown as dotted lines through the cannula wall.

Referring now to FIG. 11D, a cross-sectional detail of the tissue-penetrating distal end of the cannula 1100 is shown with the electrode 1180 inserted within the cannula lumen 1105 and in two positions that shows the process by which the electrode tip 1181 exits the cannula side opening 1126. In the first position, the electrode shaft 1187 is shown in a solid line, and the electrode tip 1181 is positioned at the cannula side opening 1126 with the electrode tip bend 1187A directing the electrode tip 1181 toward and out of the side opening 1126. In the second position, which was achieved by advancing the electrode 1180 from the first position toward the cannula distal end 1121, the electrode shaft 1187 extends from the side opening 1126 of the cannula 1100. The electrode 1180 conducts an electrical potential from the generator connection 1186 to the electrode conductive shaft 1187 and then to the cannula active tip 1101 by physical contact between the electrode conductive shaft 1187 and the inner wall of conductive shaft tube 1120.

Referring now to FIG. 11E, a cross-sectional detail of the tissue-penetrating distal end of the cannula 1100 is shown with the electrode 1180 inserted within the cannula lumen 1105 and in two positions that shows the process by which the electrode tip 1181 extends past the cannula side opening 1126 into the distal length of the cannula shaft lumen 1105. In the first position, the electrode shaft 1187 is shown in a solid line, and the electrode tip 1181 is positioned at the cannula side opening 1126 with the electrode tip bend 1187A directing the electrode tip 1181 away from the side opening 1126 toward the opposite lumen wall. In the second position, which was achieved by advancing the electrode 1180 from the first position toward the cannula distal end 1121, the electrode shaft 1187 extends past the cannula side opening 1126 within the lumen 1105 to align with the distal cannula bevel 1121. The electrode 1180 conducts an electrical potential from the generator connection 1186 to the electrode conductive shaft 1187 and then to the cannula active tip 1101 by physical contact between the electrode conductive shaft 1187 and the inner wall of conductive shaft tube 1120.

Figure 12D:
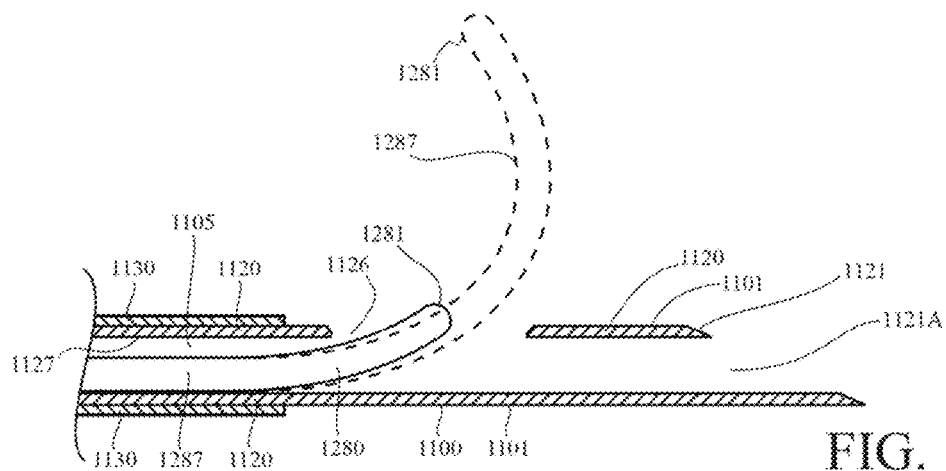
FIG. 12D is a schematic diagram showing a process by which the electrode tissue-piercing end can be advanced from the cannula hub and through the cannula lumen in order to exit the cannula lumen into bodily tissue to produce the configuration shown in FIG. 12B.
Figure 12E:
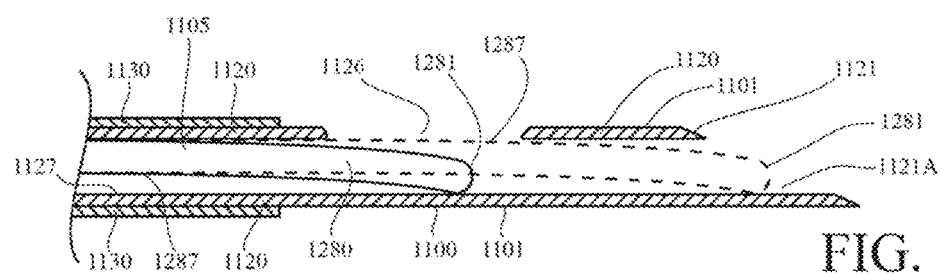
FIG. 12E is a schematic diagram showing a process by which the electrode tissue-piercing end can be advanced from the cannula hub and through the cannula lumen in order to enter the portion of the cannula lumen beyond the cannula side opening to produce the configuration shown in FIG. 12C.

Referring now to FIG. 12, in accordance with several aspects of the present invention, FIG. 8 refers collectively to FIG. 12A, FIG. 12B, FIG. 12C, FIG. 12D and FIG. 12E. FIG. 12 presents schematically several embodiments of a side-outlet ablation system including a cannula 1100, cannula stylet 1140, and an electrode 1280, wherein the electrode 1280 includes a hook-shaped bent shaft 1287 which can be inserted into the cannula lumen 1105 via the port 1112 in the cannula hub 1110, and whose shaft 1287 either extend into the distal portion of the cannula lumen 1105 distal to the cannula side opening 1126, or out from the cannula side opening 1126, depending on the rotationally orientations of the electrode 1280 relative to the cannula longitudinal axis. The electrode hub includes an indicia 1285 aligned with the shaft bend 1287A.

Referring now to FIG. 12A, the cannula 1100, stylet 1140, and electrode 1280 are shown separately in a side view, the cannula 1180 is additionally shown in a proximal view from the proximal aspect of the cannula hub 1110, and the cannula 1100 is additionally shown in a top view. The cannula hub port 1112, stylet tab slot 1113, and lumen 1105 are shown as dotted lines through the cannula wall.

Referring now to FIG. 12B, an assembly of the electrode 1280 and cannula 1100 are shown in a side view, the electrode 1280 being fully inserted into the cannula 1100 with the electrode hub taper 1283 engaged with the cannula hub port 1112 and with the electrode indicia 1285 aligned with the cannula indicia 1115 and 1115A, the electrode shaft 1287 extending into bodily tissue 190 from the cannula side opening 1126, the assembly being inserted into bodily tissue 190 and operably connected to an RF generator 170 and ground pad 160 to produce an axially asymmetric monopolar heat lesion 1295 within the tissue 190 around the cannula active tip 1101 and the protruding portion of the cannuls shaft 1287. The portion of the electrode hub taper 1283 and the electrode shaft 1287 within the cannula 1110 are shown as dotted lines through the cannula wall. One advantage of a hook-shaped electrode shaft bend 1287A is that tissue can be ablated 1295 at position more lateral to the cannula shaft 1287 than can be ablated by an electrode having a more gradual bend, such as bend 1187A of electrode 1100.

Referring now to FIG. 12C, an assembly of the electrode 1280 and cannula 1000 are shown in a side view, the electrode 1280 being fully inserted into the cannula 1100 with the electrode hub taper 1283 engaged with the cannula hub port 1112 and with the electrode indicia 1285 aligned with the cannula indicia 1116, the electrode shaft tip 1281 extending past the side opening 1126 within the cannula lumen 1105 to align with the cannula distal bevel 1121, the assembly being inserted into bodily tissue 190 and operably connected to an RF generator 170 and ground pad 160 to produce an axially symmetric monopolar heat lesion 1295 within the tissue 190 around the cannula active tip 1101. The portion of the electrode hub taper 1283 and the electrode shaft 1287 within the cannula 1110 are shown as dotted lines through the cannula wall.

Referring now to FIG. 12D, a cross-sectional detail of the tissue-penetrating distal end of the cannula 1100 is shown with the electrode 1280 inserted within the cannula lumen 1105 and in two positions that shows the process by which the electrode tip 1281 exits the cannula side opening 1126. In the first position, the electrode shaft 1287 is shown in a solid line, and the electrode tip 1281 is positioned at the cannula side opening 1126 with the electrode tip bend 1287A directing the electrode tip 1281 toward and out of the side opening 1126. In the second position, which was achieved by advancing the electrode 1280 from the first position toward the cannula distal end 1121, the electrode shaft 1287 extends from the side opening 1126 of the cannula 1100. The electrode 1280 conducts an electrical potential from the generator connection 1286 to the electrode conductive shaft 1287 and then to the cannula active tip 1101 by physical contact between the electrode conductive shaft 1287 and the inner wall of conductive shaft tube 1120.

Referring now to FIG. 12E, a cross-sectional detail of the tissue-penetrating distal end of the cannula 1100 is shown with the electrode 1280 inserted within the cannula lumen 1105 and in two positions that shows the process by which the electrode tip 1281 extends past the cannula side opening 1126 into the distal length of the cannula shaft lumen 1105. In the first position, the electrode shaft 1287 is shown in a solid line, and the electrode tip 1281 is positioned at the cannula side opening 1126 with the electrode tip bend 1287A directing the electrode tip 1281 away from the side opening 1126 toward the opposite lumen wall. In the second position, which was achieved by advancing the electrode 1280 from the first position toward the cannula distal end 1121, the electrode shaft tip 1281 extends past the cannula side opening 1126 within the lumen 1105 to align with the distal cannula bevel 1121. The electrode 1280 conducts an electrical potential from the generator connection 1286 to the electrode conductive shaft 1287 and then to the cannula active tip 1101 by physical contact between the electrode conductive shaft 1287 and the inner wall of conductive shaft tube 1120.

Referring now to FIG. 13, in accordance with several aspects of the present invention, FIG. 13 refers collectively to FIG. 13A, FIG. 13B, FIG. 13C, FIG. 13D, FIG. 13E, and FIG. 13F. FIG. 13 presents schematically several embodiments of a side-outlet ablation system including a cannula 100 and an electrode 1380, wherein the electrode 1280 includes a conductive shaft 1387 that has at least two bends 1387A and 1387B, shaft outer diameter D, injection port 1386A, flexible injection tube 1384A, and injection outflow tube 1384B. The first bend 1387A and the second bend 1387B produce a lateral deflection B of the shaft 1187 between bend 1387A and the bend 1387B. The second bend 1387B produces a lateral deflection W of the shaft 1187 between bend 1387B and shaft tip 1381. In this embodiment, the second bend 1387B reverses the lateral shaft deflection produced by the first bend 1187A. The length L of the shaft distal end affected by the bends 1387A and 1387B can be in the range 0 to 0.500 inches. The length L of the shaft distal end affected by the bends 1387A and 1387B can be in the range 0 to 5 mm. The length L of the shaft distal end affected by the bends 1387A and 1387B can greater than 0.500 inches. The injection tube 1384 can be flexible and enters the electrode hub 1832 to connect with injection outflow tube 1384B that protrudes from the electrode hub taper 1383. Aspects of the tube 1384A and tube 1384B within the electrode hub 1382 are depicted as dashed and dotted lines. In some embodiments, the cannula 100 can omit shaft bend 106 and have a substantially straight shaft 107. In some embodiments, the bends 1387A and 1387B can shape the shaft 1387 in a curved selected from the list: U-shaped, C-shaped, and S-shaped. In some embodiments, electrode 1380 can be used with a cannula that provides for exclusively side-outlet operation, such as cannulas 300, 400, or 500. In some embodiments, electrode 1380 can be used with a standard RF cannula not having a side outlet. In some embodiments, electrode 1380 can omit the injection features 1386A, 1384A, 1384B.

Figure 13A:
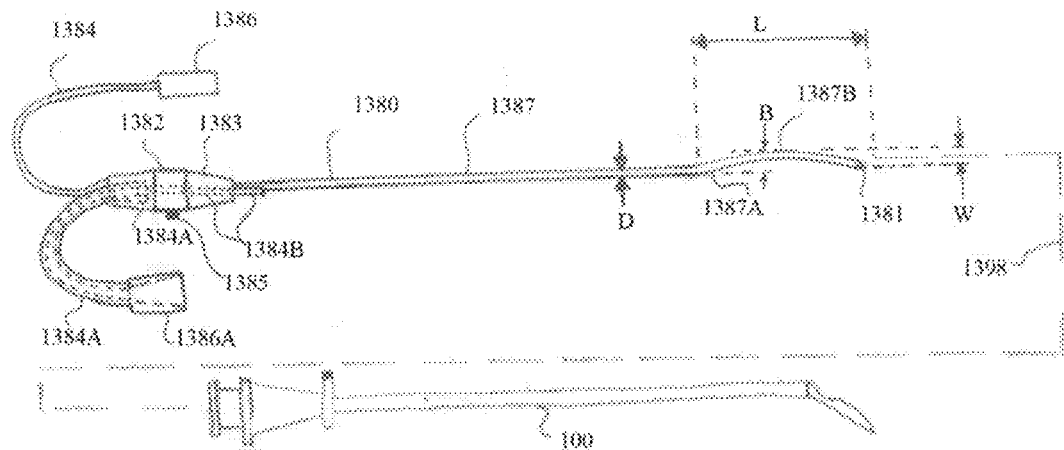
FIG. 13A is a schematic diagram showing an RF ablation system including a cannula and an electrode wherein the cannula includes a shaft and a hub; the cannula tubular shaft is constructed from conductive metal hypodermic tubing covered by electrical insulation except for an uncovered active tip portion at the cannula tissue-piercing end; the cannula shaft includes a bend; the cannula active tip includes a sharpened bevel point and a side opening to the cannula lumen; the cannula hub includes an side-opening marker aligned circumferentially with the side opening; the cannula hub includes a port to the lumen of the cannula hypodermic tubing; the electrode includes a conductive tissue-penetrating shaft, a temperature sensor at the tissue-penetrating tip of the electrode shaft, an injection port, a generator connection, and a hub; the electrode shaft is configured to be inserted into the cannula lumen and to conduct an electrical signal to the cannula hypodermic tubing by contact between electrode shaft and the inner surface of the cannula hypodermic tubing; the electrode shaft includes two bends near the tissue-penetrating end of the electrode shaft, the bends being configured to facilitate passage of the electrode shaft through the cannula lumen, to direct the tissue-penetrating tip of the electrode shaft out of the cannula side opening when tissue-penetrating tip of the electrode shaft is oriented toward the cannula side opening and the electrode shaft is advanced through the cannula lumen from the cannula hub to the cannula tissue-piercing end, and to direct the tissue-penetrating tip of the electrode shaft within the cannula lumen to the cannula sharpened bevel point when tissue-penetrating tip of the electrode shaft is oriented away from the cannula side opening and the electrode shaft is advanced through the cannula lumen from the cannula hub to the cannula tissue-piercing end; the electrode injection port connects to an outflow tube in the electrode hub configured to direct fluid injected through the port into the cannula lumen when the electrode shaft is fully inserted into the cannula lumen such that the electrode hub and the cannula hub are engaged; the generator connection conducts an electrical signal from an electrosurgical generator to the electrode conductive shaft, and transmits a temperature signal from the electrode temperature sensor to the electrosurgical generator; the electrode hub including a surface configured to engage with the port of the cannula hub when the electrode shaft is inserted to the cannula lumen via the cannula hub port; and the electrode hub includes a tip marker that indicates the orientation of the tissue-penetrating tip of the electrode shaft radial to the central axis of the electrode shaft when the electrode shaft has been inserted into the cannula lumen.

Referring now to FIG. 13A, the electrode 1380 and cannula are shown separately in an external side view. Line 1398 indicates how electrode 1380 can be inserted into the lumen 105 of cannula 100 to produce an assembled ablation probe system.

Figure 13B:
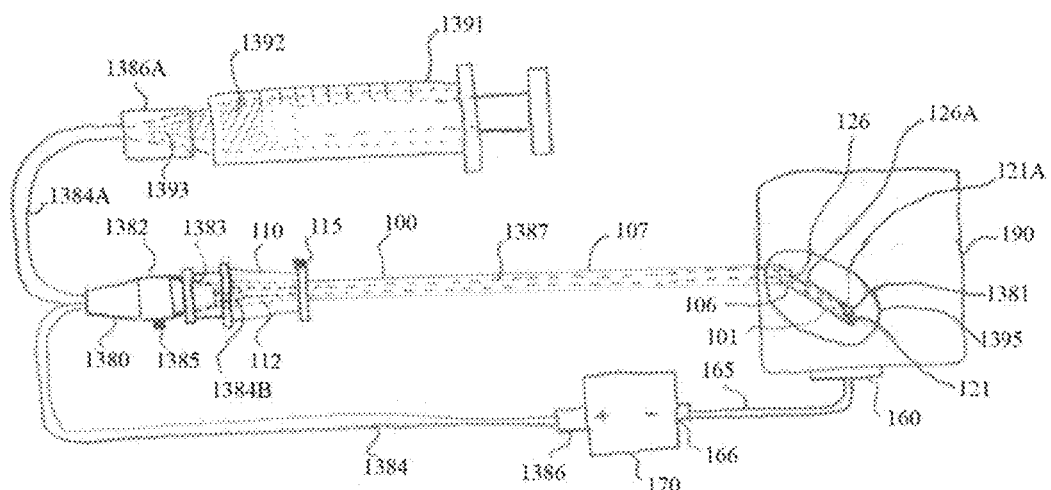
FIG. 13B is a schematic diagram showing a temperature-controlled, monopolar, RF heating of bodily tissue, and injection of fluid into the bodily tissue at the same time by means of the electrode and cannula of FIG. 13A, wherein the temperature sensor of the electrode is aligned with the cannula bevel within the cannula lumen, an RF generator uses the temperature signal from the temperature sensor to control the RF heating process around the cannula active tip, which conducts RF current from the RF generator to the bodily tissue.

Referring now to FIG. 13B, the electrode 1380 and cannula 100 are assembled and operably connected to an injection syringe 1391, RF generator 170, and ground pad 160 to inject fluid within in tissue 190 and to produce a temperature-monitored monopolar heat lesion 1395 in tissue 190 around the cannula active tip 101. The syringe 1391 injects fluid 1392 through port 1386A, tube 1384A, and tube 1384B from which the fluid outflow into the cannula lumen 105 and out from the cannula side opening 126 and cannula distal opening 121A into tissue 190, while the electrode shaft 1387 is inserted with the cannula lumen 105. Engagement of the male luer hub 1383 of the electrode 1380 with the female luer port 112 of the cannula 100 creates a fluid seal that prevents outflow of fluid 1392 from cannula hub port 112. The electrode shaft 1387 is rotationally oriented relative to the cannula axis (as indicated by the anti-alignment of electrode hub marker 1385 and cannula hub marker 115) so that the bend 1387B directs the electrode tip 1381 into the lumen within the cannula active tip 101 and aligned with the cannula bevel 121, the bends 1387A and 1387B in the elastic shaft 1387 press the conductive electrode shaft 1387 against the conductive inner lumen of the cannula shaft 105, and thus the output signal of the RF generator 170 is conducted to the cannula active tip 101 and the electrode 1380 measures the temperature at the cannula distal point 121 by means of the temperature sensor housed within the electrode distal tip 1381. RF heat lesioning and fluid injection can proceed at the same time using the assembly shown in FIG. 13C.

Figure 13C:
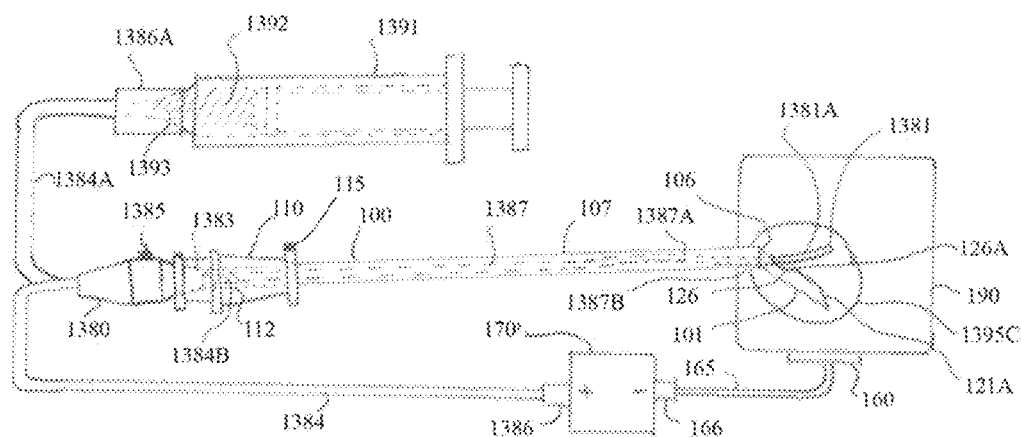
FIG. 13C is a schematic diagram showing a temperature-controlled, monopolar, RF heating of bodily tissue, and injection of fluid into the bodily tissue at the same time by means of the electrode and cannula of FIG. 13A, wherein a portion of the electrode conductive shaft extends into the bodily tissue from the side opening in the cannula active tip, the temperature sensor of the electrode measures the tissue temperature at the tissue-penetrating tip of the electrode shaft, an RF generator uses the temperature signal from the temperature sensor to control the RF heating process around the cannula active tip and the portion of the electrode conductive shaft extending into the bodily tissue, both of which conduct RF current from the RF generator to the bodily tissue.

Referring now to FIG. 13C, the rotational orientation of the electrode 1380 within cannula 100 shown in FIG. 13C is approximately 180 degrees from the rotational orientation of the electrode 1380 within cannula 100 shown in FIG. 13B. As such, in FIG. 13C, the electrode hub marker 1385 is aligned with the cannula hub marker 115, the shaft bend 1387B directs the distal tip 1381 of the electrode shaft 1387 out from the cannula side port 126 into tissue 190, the bends 1387A and 1387B in the elastic shaft 1387 press the conductive electrode shaft 1387 against the conductive inner lumen of the cannula shaft 105, the output signal of the RF generator 170 is conducted from the electrode shaft 1387 to the cannula active tip 101, and the electrode 1380 measures the tissue temperature within the RF heat lesion 1395C lateral to the cannula active tip 101. The heat lesion 1395C is not axially symmetric about the cannula active tip 101, but is rather biased in the direction of the extension of the electrode shaft 1381A into the tissue from the side opening 126. One advantage of the system presented in FIG. 13 is that fluid 1392 can be injected from more than one opening in the cannula active tip 101, thus distributing fluid injection around the active tip 101. Another advantage of the system presented in FIG. 13, that fluid that can enhance heat lesion size, such as an ionic fluid like saline or lidocaine, can be injected at the same time a heat lesion 1395C is generated using a side-outlet configuration, thereby increasing heat lesion size using two methods. In one aspect, the present invention relates to a process for generating large RF heat lesions comprising injecting fluid through an side-outlet cannula 100, and applying RF energy to both the active tip 101 of the cannula 100 and the portion of an electrode shaft 1381A protruding from the cannula side outlet 126, at the same time.

Figure 13D:
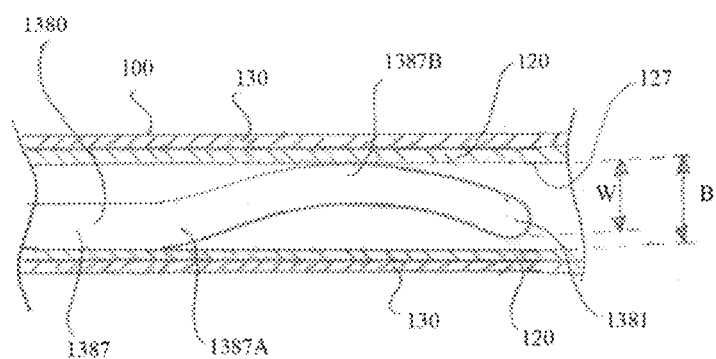
FIG. 13D is a schematic diagram showing a cross-sectional detail of two bends near the tissue-penetrating end of the electrode shaft within the lumen of the cannula, the bends pushing the electrode shaft against the walls of the cannula lumen and positioning and orienting the electrode tip within the lumen.

Referring now to FIG. 13D, the distal end of the electrode shaft 1387 is shown in a cross-sectional view of the shaft 107 of cannula 100. In this embodiment, the lateral shaft deflection B is configured to be slightly greater than the inner diameter of the cannula lumen 105 bounded by the inner wall 127 of conductive cannula shaft tube 120. As such, the electrode shaft 1387 presses against the lumen 127 thereby reliably conducting current from the electrode shaft 1387 to the cannula tube 120 even when the shaft diameter D is substantially smaller than the inner diameter of the cannula shaft tube 120. Because the second bend 1387B redirects the distal point 1381 of the electrode shaft 1387 away from the inner cannula wall 127, the electrode point 1381 does not dig into the cannula inner wall 127, thereby facilitating smooth insertion of the electrode 1380 into the cannula 100; this is advantage of including a second bend in the shaft of a bent-shaft electrode. The second bend 1387B is configured to produce a deflection W having a predetermined relationship to the deflection B so that the distal tip 1381 is positioned at a predetermined distance from the central axis of the cannula shaft 107; this is advantage of including a second bend in the shaft of a bent-shaft electrode. In the embodiment of FIG. 13D, deflection W is less than deflection B so that the electrode tip 1381 is held away from the cannula inner wall 127 to facilitate smooth sliding of the electrode 1380 through the cannula 100 and also allow the user select the orientation of the electrode tip 1381 about the cannula longitudinal axis by rotation of the electrode shaft 1387 within the cannula lumen 105. In embodiments wherein W is equal to or greater than B, and B is equal to or greater than the inner diameter of cannula tube 120, the electrode tip 1381 can touch the inner wall 127 of the cannula 100.

Figure 13E:
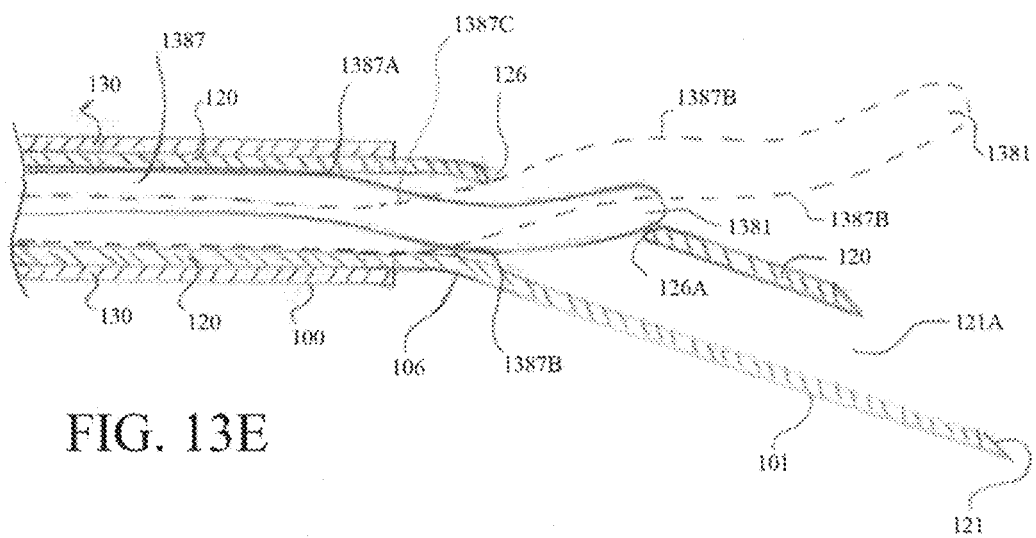
FIG. 13E is a schematic diagram showing a cross-sectional detail of the tissue-piercing end of the cannula shaft and two steps in a process of the electrode tissue-penetrating tip exiting the lumen of the cannula through the side opening in the cannula active tip.

Referring now to FIG. 13E, the distal end of the electrode shaft 1387 is shown in a cross-sectional view of the distal end of the shaft 107 of cannula 100. The electrode shaft 1387 is shown in a first position using a solid line, wherein the bends 1387A and 1387B directs the electrode tip 1381 out from the side outlet 126 in the cannula active tip 101. The electrode shaft 1387 is shown in a second position using a dashed line, wherein the electrode 1380 has been advanced distally from the first position so that the electrode shaft 1387 extends out of the cannula side outlet 126.

Figure 13F:
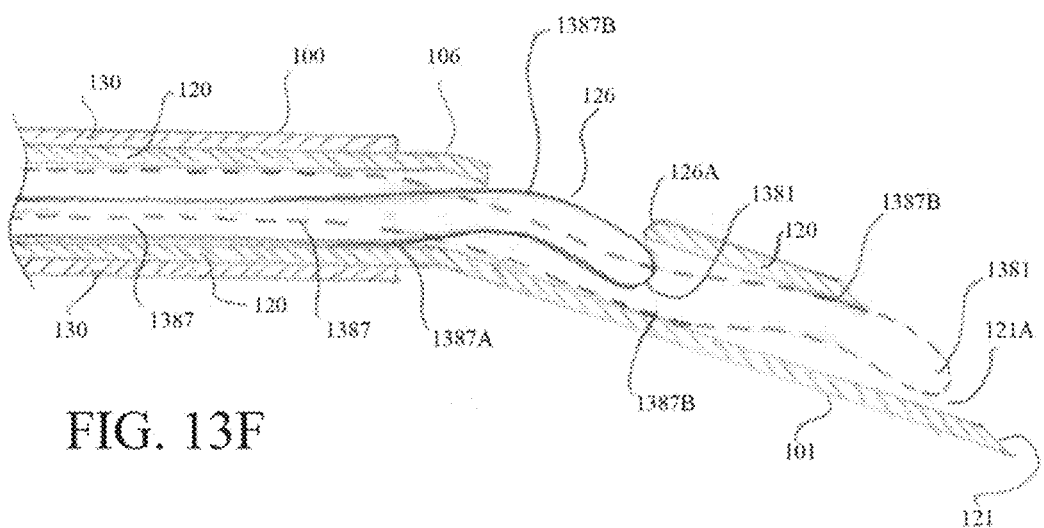
FIG. 13F is a schematic diagram showing a cross-sectional detail of the tissue-piercing end of the cannula shaft and two steps in a process of the electrode tissue-penetrating tip advancing within the cannula lumen and passing by the side opening in the cannula active tip in order to align with the tissue-piercing bevel of the cannula shaft.

Referring now to FIG. 13F, the distal end of the electrode shaft 1387 is shown in a cross-sectional view of the distal end of the shaft 107 of cannula 100. The electrode shaft 1387 is shown in a first position using a solid line, wherein the bends 1387A and 1387B directs the electrode tip 1381 away from the side outlet 126 in the cannula active tip 101 and toward the cannula lumen distal to the side opening 126 within the active tip 101. The electrode shaft 1387 is shown in a second position using a dashed line, wherein the electrode 1380 has been advanced distally from the first position so that the electrode shaft 1387 is within the cannula active tip 101 and the electrode tip 1381 aligns with the cannula distal bevel 121.

Figure 14A:
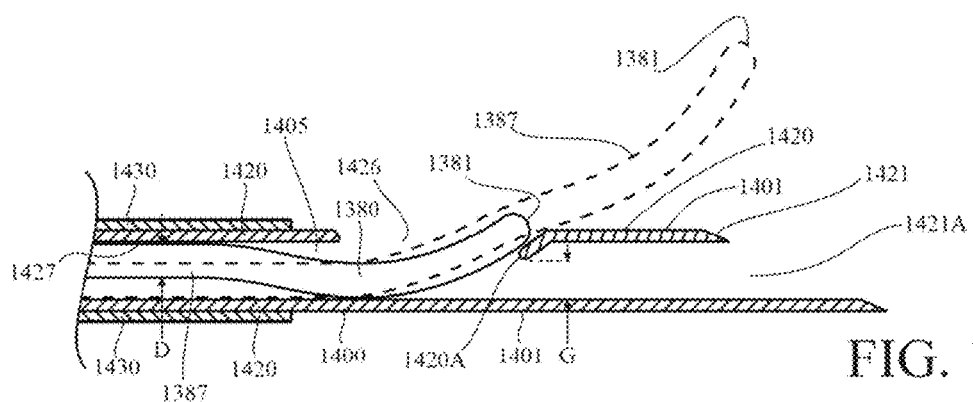
FIG. 14A is a schematic diagram showing a cross-sectional detail an cannula and the electrode of FIG. 13A, wherein the cannula includes a conductive, tubular, substantially-straight shaft having a proximal end and a distal end, electrical insulation covering the proximal portion of the shaft, an active tip at the distal end of the shaft, a tissue-penetrating bevel at the distal point of the shaft, a lumen within the shaft configured to admit the electrode shaft, and a side opening to the lumen within the active tip having a distal aspect that deflects into the cannula lumen; and wherein the electrode is shown in two positions during a process of the electrode tissue-penetrating tip extending from the cannula side opening into bodily tissue.
Figure 14B:
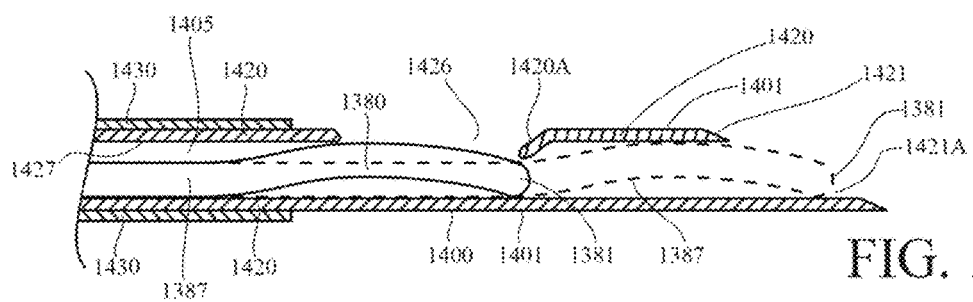
FIG. 14B is a schematic diagram showing a cross-sectional detail of a cannula and the electrode of FIG. 14A wherein the electrode is shown in two positions during a process of the electrode tissue-penetrating tip passing by the cannula side opening to enter the cannula lumen distal to the cannula side opening.

Referring now to FIG. 14, in accordance with several aspects of the present invention, FIG. 13 refers collectively to FIG. 14A and FIG. 14B. FIG. 14 shows the distal end of electrode 1380 in a cross-sectional view of straight-tip, side-outlet cannula 1400, the cannula 1400 having a side outlet 1426 to the cannula lumen 1405. The side outlet 1426 includes at its distal edge a flap 1420A of the cannula shaft tube 1420 into the lumen 1405. The flap is configured to facilitate direction of the electrode shaft 1387 out of the side outlet 1426 (as depicted in FIG. 14A), particularly when the second shaft deflection W is smaller than the first shaft deflection B (as depicted in FIG. 13D) so that the electrode tip 1381 does not push directly against the inner wall of the cannula lumen 1405. The distance G between the flap 1420A and the opposite inner wall of the cannula lumen 1405 is configured to be larger than then diameter D of the conductive, elastic electrode shaft 1387, so that the electrode shaft 1387 can be advanced distal to the flap 1420A within the cannula lumen 1405 (as depicted in FIG. 14B). The user can select the branch of the lumen 1405 through which the electrode shaft 1387 is advanced by selection of the rotationally orientation of the electrode within the cannula lumen 1405, wherein the side outlet 1426 is a first branch of the lumen 1405, and the lumen distal to flap 1420A is a second branch of the lumen 1405. In some embodiments, the shaft of cannula 1400 can include a bend. In some embodiments, the gap G can be smaller than the shaft diameter D so that the electrode shaft can only be advanced out of the side outlet 1426. In some embodiments, the electrode 1380 only includes a first bend 1387A and omits the second bend 1387B.

Figure 15A:
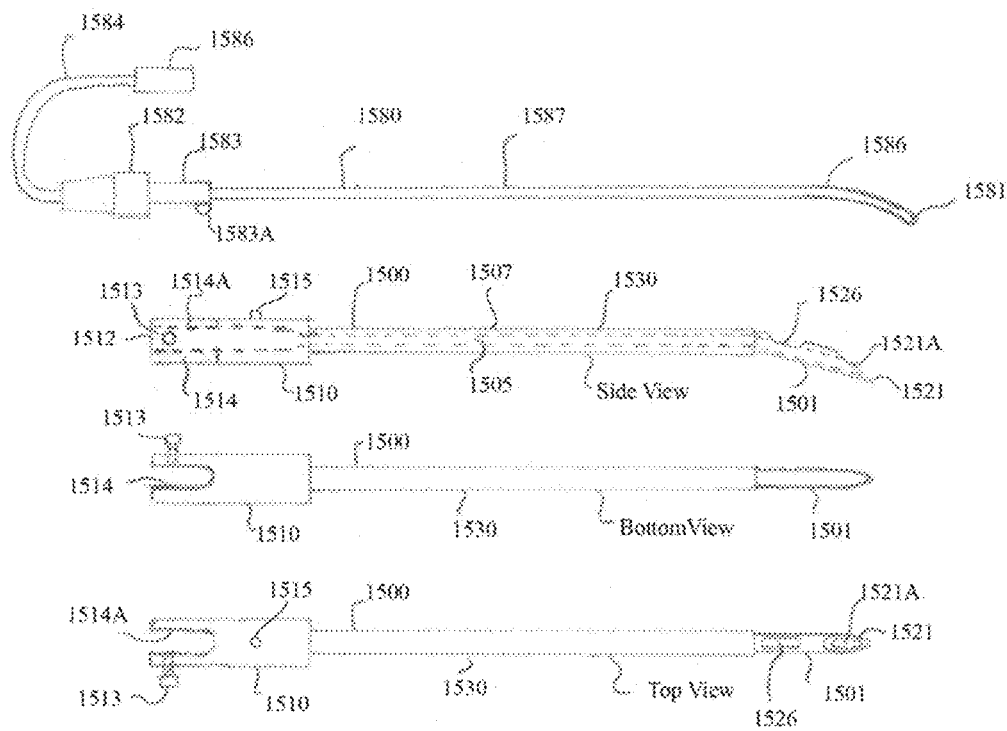
FIG. 15A is a schematic diagram showing an electrosurgical system including an electrode and a cannula, wherein the electrode includes a curved conductive shaft, a generator connection, a temperature sensor at the tissue-penetrating end of the shaft, a hub, and a tab on the hub; the cannula includes a conductive tubular shaft covered by electrical insulation except for the active tip at the tissue-penetrating end of the cannula shaft, a hub at the non-tissue-penetrating end of the cannula shaft, a lumen through the cannula hub and cannula shaft through which the electrode shaft can slide, a port to the lumen in the hub into which the electrode hub can slide, a side opening to the lumen in the active tip, an end opening to the lumen at the tissue-penetrating end of the active tip, a set screw in the hub configured to clamp the electrode hub within the hub port, a side-opening slot in the hub into which the electrode hub key can slide to orient the tissue-penetrating end of the electrode shaft toward the cannula side opening, an end-opening slot in the hub into which the electrode hub key can slide to orient the tissue-penetrating end of the electrode shaft away from the side opening and toward the cannula end opening; the cannula hub port and the electrode hub being configured to allow the user to adjust the position of electrode shaft within the cannula lumen, providing for a first configuration in which the tissue-penetrating end of the electrode shaft extends out of the side opening of the cannula shaft, a second configuration in which the tissue-penetrating end of the electrode shaft is within the cannula lumen and aligned with the tissue-penetrating end of the cannula shaft, and a third position in which the tissue-penetrating end of the electrode shaft extends out of the end opening of the cannula shaft; and the electrode conductive shaft conducts an electrical signal from the generator connection to the cannula active tip when the electrode shaft is positioned in the cannula lumen, including in the first, second, and third configurations.
Figure 15B:
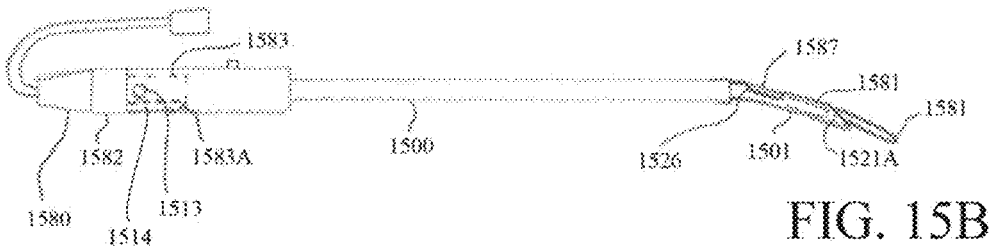
FIG. 15B is a schematic diagram showing the electrode and cannula of FIG. 15A in an example of the second configuration and in an example of the third configuration.
Figure 15C:
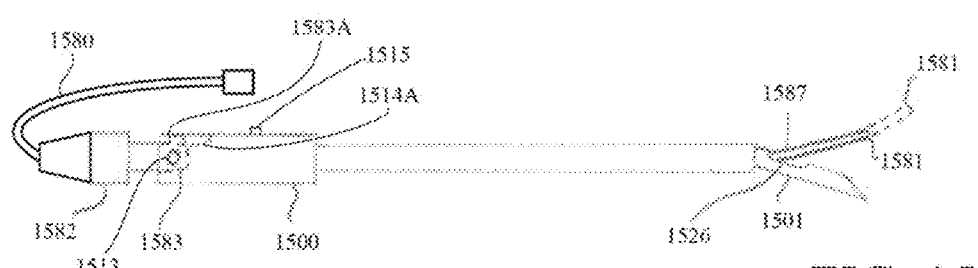
FIG. 15C is a schematic diagram showing the electrode and cannula of FIG. 15A in two examples of the first configuration.

Referring now to FIG. 15, in accordance with several aspects of the present invention, FIG. 15 refers collectively to FIG. 15A, FIG. 15B, and FIG. 15C. FIG. 15 shows an RF electrode 1580 and an RF cannula 1500. In some embodiments, the cannula 1500 can be used with a stylet. The electrode includes a generator connection 1586 that conducts RF current from an RF generator 170 to the conductive electrode shaft 1587, a hub 1582 including a distal slide element 1583 and an tab 1583A on one side of the hub, an elastic conductive metal shaft 1587 having a bend 1586 near the distal tissue-penetrating end of the shaft, a temperature sensor 1581 at the shaft distal tip that is conducted to an RF generator 170 by connection 1586. The cannula 1500 includes a hub 1510, a set screw 1513 in the hub, a first slot 1514 in the hub 1510 aligned opposite the side opening 1526, a second slot 1514A aligned with the side opening 1526, a marker 1515 on the hub aligned with the second slot 1514A, a shaft 1507 including an electrically-insulated proximal portion 1530 and a electrically-conductive distal active tip portion 1501, a lumen 1505 through the cannula shaft 1507, a proximal opening 1512 to the lumen 1505 in the cannula hub 1510, a distal opening 1521A to the lumen 1505 in the cannula sharp bevel point 1521, a side opening 1526 to the lumen 1505 in the wall of the active tip 1501. The electrode shaft 1587 can be inserted into the cannula lumen 1505 through the cannula hub 1510 and electrode shaft 1587 conducts RF current from the generator connection 1586 to the cannula active tip 1501 by contact between the electrode shaft 1587 and aspect of the cannula lumen 1505. When the electrode 1580 is inserted into the cannula 1500, the straight side walls of electrode hub slide 1583 engage with the inner side walls of port 1512, and the user physician can clamp the electrode in a position by tightening the set screen 1513, which clamps the electrode hub slide 1583 against the wall of port 1512. The user can release the electrode 1580 from the cannula 1500 by untightening the screw 1513, and move the electrode hub 1582 relative to the cannula hub 1510 to move the electrode distal tip 1581 relative to cannula distal tip 1521. The electrode slide 1583 can be positioned within the cannula hub port 1512 over a range of longitudinal positions, ranging from the position where the electrode hub slide 1583 is at the proximal end of the port 1512 (one example of this is shown in FIG. 15B), to the position where the electrode hub 1582 stops against the cannula hub 1510 (one example of this is shown in FIG. 15C). The electrode hub tab 1583A prevents the electrode hub slide 1583 from entering the cannula hub port 1512 unless the hub tab 1583A enters either slot 1514 or 1514A. When the electrode 1580 is inserted into the cannula 1500 such that the electrode hub tab 1583A enters cannula hub slot 1514, the electrode shaft bend 1586 directs the electrode tip 1581 away from the cannula side opening 1526 toward the distal opening 1521A. When the electrode 1580 is inserted into the cannula 1500 such that the electrode hub tab 1583A enters cannula hub slot 1514A, the electrode shaft bend 1586 directs the electrode tip 1581 toward the cannula side opening 1526. In some embodiments, the cannula shaft 1507 includes a bend near the distal end (as shown in FIG. 15). In some embodiments, the shaft 1507 can be substantially straight over its entire length.

Referring now to FIG. 15A, the electrode 1580 and the cannula 1500 are shown separately, the electrode in a side external view, and the cannula in a side, a top, and a bottom view. The lumen 1505 is shown within the cannula 1500 using dotted lines in the Side View of the cannula 1500. The distal aspect of the slot 1514 and the distal aspect of the slot 1514A are shown through the wall of the hub 1510 as dotted lines in the Side View of cannula 1500.

Referring now to FIG. 15B, an assembly of the electrode 1580 and the cannula 1500 is shown in a side external view, wherein the electrode hub slide 1583 is indicated by dashed lines within the cannula hub slot 1512. The assembly is shown in a first configuration wherein the electrode 1580 is fully inserted into the cannula 1500, the electrode hub tab 1583A engages with cannula hub slot 1514, and the distal end of the electrode shaft 1581 extend out of the cannula distal opening 1521A to form a combined active tip from which RF current can be delivered and which includes both the cannula active tip 1501 and the portion of the conductive electrode shaft 1587 extending out of the cannula distal opening 1521A. A second configuration of the assembly is shown by another achievable position of the electrode distal end 1581, which is depicted by a dotted line within the cannula active tip 1501. In the second configuration, the cannula active tip 1501 is the entire active tip of the assembly. The second configuration of the assembly can be achieved by sliding the electrode 1580 toward the cannula hub with the electrode hub slide 1583 to a more proximal position within the cannula hub slot 1512. The assembly of the cannula 1500 and electrode 1580 can be used to achieve a variety of combined active tip length by repositioning the electrode hub slide 1583 within the cannula hub port 1512.

Referring now to FIG. 15C, the assembly of the electrode 1580 and the cannula 1500 is shown in a side external view, wherein the portion of the electrode hub slide 1583 within the cannula hub slot 1512 is indicated by dashed lines within the cannula hub slot 1512. The assembly is shown in a third configuration wherein the electrode 1580 is partially inserted into the cannula 1500, the electrode hub tab 1583A engages with cannula hub slot 1514A, and the distal end of the electrode shaft 1581 extends out of the cannula side opening 1526 to form a combined active tip from which RF current can be delivered and which includes the cannula active tip 1501 and the portion of the conductive electrode shaft 1587 extending out of the cannula side opening 1521A. The assembly of the cannula 1500 and electrode 1580 can be used to achieve a variety of side-outlet tip configurations having a variety of side-outlet tip extensions by repositioning the electrode hub slide 1583 within the cannula hub port 1512. One example of another side-outlet tip configuration is indicated by dashed-line depiction of the electrode tip 1581.

Figure 16A:
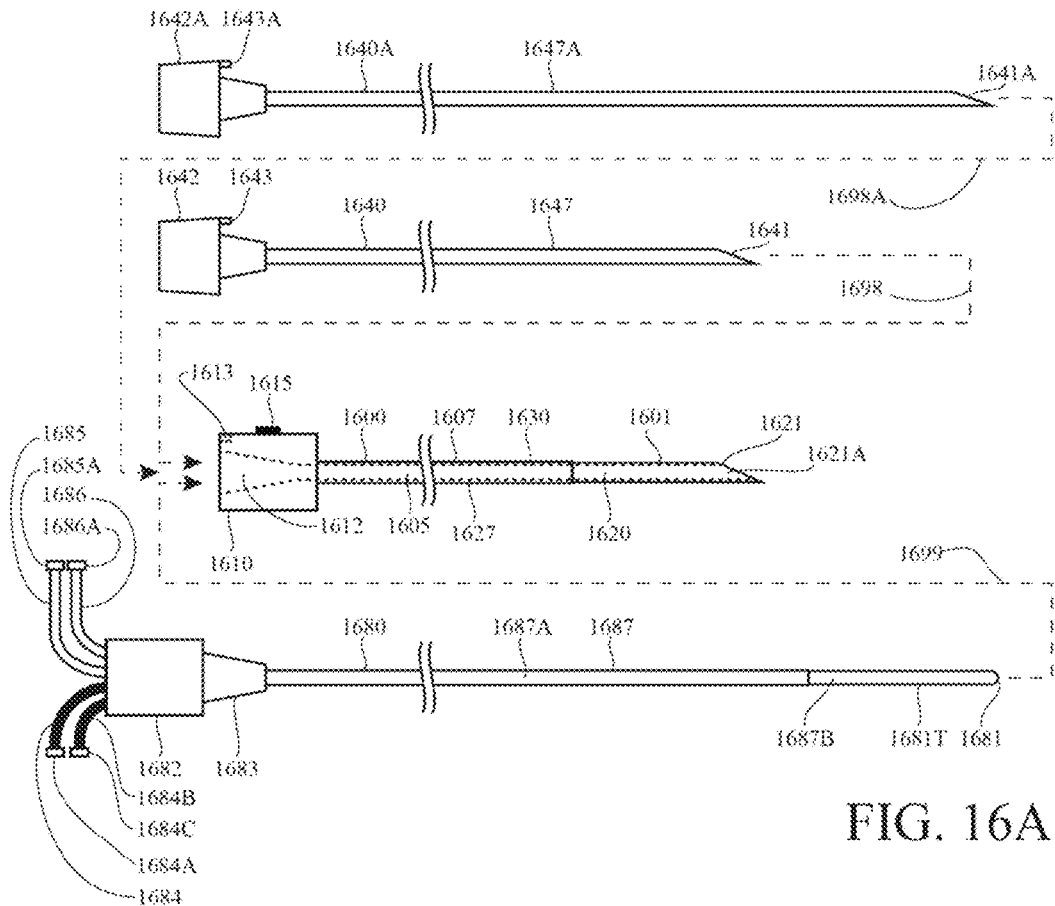
FIG. 16A is a schematic diagram showing a coaxial bipolar cooled RF system including a blunt-tip internally-cooled RF electrode, an straight RF cannula, and a tissue-piercing extension stylet wherein the extension stylet is configured to extend through the cannula shaft through a lumen in the cannula shaft and out from an opening in the cannula tissue-piercing bevel to make a path in bodily tissue for the electrode, the cannula includes an electrically-insulated shaft except for a conductive active tip at the tissue-piercing end of the cannula shaft, the electrode includes an electrically-insulated shaft except for a conductive active tip at the tissue-penetrating end of the electrode shaft, the electrode includes a first generator connection that conducts a first RF potential from an RF generator to the electrode active tip, the electrode includes a second generator connection that conducts a second RF potential form the RF generator to the cannula active tip via an electrical connection between the electrode hub and the cannula hub, and the electrode is configured extend through the lumen of the cannula shaft and out from the opening in the cannula tissue-piercing bevel such that the electrode active tip is spaced from and electrically-isolated from the cannula active tip except via tissue in which the electrode active tip and the cannula active tip are both positioned.
Figure 16B:
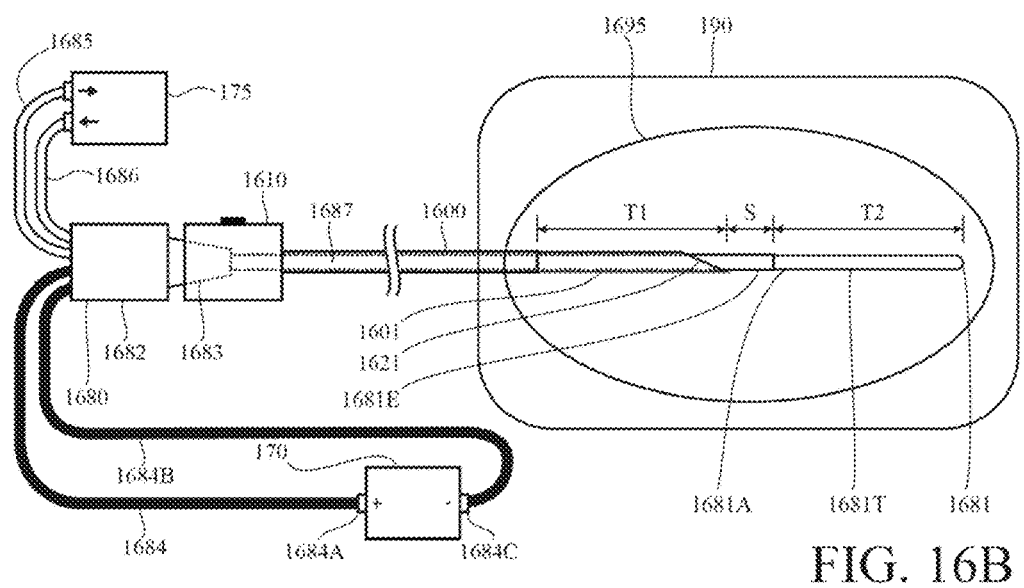
FIG. 16B is a schematic diagram showing the bipolar cooled RF system of FIG. 16A creating a bipolar lesion in bodily tissue by passing RF current between the electrode active tip and the cannula active tip.

Referring now to FIG. 16, in accordance with several aspects of the present invention, FIG. 16 refers collectively to FIG. 16A, FIG. 16B, and FIG. 15C. FIG. 16 shows a system for coaxial bipolar cooled RF ablation including an internally-cooled RF electrode 1680, RF cannula 1600, cannula stylet 1640, and extension stylet 1640A. The electrode 1680 includes a generator connection 1684A that conducts an RF signal to the electrode active tip 1681T from an RF generator 170, and transmits a temperature signal from a temperature sensor 1687T at the distal end 1681 of the electrode shaft 1687 to the RF generator 170. The electrode shaft 1687 includes active tip 1681T at the shaft distal end, and is covered by electrical insulation 1687A over the shaft proximal length. The electrode includes a reference connection 1684C that conducts a reference potential from the RF generator 170 to the cannula active tip 1601 by means of conductive engagement between a conductive element in the electrode hub luer 1683 and a conductive element in the cannula hub port 1612 when the electrode 1680 is fully inserted into the cannula 1600 as indicated by arrow 1699. The electrode distal tip 1681 is blunt. The cannula 1600 includes hub 1610, insulated shaft portion 1630, active tip 1601, a lumen 1605 through the shaft, a proximal lumen port 1612 in the hub 1610, a distal lumen opening 1621A in the sharpen bevel point 1621 of the cannula shaft 1607. Stylet 1640 inserts into cannula lumen 1605 as indicated by arrow 1698, and the stylet bevel 1641 aligns with the cannula bevel 1621 to form a solid bevel tip when stylet tab 1643 engages with cannula hub slot 1613. When the extension stylet 1640A is fully inserted into the cannula lumen 1605 (arrow 1698A) such that the stylet cap 1642A abuts the cannula hub 1610, the extension stylet shaft 1647A extends out of the distal opening 1621A of the cannula lumen 1605 by the same length as does the electrode 1680 when the electrode 1680 is fully inserted into the cannula lumen 1605; thereby the extension stylet can pierce tissue ahead of the cannula tip 1621 to create a path through which the electrode 1680 can slide after the extension stylet 1640A is remove from the cannula 1600. In some embodiments, the extension stylet 1640A can have a longer shaft 1647A to create a tissue path longer than the electrode shaft 1687. In some embodiments, the extension stylet 1640A can have a short shaft 1647A to create a tissue path shorter than the electrode shaft 1687.

Referring now to FIG. 16A, internally-cooled RF electrode 1680, RF cannula 1600, cannula stylet 1640, and extension stylet 1640A are shown separately in an external side view. The system presented in FIG. 16 can be used in a process including inserting the assembly of the cannula 1600 and stylet 1640 into bodily tissue, removing the stylet 1640 from the cannula 1600, inserting the extension stylet 1640A through the cannula into tissue distal of the cannula distal tip 1621, removing the extension stylet 1640A from the cannula, inserting the electrode 1680 through the cannula 1600 and the tissue path created by the extension stylet 1640A, cooling the active tip 1681T of the electrode 1680 and the active tip 1601 of the cannula 1600 by circulation of coolant through the electrode shaft 1687, connecting the electrode 1600 to a first output pole of an RF generator via connection 1684A, connecting the electrode 1600 to a second output pole of an RF generator via connection 1684C, applying an RF potential across the first and the second output poles of the RF generator to conduct RF current through the tissue between the cannula active tip 1601 and the electrode active tip 1681 and thereby heat the tissue by ohmic heating. The rounded distal end of the electrode shaft 1681 is advantageous to provide for a minimal wall thickness, and thus maximal cooling, at that location where electric fields and tissue temperatures can be highest.

In another embodiments, the electrode point 1681 can be sharp. Coolant flow within electrode shaft 1687 cools both the electrode active tip 1681T and the cannula active tip 1601.

Referring now to FIG. 16B, internally-cooled RF electrode 1680 and RF cannula 1600 are assembled and operably connected to an RF generator 170 and coolant pump system 175 to form an RF heat lesion 1695 in tissue 190 by flow of RF current from the cannula active tip 1601 to the electrode active tip 1681 T through the tissue 190. The electrode 1680 is fully inserted into the cannula 1600 and the conductive portion of the electrode luer hub 1683 is engaged with the conductive port 1612 of the cannula hub 1610. The portions of the electrode luer hub 1683 and the electrode shaft 1683 within the cannula 1600 are shown as dotted lines through the cannula side walls. The active tip length T1 of the cannula active tip 1601 is equal to the active tip length of the electrode active tip 1681T to equalized heating between both active tips. In some embodiments, T1 and T2 and be unequal to provide for unbalanced heating between the active tips, or to compensate for enhanced cooling of the electrode active tip 1681T due to closer proximity to the coolant within the electrode shaft 1687. The spacing S between the electrode active tip 1681 T and cannula active tip 1601 is configured to be large enough to prevent so much current focus in the tissue lateral to the spacing that tissue heating around the rest of the active tips is limited. In some embodiments, T1 and T2 can each be selected from range 5 mm to 30 mm. In some embodiments, each of T1 and T2 can either be less than 5 mm or greater than 30 mm. In some embodiments, the spacing S can be a value selected from a range in the list: less than 5 mm, 5 mm to 20 mm, greater than 20 mm.

Figure 16C:
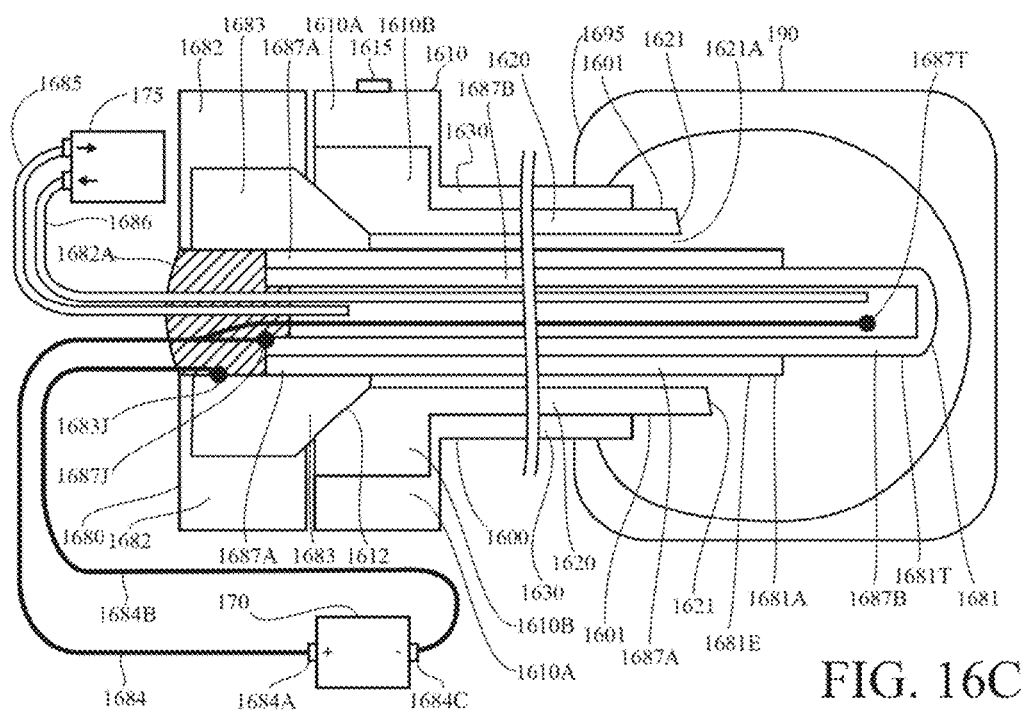
FIG. 16C is a schematic diagram showing the internal construction of the electrode and cannula of FIG. 16A.

Referring now to FIG. 16C the assembly of electrode 1680 and cannula 1600 is presented schematically in an assembled, operational configuration in which an RF generator 170 and coolant pump 175 are used to generate a bipolar RF heat lesion 1695 in bodily tissue 190, into which the electrode 1680 and cannula 1600 are inserted. This configured as achieved by a process including inserting the cannula 1600 into the bodily tissue, inserting the electrode 1680 into the cannula lumen 1605, pumping coolant through the electrode shaft 1687 by means of pump 175, and applying an RF current through the tissue 190 between the cannula active tip 1601 and the electrode active tip 1681T and through the conductive interface between the electrode taper 1683 and the cannula port 1612. The construction of the cannula 1600 is similar to the embodiment of the cannula 900 shown in FIG. 9D. The construction of the electrode 1680 is similar to the electrode 980 shown in FIG. 9D, except that the distal tip of electrode 1600 is blunt.

In some embodiments, each of the cannulas, electrodes, and stylets presented in FIG. 1 through 16 can be disposable (eg sterile packed and single use only) or reusable (eg autoclavable). In some embodiments, each of the cannulas, electrodes, and stylets presented in FIG. 1 through 16 can have different construction that still provide the key functional and operational features of the present invention; for example, the shaft 107 of cannula 100 can be constructed from an elongated electrically-insulative tube at whose distal end is mounted a conductive active tip tube, rather than covering the proximal portion 130 of a single electrically-conductive tube 120 with electrical insulation 130; for example, different lengths of the electrode shaft 187 can be constructed from different pieces having different physical characteristics; for example, the active tip of a probe (eg a cannula or electrode) can be constructed from a conductive ring covering the probe shaft. In some embodiments, each of the electrodes or cannulas presented in FIG. 1 through 16 can be adapted to in more than one conductive active tip. In some embodiments, each of the systems presented in FIG. 1 through 16 can be adapted to deliver one or more forms of electrical signals selected from the list: direct current, alternating current, radiofrequency, a combination of radiofrequency and direct current, microwave, stimulation, nerve stimulation, muscle, low frequency, high frequency, and combinations thereof. In some embodiments, each of the electrodes presented in FIG. 1 through 16 can be adapted for either temperature-controlled ablation or non-temperature-controlled ablation, or both. In some embodiments, each of the electrodes presented in FIG. 1 through 16 can be adapted to include internal cooling of the electrode shaft, and to include connections for inflow and outflow of internal coolant. In some embodiments, each of the electrodes and cannula presented in FIG. 1 through 16 can be adapted to include electrical insulation covering a part of the electrode conductive shaft, and the assembly of the cannula and electrode can operate as a bipolar ablation probe system. In some embodiments, each of the systems presented in FIG. 1 through 16 can be adapted for application of monopolar signals, bipolar signals, multi-polar signals, and combinations and sequences thereof, in concert with other probes. In some embodiments, each of the cannulae presented in FIG. 1 through 16 can be adapted so that its cannula shaft is completely electrically insulated and an extension of an electrode through open opening out of the cannula lumen solely conducts electricity to bodily tissue. In some embodiments, each of the cannulae presented in FIG. 1 through 16 can be adapted so that the cannula active tip is positioned at a position along its shaft that is not at the most distal point of the cannula shaft. In some embodiments, each of the electrodes presented in FIG. 1 through 16 can be adapted so that more than one length of the electrode shaft is covered by electrical insulation to form an active tip not at the most distal point of the electrode shaft. In some embodiments, each of the bipolar electrode and cannula assemblies presented in FIG. 1 through 16 can be adapted for a two-active-tip monopolar operation wherein both the electrode active tip and the cannula active tip are connected to the same electrical potential and referenced to a common reference electrode, such as a ground pad. In some embodiments, each of the bipolar electrode and cannula assemblies presented in FIG. 1 through 16 can be adapted for a two-active-tip monopolar-bipolar operation wherein the active tip of the electrode is connected to a first electrical potential, the active tip of the cannula is connected to a second electrical potential, and a reference electrode is connected to a third electrical potential, and the electrode active tip, the cannula active tip, and a reference electrode are all applied to the same bodily tissue. In some embodiments, each of the systems presented in FIG. 1 through 16 can be adapted for tissue ablation in one or more of a wide variety of clinical contexts including tissue coagulation, pain management, tumor ablation, cardiac ablation, tissue devascularization, open surgical procedures, percutaneous surgical procedures, laparoscopic surgical procedures, facet denervation, SIJ deneravation, pulsed RF neuromodulation, pulsed RF lesioning, preparation of collapsed bone for injection of bone cement, lesioning of intravertebral nerves, lesion of intra-bone structures. In some embodiments, each of the systems presented in FIG. 1 through 16 can be adapted for tissue ablation in any one or more parts of the human body, including the spine, bone, spinal nerve, peripheral nerve, knee nerve, hip nerve, shoulder nerve, foot nerve, hand nerve, carpel tunnel, sympathetic nerve, trigeminal nerve, medial branch nerve, sacral lateral branch nerve, brain, heart, liver, kidney, lung, pancreas, prostate, adrenal gland, thyroid, gall bladder, vertebral body, intervertevral nerve, basivertebral nerve, an intervertebral disc, nerve in an intervertebral disc, posterior annulus of an intervertebral disc, nucleus of the intervertebral disc, muscle, osteoid osteoma. In some embodiments, the generator 170 can be connected to multiple electrodes and probes and/or multiple ground pads at the same time. In some embodiments, the generator 170 can include more than two output poles. In some embodiments, the generator 170 can produce a nerve-stimulation signal.

A number of embodiments of the invention have been described. Nevertheless, it will be understood that various modifications may be made without departing from the spirit and scope of the invention. Accordingly, other embodiments are within the scope of the following claims. What we claim are the following:

What is claimed is:

1. A system for tissue ablation including an electrosurgical generator, a cannula and an electrode, the cannula including an elongated shaft having a proximal end and a distal end, the cannula shaft including an electrically-conductive active tip distal to an electrically-insulated cannula shaft portion, the cannula shaft including a lumen extending from a proximal opening at the proximal end of the shaft to an exit opening within a distal portion including the distal end of the cannula shaft, the cannula including a cannula hub at the proximal end of the shaft of the cannula, the electrode including an electrode shaft having a proximal end and a distal end, the electrode shaft including an electrically-conductive active tip distal to an electrically-insulated electrode shaft portion, the electrode including an electrode hub at the proximal end of the shaft of the electrode, the electrode conducting a first electrical potential from the electrosurgical generator to the electrode active tip, wherein the electrode and the cannula are configured to be assembled by inserting the electrode shaft into the cannula lumen through the proximal opening such that engagement of the electrode hub with the cannula hub conducts a second electrical potential from the electrosurgical generator to the cannula active tip via the electrode, the electrode active tip and the electrically-insulated electrode shaft portion extend out of cannula lumen through the exit opening, the electrode active tip is electrically insulated from the cannula active tip within the assembly of the electrode and the cannula, and the assembly of the electrode and the cannula is configured to conduct electrical current through bodily tissue between the cannula active tip and the electrode active tip.

2. The system of claim 1 wherein the exit opening is a side opening through a side wall of the cannula shaft.

3. The system of claim 2 wherein the electrode shaft is substantially straight, the cannula shaft includes a bend at the location of the side opening configured so that the electrode shaft extends out of the cannula lumen through the side opening in a substantially straight configuration.

4. The system of claim 1 wherein the exit opening is located at the distal end of the cannula shaft along a longitudinal axis of the cannula shaft.

5. The system of claim 4 wherein both the cannula active tip and the electrode active tip are cooled by coolant within the electrode shaft.

6. The system of claim 1 wherein the electrode shaft is cooled by a coolant within the electrode shaft.

7. The system of claim 6 wherein the electrode includes a temperature sensor located at or near the distal end of the electrode shaft.

8. The system of claim 6 wherein the electrode includes a temperature sensor located at a distal point of an extension shaft fixed to a distal end of the electrode active tip; the temperature sensor and the electrode active tip being electrically-isolated from each other within the electrode; the temperature sensor and the coolant being physically separated from each other within the electrode; the extension shaft having a smaller outer diameter than the electrode active tip and extending distal to the electrode active tip so that the temperature sensor is spaced away from the electrode active tip.

9. The system of claim 1 wherein the electrode includes an ionic fluid coolant within the electrode shaft, and one or more perfusion holes in the electrode active tip from which the coolant exits the electrode into the bodily tissue.

10. The system of claim 1 wherein the electrode further includes a temperature sensor.

11. The system of claim 10 wherein the temperature sensor is positioned within a part of the electrically: insulated electrode shaft portion that extends out of cannula lumen through the exit opening when the electrode is assembled with the cannula.

12. The system of claim 1 wherein the cannula further includes a temperature sensor.

13. The system of claim 12 wherein the electrically-insulated cannula shaft portion is covered by electrical insulation, the temperature sensor is positioned under the electrical insulation, wires conducting temperature signals from the temperature sensor to the cannula hub are positioned under the electrical insulation, the engagement of the electrode hub with the cannula hub conducts the temperature signals to the electrosurgical generator via the electrode.

14. The system of claim 1 wherein the cannula hub includes a hub conductive tube, the hub conductive tube forms the proximal opening to the cannula lumen, the hub conductive tube is conductively connected to a conductive tube that runs through the cannula shaft to form the cannula active tip, the cannula hub is covered by electrical insulation except for the hub conductive tube, the electrode hub includes a conductive protrusion configured to conductively engage with the proximal opening of the cannula lumen and thereby conduct the second electrical potential from the electrode to the cannula tip, and the electrode hub is covered by electrical insulation except for the conductive protrusion.

15. The system of claim 14 wherein the hub conductive tube has female-luer geometry, and the conductive protrusion has male-luer geometry.

16. The system of claim 1 wherein the cannula is configured to be inserted into the bodily tissue such that the cannula active tip is fully within the bodily tissue, the electrode is configured to be connected to the electrosurgical generator, and the electrode is configured to be fully inserted into the cannula such that the electrode hub engages with the cannula hub, such that no outer surface of the assembly of the cannula and the electrode outside of the bodily tissue can conduct an electrical signal from within the assembly.

* * * * *